(12) United States Patent
Simpson et al.

(10) Patent No.: US 10,548,478 B2
(45) Date of Patent: Feb. 4, 2020

(54) BALLOON ATHERECTOMY CATHETERS WITH IMAGING

(71) Applicant: Avinger, Inc., Redwood City, CA (US)

(72) Inventors: John B. Simpson, Woodside, CA (US);
Priyanshu Gupta, Palo Alto, CA (US);
Michael Zung, San Carlos, CA (US);
Wendy N. Lam, San Jose, CA (US);
Maegan K. Spencer, Emerald Hills, CA (US); Peter H. Smith, Pacifica, CA (US); Stephen C. Davies, El Dorado Hills, CA (US); Nicholas J. Spinelli, San Mateo, CA (US); Charles W. McNall, Cottonwood Heights, UT (US);
Theodore W. Ketai, San Francisco, CA (US); Manish Kankaria, Fremont, CA (US); Mark W. Askew, San Francisco, CA (US); Kent C. B. Stalker, San Marcos, CA (US)

(73) Assignee: Avinger, Inc., Redwood City, CA (US)

( * ) Notice: Subject to any disclaimer, the term of this patent is extended or adjusted under 35 U.S.C. 154(b) by 736 days.

(21) Appl. No.: 14/424,277

(22) PCT Filed: Mar. 15, 2013

(86) PCT No.: PCT/US2013/032494
§ 371 (c)(1),
(2) Date: Feb. 26, 2015

(87) PCT Pub. No.: WO2014/039099
PCT Pub. Date: Mar. 13, 2014

(65) Prior Publication Data
US 2015/0208922 A1    Jul. 30, 2015
US 2018/0368688 A9    Dec. 27, 2018

Related U.S. Application Data

(63) Continuation-in-part of application No. 13/175,232, filed on Jul. 1, 2011, now Pat. No. 9,345,510.
(Continued)

(51) Int. Cl.
*A61B 5/00* (2006.01)
*A61B 17/3207* (2006.01)

(52) U.S. Cl.
CPC .......... *A61B 5/0066* (2013.01); *A61B 5/0084* (2013.01); *A61B 17/320725* (2013.01); *A61B 17/320758* (2013.01)

(58) Field of Classification Search
CPC ................ A61B 5/0066; A61B 90/361; A61B 17/320758; A61B 17/320725;
(Continued)

(56) References Cited

U.S. PATENT DOCUMENTS 3,908,637 A    9/1975  Doroshow
4,178,935 A    12/1979 Gekhaman et al.
(Continued)

FOREIGN PATENT DOCUMENTS

CN    1875242 A    12/2006
CN    1947652 A    4/2007
(Continued)

OTHER PUBLICATIONS

Simpson et al.; U.S. Appl. No. 14/899,877 entitled "Occusion sheath for imaging catheter," filed Dec. 18, 2015.
(Continued)

*Primary Examiner* — Joel Lamprecht
(74) *Attorney, Agent, or Firm* — Shay Glenn LLP

(57) ABSTRACT

An atherectomy catheter includes an elongate flexible catheter body, a cutter near the distal end of the catheter body, a drive shaft connected to the cutter and extending within the
(Continued)

catheter body, an imaging element near the distal end of the catheter body and an imaging shaft connected to the imaging element and extending within the catheter body. The cutter and the imaging element are mechanically isolated, and the drive shaft is configured to be axially translated relative to the imaging shaft and the catheter body.

33 Claims, 35 Drawing Sheets

Related U.S. Application Data

(60) Provisional application No. 61/697,743, filed on Sep. 6, 2012, provisional application No. 61/360,886, filed on Jul. 1, 2010, provisional application No. 61/468,396, filed on Mar. 28, 2011, provisional application No. 61/492,693, filed on Jun. 2, 2011.

(58) Field of Classification Search
CPC .......... A61B 5/0084; A61B 17/320783; A61B 2017/320791; A61B 2017/22071; A61B 2017/22061; A61B 5/6852
See application file for complete search history.

(56) References Cited

U.S. PATENT DOCUMENTS

| | | | |
|---|---|---|---|
| 4,487,206 A | 12/1984 | Aagard |
| 4,527,553 A | 7/1985 | Upsher |
| 4,552,554 A | 11/1985 | Gould et al. |
| 4,611,600 A | 9/1986 | Cohen |
| 4,621,353 A | 11/1986 | Hazel et al. |
| 4,639,091 A | 1/1987 | Huignard et al. |
| 4,654,024 A | 3/1987 | Crittenden et al. |
| 4,686,982 A | 8/1987 | Nash |
| 4,691,708 A | 9/1987 | Kane |
| 4,771,774 A | 9/1988 | Simpson et al. |
| 4,841,977 A | 6/1989 | Griffith et al. |
| 4,857,046 A | 8/1989 | Stevens et al. |
| 4,920,961 A | 5/1990 | Grossi et al. |
| 4,926,858 A | 5/1990 | Gifford, III et al. |
| 5,000,185 A | 3/1991 | Yock |
| 5,018,529 A | 5/1991 | Tenerz et al. |
| 5,041,082 A | 8/1991 | Shiber |
| 5,047,040 A | 9/1991 | Simpson et al. |
| 5,085,662 A | 2/1992 | Willard |
| 5,099,850 A | 3/1992 | Matsui et al. |
| 5,178,153 A | 1/1993 | Einzig |
| 5,182,291 A | 1/1993 | Gubin et al. |
| 5,190,050 A | 3/1993 | Nitzsche |
| 5,192,291 A | 3/1993 | Pannek, Jr. |
| 5,312,415 A | 5/1994 | Palermo |
| 5,312,425 A | 5/1994 | Evans et al. |
| 5,321,501 A | 6/1994 | Swanson et al. |
| 5,333,142 A | 7/1994 | Scheps |
| 5,358,472 A | 10/1994 | Vance et al. |
| 5,366,464 A | 11/1994 | Belknap |
| 5,383,460 A | 1/1995 | Jang et al. |
| 5,383,467 A | 1/1995 | Auer et al. |
| 5,425,273 A | 6/1995 | Chevalier |
| 5,429,136 A | 7/1995 | Milo et al. |
| 5,431,673 A | 7/1995 | Summers et al. |
| 5,437,284 A | 8/1995 | Trimble |
| 5,459,570 A | 10/1995 | Swanson et al. |
| 5,460,168 A | 10/1995 | Masubuchi et al. |
| 5,465,147 A | 11/1995 | Swanson |
| 5,507,795 A | 4/1996 | Chiang et al. |
| 5,517,998 A | 5/1996 | Madison |
| 5,556,405 A | 9/1996 | Lary |
| 5,607,394 A | 3/1997 | Andersen et al. |
| 5,620,426 A | 4/1997 | Braithwaite |
| 5,632,754 A | 5/1997 | Farley et al. |
| 5,632,755 A | 5/1997 | Nordgren et al. |
| 5,674,232 A | 10/1997 | Halliburton |
| 5,681,336 A | 10/1997 | Clement et al. |
| 5,690,634 A | 11/1997 | Muller et al. |
| 5,722,403 A | 3/1998 | McGee et al. |
| 5,795,295 A | 8/1998 | Hellmuth et al. |
| 5,807,339 A | 9/1998 | Bostrom et al. |
| 5,830,145 A | 11/1998 | Tenhoff |
| 5,836,957 A | 11/1998 | Schulz et al. |
| 5,843,050 A | 12/1998 | Jones et al. |
| 5,843,103 A | 12/1998 | Wulfman |
| 5,868,778 A | 2/1999 | Gershony et al. |
| 5,872,879 A | 2/1999 | Hamm |
| 5,904,651 A | 5/1999 | Swanson et al. |
| 5,907,425 A | 5/1999 | Dickensheets et al. |
| 5,935,075 A | 8/1999 | Casscells et al. |
| 5,938,602 A | 8/1999 | Lloyd |
| 5,951,482 A | 9/1999 | Winston et al. |
| 5,951,581 A | 9/1999 | Saadat et al. |
| 5,951,583 A | 9/1999 | Jensen et al. |
| 5,956,355 A | 9/1999 | Swanson et al. |
| 5,957,952 A | 9/1999 | Gershony et al. |
| 5,987,995 A | 11/1999 | Sawatari et al. |
| 5,997,558 A | 12/1999 | Nash |
| 6,001,112 A | 12/1999 | Taylor |
| 6,007,530 A | 12/1999 | Dornhofer et al. |
| 6,010,449 A | 1/2000 | Selmon et al. |
| 6,013,072 A | 1/2000 | Winston et al. |
| 6,017,359 A | 1/2000 | Gershony et al. |
| 6,027,514 A | 2/2000 | Stine et al. |
| 6,032,673 A | 3/2000 | Savage et al. |
| 6,048,349 A | 4/2000 | Winston et al. |
| 6,080,170 A | 6/2000 | Nash et al. |
| 6,106,515 A | 8/2000 | Winston et al. |
| 6,110,164 A | 8/2000 | Vidlund |
| 6,120,515 A | 9/2000 | Rogers et al. |
| 6,120,516 A | 9/2000 | Selmon et al. |
| 6,134,002 A | 10/2000 | Stimson et al. |
| 6,134,003 A | 10/2000 | Tearney et al. |
| 6,152,938 A | 11/2000 | Curry |
| 6,152,951 A | 11/2000 | Hashimoto et al. |
| 6,160,826 A | 12/2000 | Swanson et al. |
| 6,175,669 B1 | 1/2001 | Colston et al. |
| 6,176,871 B1 | 1/2001 | Pathak et al. |
| 6,183,432 B1 | 2/2001 | Milo |
| 6,193,676 B1 | 2/2001 | Winston et al. |
| 6,206,898 B1 | 3/2001 | Honeycutt et al. |
| 6,228,076 B1 | 5/2001 | Winston et al. |
| 6,241,744 B1 | 6/2001 | Imran et al. |
| 6,283,957 B1 | 9/2001 | Hashimoto et al. |
| 6,290,668 B1 | 9/2001 | Gregory et al. |
| 6,294,775 B1 | 9/2001 | Seibel et al. |
| 6,299,622 B1 | 10/2001 | Snow et al. |
| 6,307,985 B1 | 10/2001 | Murakami et al. |
| 6,402,719 B1 | 6/2002 | Ponzi et al. |
| 6,416,527 B1 | 7/2002 | Berg et al. |
| 6,445,939 B1 | 9/2002 | Swanson et al. |
| 6,445,944 B1 | 9/2002 | Ostrovsky |
| 6,447,525 B2 | 9/2002 | Follmer et al. |
| 6,451,036 B1 | 9/2002 | Heitzmann et al. |
| 6,454,717 B1 | 9/2002 | Pantages et al. |
| 6,454,779 B1 | 9/2002 | Taylor |
| 6,482,216 B1 | 11/2002 | Hiblar et al. |
| 6,482,217 B1 | 11/2002 | Pintor et al. |
| 6,485,413 B1 | 11/2002 | Boppart et al. |
| 6,497,649 B2 | 12/2002 | Parker et al. |
| 6,501,551 B1 | 12/2002 | Tearney et al. |
| 6,503,261 B1 | 1/2003 | Bruneau et al. |
| 6,511,458 B2 | 1/2003 | Milo et al. |
| 6,517,528 B1 | 2/2003 | Pantages et al. |
| 6,542,665 B2 | 4/2003 | Reed et al. |
| 6,544,230 B1 | 4/2003 | Flaherty et al. |
| 6,546,272 B1 | 4/2003 | MacKinnon et al. |
| 6,551,302 B1 | 4/2003 | Rosinko et al. |
| 6,563,105 B2 | 5/2003 | Seibel et al. |
| 6,564,087 B1 | 5/2003 | Pitris et al. |
| 6,565,588 B1 | 5/2003 | Clement et al. |
| 6,572,563 B2 | 6/2003 | Ouchi et al. |
| 6,572,643 B1 | 6/2003 | Gharibadeh |
| 6,575,995 B1 | 6/2003 | Huter et al. |

(56) References Cited

U.S. PATENT DOCUMENTS

| | | |
|---|---|---|
| 6,579,298 B1 | 6/2003 | Bruneau et al. |
| 6,615,071 B1 | 9/2003 | Casscells, III et al. |
| 6,638,233 B2 | 10/2003 | Corvi et al. |
| 6,645,217 B1 | 11/2003 | MacKinnon et al. |
| 6,657,727 B1 | 12/2003 | Izatt et al. |
| 6,666,874 B2 | 12/2003 | Heitzmann et al. |
| 6,687,010 B1 | 2/2004 | Horii |
| 6,728,571 B1 | 4/2004 | Barbato |
| D489,973 S | 5/2004 | Root et al. |
| 6,730,063 B2 | 5/2004 | Delaney et al. |
| 6,758,854 B1 | 7/2004 | Butler et al. |
| 6,760,112 B2 | 7/2004 | Reed et al. |
| 6,800,085 B2 | 10/2004 | Selmon et al. |
| 6,818,001 B2 | 11/2004 | Wulfman et al. |
| 6,824,550 B1 | 11/2004 | Noriega et al. |
| 6,830,577 B2 | 12/2004 | Nash et al. |
| 6,845,190 B1 | 1/2005 | Smithwick et al. |
| 6,852,109 B2 | 2/2005 | Winston et al. |
| 6,853,457 B2 | 2/2005 | Bjarklev et al. |
| 6,856,712 B2 | 2/2005 | Fauver et al. |
| 6,867,753 B2 | 3/2005 | Chinthammit et al. |
| 6,879,851 B2 | 4/2005 | McNamara et al. |
| 6,947,787 B2 | 9/2005 | Webler |
| 6,961,123 B1 | 11/2005 | Wang et al. |
| 6,970,732 B2 | 11/2005 | Winston et al. |
| 6,975,898 B2 | 12/2005 | Seibel |
| 7,068,878 B2 | 6/2006 | Crossman-Bosworth et al. |
| 7,074,231 B2 | 7/2006 | Jang |
| 7,126,693 B2 | 10/2006 | Everett et al. |
| 7,172,610 B2 | 2/2007 | Heitzmann et al. |
| 7,242,480 B2 | 7/2007 | Alphonse |
| 7,261,687 B2 | 8/2007 | Yang |
| 7,288,087 B2 | 10/2007 | Winston et al. |
| 7,291,146 B2 | 11/2007 | Steinke et al. |
| 7,297,131 B2 | 11/2007 | Nita |
| 7,311,723 B2 | 12/2007 | Seibel et al. |
| 7,344,546 B2 | 3/2008 | Wulfman et al. |
| 7,366,376 B2 | 4/2008 | Shishkov et al. |
| 7,382,949 B2 | 6/2008 | Bouma et al. |
| 7,426,036 B2 | 9/2008 | Feldchtein et al. |
| 7,428,001 B2 | 9/2008 | Schowengerdt et al. |
| 7,428,053 B2 | 9/2008 | Feldchtein et al. |
| 7,455,649 B2 | 11/2008 | Root et al. |
| 7,474,407 B2 | 1/2009 | Gutin |
| 7,485,127 B2 | 2/2009 | Nistal |
| 7,488,340 B2 | 2/2009 | Kauphusman et al. |
| 7,530,948 B2 | 5/2009 | Seibel et al. |
| 7,530,976 B2 | 5/2009 | MacMahon et al. |
| 7,538,859 B2 | 5/2009 | Tearney et al. |
| 7,538,886 B2 | 5/2009 | Feldchtein |
| 7,539,362 B2 | 5/2009 | Teramura |
| 7,542,145 B2 | 6/2009 | Toida et al. |
| 7,544,162 B2 | 6/2009 | Ohkubo |
| 7,545,504 B2 | 6/2009 | Buckland et al. |
| 7,555,333 B2 | 6/2009 | Wang et al. |
| 7,577,471 B2 | 8/2009 | Camus et al. |
| 7,583,872 B2 | 9/2009 | Seibel et al. |
| 7,616,986 B2 | 11/2009 | Seibel et al. |
| 7,637,885 B2 | 12/2009 | Maschke |
| 7,674,253 B2 | 3/2010 | Fisher et al. |
| 7,682,319 B2 | 3/2010 | Martin et al. |
| 7,706,863 B2 | 4/2010 | Imanishi et al. |
| 7,708,749 B2 * | 5/2010 | Simpson ........ A61B 17/320758 606/159 |
| 7,728,985 B2 | 6/2010 | Feldchtein et al. |
| 7,729,745 B2 | 6/2010 | Maschke |
| 7,734,332 B2 | 6/2010 | Sher |
| 7,738,945 B2 | 6/2010 | Fauver et al. |
| 7,753,852 B2 | 7/2010 | Maschke |
| 7,771,425 B2 | 8/2010 | Dycus et al. |
| 7,785,286 B2 | 8/2010 | Magnin et al. |
| 7,813,609 B2 | 10/2010 | Petersen et al. |
| 7,821,643 B2 | 10/2010 | Amazeen et al. |
| 7,824,089 B2 | 11/2010 | Charles |
| 7,840,283 B1 | 11/2010 | Bush et al. |
| 7,944,568 B2 | 5/2011 | Teramura et al. |
| 7,952,718 B2 | 5/2011 | Li et al. |
| 7,972,299 B2 | 7/2011 | Carter et al. |
| 8,059,274 B2 | 11/2011 | Splinter |
| 8,062,316 B2 | 11/2011 | Patel et al. |
| 8,068,921 B2 | 11/2011 | Prakash et al. |
| 8,313,493 B2 | 11/2012 | Fisher |
| 8,361,097 B2 | 1/2013 | Patel et al. |
| 8,548,571 B2 | 10/2013 | He et al. |
| 8,548,603 B2 | 10/2013 | Swoyer et al. |
| 8,632,557 B2 | 1/2014 | Thatcher et al. |
| 8,644,913 B2 | 2/2014 | Simpson et al. |
| 8,647,335 B2 | 2/2014 | Markus |
| 8,696,695 B2 * | 4/2014 | Patel ............ A61B 17/320758 606/159 |
| 8,911,459 B2 | 12/2014 | Simpson et al. |
| 9,119,662 B2 | 9/2015 | Moberg |
| 9,333,007 B2 | 5/2016 | Escudero et al. |
| 9,345,510 B2 * | 5/2016 | Patel ................ A61B 1/00179 |
| 9,345,511 B2 | 5/2016 | Smith et al. |
| 9,351,757 B2 | 5/2016 | Kusleika |
| 9,498,600 B2 * | 11/2016 | Rosenthal ........ A61B 17/32075 |
| 2001/0020126 A1 | 9/2001 | Swanson et al. |
| 2002/0019644 A1 | 2/2002 | Hastings et al. |
| 2002/0072706 A1 | 6/2002 | Hiblar et al. |
| 2002/0082626 A1 | 6/2002 | Donohoe et al. |
| 2002/0111548 A1 | 8/2002 | Swanson et al. |
| 2002/0115931 A1 | 8/2002 | Strauss et al. |
| 2002/0147459 A1 | 10/2002 | Bashiri et al. |
| 2002/0158547 A1 | 10/2002 | Wood |
| 2003/0002038 A1 | 1/2003 | Mawatari |
| 2003/0028100 A1 | 2/2003 | Tearney et al. |
| 2003/0032880 A1 | 2/2003 | Moore |
| 2003/0045835 A1 | 3/2003 | Anderson et al. |
| 2003/0095248 A1 | 5/2003 | Frot |
| 2003/0097044 A1 | 5/2003 | Rovegno |
| 2003/0120150 A1 | 6/2003 | Govari |
| 2003/0120295 A1 | 6/2003 | Simpson et al. |
| 2003/0125756 A1 | 7/2003 | Shturman et al. |
| 2003/0125757 A1 | 7/2003 | Patel et al. |
| 2003/0125758 A1 | 7/2003 | Simpson et al. |
| 2003/0139751 A1 | 7/2003 | Evans et al. |
| 2003/0181855 A1 | 9/2003 | Simpson et al. |
| 2004/0002650 A1 | 1/2004 | Mandrusov et al. |
| 2004/0039371 A1 | 2/2004 | Tockman et al. |
| 2004/0057667 A1 | 3/2004 | Yamada et al. |
| 2004/0059257 A1 | 3/2004 | Gaber |
| 2004/0082850 A1 | 4/2004 | Bonner et al. |
| 2004/0092915 A1 | 5/2004 | Levatter |
| 2004/0093001 A1 | 5/2004 | Hamada |
| 2004/0147934 A1 | 7/2004 | Kiester |
| 2004/0167553 A1 | 8/2004 | Simpson et al. |
| 2004/0167554 A1 | 8/2004 | Simpson et al. |
| 2004/0181249 A1 | 9/2004 | Torrance et al. |
| 2004/0186368 A1 | 9/2004 | Ramzipoor et al. |
| 2004/0202418 A1 | 10/2004 | Ghiron et al. |
| 2004/0220519 A1 | 11/2004 | Wulfman et al. |
| 2004/0230212 A1 | 11/2004 | Wulfman |
| 2004/0230213 A1 | 11/2004 | Wulfman et al. |
| 2004/0236312 A1 | 11/2004 | Nistal et al. |
| 2004/0243162 A1 | 12/2004 | Wulfman et al. |
| 2004/0254599 A1 | 12/2004 | Lipoma et al. |
| 2004/0260236 A1 | 12/2004 | Manning et al. |
| 2005/0020925 A1 | 1/2005 | Kleen et al. |
| 2005/0043614 A1 | 2/2005 | Huizenga et al. |
| 2005/0054947 A1 | 3/2005 | Goldenberg |
| 2005/0075660 A1 | 4/2005 | Chu et al. |
| 2005/0085708 A1 | 4/2005 | Fauver et al. |
| 2005/0085721 A1 | 4/2005 | Fauver et al. |
| 2005/0105097 A1 | 5/2005 | Fang-Yen et al. |
| 2005/0141843 A1 | 6/2005 | Warden et al. |
| 2005/0154407 A1 | 7/2005 | Simpson |
| 2005/0159712 A1 | 7/2005 | Andersen |
| 2005/0159731 A1 | 7/2005 | Lee |
| 2005/0171478 A1 | 8/2005 | Selmon et al. |
| 2005/0177068 A1 | 8/2005 | Simpson |
| 2005/0182295 A1 | 8/2005 | Soper et al. |
| 2005/0187571 A1 * | 8/2005 | Maschke ............ A61B 5/0066 606/159 |

(56) References Cited

U.S. PATENT DOCUMENTS

| | | |
|---|---|---|
| 2005/0192496 A1 | 9/2005 | Maschke |
| 2005/0201662 A1 | 9/2005 | Petersen et al. |
| 2005/0203553 A1 | 9/2005 | Maschke |
| 2005/0222519 A1 | 10/2005 | Simpson |
| 2005/0222663 A1 | 10/2005 | Simpson et al. |
| 2005/0251116 A1 | 11/2005 | Steinke et al. |
| 2006/0011820 A1 | 1/2006 | Chow-Shing et al. |
| 2006/0032508 A1 | 2/2006 | Simpson |
| 2006/0046235 A1 | 3/2006 | Alexander |
| 2006/0049587 A1 | 3/2006 | Cornwell |
| 2006/0064009 A1 | 3/2006 | Webler et al. |
| 2006/0084911 A1 | 4/2006 | Belef et al. |
| 2006/0109478 A1 | 5/2006 | Tearney et al. |
| 2006/0135870 A1 | 6/2006 | Webler |
| 2006/0173475 A1 | 8/2006 | Lafontaine et al. |
| 2006/0229646 A1 | 10/2006 | Sparks |
| 2006/0229659 A1 | 10/2006 | Gifford et al. |
| 2006/0235262 A1 | 10/2006 | Arnal et al. |
| 2006/0235366 A1 | 10/2006 | Simpson |
| 2006/0236019 A1 | 10/2006 | Soito et al. |
| 2006/0239982 A1 | 10/2006 | Simpson |
| 2006/0241503 A1 | 10/2006 | Schmitt et al. |
| 2006/0244973 A1 | 11/2006 | Yun et al. |
| 2006/0252993 A1 | 11/2006 | Freed et al. |
| 2006/0264741 A1 | 11/2006 | Prince |
| 2006/0264743 A1 | 11/2006 | Kleen et al. |
| 2006/0264907 A1 | 11/2006 | Eskridge et al. |
| 2007/0010840 A1 | 1/2007 | Rosenthal et al. |
| 2007/0015969 A1 | 1/2007 | Feldman et al. |
| 2007/0015979 A1 | 1/2007 | Redel |
| 2007/0035855 A1 | 2/2007 | Dickensheets |
| 2007/0038061 A1 | 2/2007 | Huennekens et al. |
| 2007/0038125 A1 | 2/2007 | Kleen et al. |
| 2007/0038173 A1 | 2/2007 | Simpson |
| 2007/0078469 A1 | 4/2007 | Soito et al. |
| 2007/0078500 A1 | 4/2007 | Ryan et al. |
| 2007/0081166 A1 | 4/2007 | Brown et al. |
| 2007/0088230 A1 | 4/2007 | Terashi et al. |
| 2007/0106155 A1 | 5/2007 | Goodnow et al. |
| 2007/0135712 A1 | 6/2007 | Maschke |
| 2007/0196926 A1 | 8/2007 | Soito et al. |
| 2007/0219484 A1 | 9/2007 | Straub |
| 2007/0250080 A1 | 10/2007 | Jones et al. |
| 2007/0255252 A1 | 11/2007 | Mehta |
| 2007/0270647 A1 | 11/2007 | Nahen et al. |
| 2007/0276419 A1 | 11/2007 | Rosenthal |
| 2007/0288036 A1 | 12/2007 | Seshadri |
| 2007/0299309 A1 | 12/2007 | Seibel et al. |
| 2008/0004643 A1 | 1/2008 | To et al. |
| 2008/0004644 A1 | 1/2008 | To et al. |
| 2008/0004645 A1 | 1/2008 | To et al. |
| 2008/0004646 A1 | 1/2008 | To et al. |
| 2008/0015491 A1 | 1/2008 | Bei et al. |
| 2008/0027334 A1 | 1/2008 | Langston |
| 2008/0033396 A1 | 2/2008 | Danek et al. |
| 2008/0045986 A1 | 2/2008 | To et al. |
| 2008/0049234 A1 | 2/2008 | Seitz |
| 2008/0058629 A1 | 3/2008 | Seibel et al. |
| 2008/0065124 A1 | 3/2008 | Olson |
| 2008/0065125 A1 | 3/2008 | Olson |
| 2008/0065205 A1 | 3/2008 | Nguyen et al. |
| 2008/0103439 A1 | 5/2008 | Torrance et al. |
| 2008/0103446 A1 | 5/2008 | Torrance et al. |
| 2008/0103516 A1 | 5/2008 | Wulfman et al. |
| 2008/0139897 A1 | 6/2008 | Ainsworth et al. |
| 2008/0146942 A1 | 6/2008 | Dala-Krishna |
| 2008/0147000 A1 | 6/2008 | Seibel et al. |
| 2008/0154293 A1 | 6/2008 | Taylor et al. |
| 2008/0177138 A1 | 7/2008 | Courtney et al. |
| 2008/0186501 A1 | 8/2008 | Xie |
| 2008/0221388 A1 | 9/2008 | Seibel et al. |
| 2008/0228033 A1 | 9/2008 | Tumlinson et al. |
| 2008/0243030 A1 | 10/2008 | Seibel et al. |
| 2008/0243031 A1 | 10/2008 | Seibel et al. |
| 2008/0262312 A1 | 10/2008 | Carroll et al. |
| 2008/0275485 A1 | 11/2008 | Bonnette et al. |
| 2009/0018565 A1 | 1/2009 | To et al. |
| 2009/0018566 A1 | 1/2009 | Escudero et al. |
| 2009/0018567 A1 | 1/2009 | Escudero et al. |
| 2009/0024084 A1 | 1/2009 | Khosla et al. |
| 2009/0024085 A1 | 1/2009 | To et al. |
| 2009/0024191 A1 | 1/2009 | Seibel et al. |
| 2009/0028407 A1 | 1/2009 | Seibel et al. |
| 2009/0028507 A1 | 1/2009 | Jones et al. |
| 2009/0073444 A1 | 3/2009 | Wang |
| 2009/0093764 A1 | 4/2009 | Pfeffer et al. |
| 2009/0099641 A1 | 4/2009 | Wu et al. |
| 2009/0125019 A1 | 5/2009 | Douglass et al. |
| 2009/0135280 A1 | 5/2009 | Johnston et al. |
| 2009/0137893 A1 | 5/2009 | Seibel et al. |
| 2009/0152664 A1 | 6/2009 | Tian et al. |
| 2009/0185135 A1 | 7/2009 | Volk |
| 2009/0196554 A1 | 8/2009 | Irisawa |
| 2009/0198125 A1 | 8/2009 | Nakabayashi et al. |
| 2009/0208143 A1 | 8/2009 | Yoon et al. |
| 2009/0216180 A1 | 8/2009 | Lee et al. |
| 2009/0221904 A1 | 9/2009 | Shealy et al. |
| 2009/0221920 A1 | 9/2009 | Boppart et al. |
| 2009/0235396 A1 | 9/2009 | Wang et al. |
| 2009/0244485 A1 | 10/2009 | Walsh et al. |
| 2009/0244547 A1 | 10/2009 | Ozawa |
| 2009/0264826 A1 | 10/2009 | Thompson |
| 2009/0284749 A1 | 11/2009 | Johnson et al. |
| 2009/0292199 A1 | 11/2009 | Bielewicz et al. |
| 2009/0299394 A1* | 12/2009 | Simpson ........ A61B 17/320758 606/159 |
| 2009/0306520 A1 | 12/2009 | Schmitt et al. |
| 2009/0316116 A1 | 12/2009 | Melville et al. |
| 2009/0318862 A1 | 12/2009 | Ali et al. |
| 2010/0049225 A1 | 2/2010 | To et al. |
| 2010/0080016 A1 | 4/2010 | Fukui et al. |
| 2010/0125253 A1 | 5/2010 | Olson |
| 2010/0130996 A1 | 5/2010 | Doud et al. |
| 2010/0198240 A1* | 8/2010 | Simpson ........ A61B 17/320758 606/159 |
| 2010/0241147 A1 | 9/2010 | Maschke |
| 2010/0253949 A1 | 10/2010 | Adler et al. |
| 2010/0292539 A1 | 11/2010 | Lankenau et al. |
| 2010/0292721 A1 | 11/2010 | Moberg |
| 2010/0305452 A1 | 12/2010 | Black et al. |
| 2010/0312263 A1 | 12/2010 | Moberg et al. |
| 2010/0317973 A1 | 12/2010 | Nita |
| 2010/0324472 A1 | 12/2010 | Wulfman |
| 2011/0004107 A1 | 1/2011 | Rosenthal et al. |
| 2011/0021926 A1 | 1/2011 | Spencer et al. |
| 2011/0023617 A1 | 2/2011 | Miao et al. |
| 2011/0028977 A1 | 2/2011 | Rauscher et al. |
| 2011/0040238 A1 | 2/2011 | Wulfman et al. |
| 2011/0058250 A1 | 3/2011 | Liu et al. |
| 2011/0060186 A1 | 3/2011 | Tilson et al. |
| 2011/0071401 A1 | 3/2011 | Hastings et al. |
| 2011/0092955 A1 | 4/2011 | Purdy et al. |
| 2011/0106004 A1 | 5/2011 | Eubanks et al. |
| 2011/0118660 A1 | 5/2011 | Torrance et al. |
| 2011/0130777 A1 | 6/2011 | Zhang et al. |
| 2011/0144673 A1 | 6/2011 | Zhang et al. |
| 2011/0201924 A1 | 8/2011 | Tearney et al. |
| 2011/0208222 A1 | 8/2011 | Ljahnicky et al. |
| 2011/0257478 A1 | 10/2011 | Kleiner et al. |
| 2011/0264125 A1 | 10/2011 | Wilson et al. |
| 2011/0270187 A1 | 11/2011 | Nelson |
| 2011/0295148 A1 | 12/2011 | Destoumieux et al. |
| 2011/0301625 A1 | 12/2011 | Mauch et al. |
| 2011/0319905 A1 | 12/2011 | Palme et al. |
| 2012/0002928 A1 | 1/2012 | Irisawa |
| 2012/0004506 A1 | 1/2012 | Tearney et al. |
| 2012/0046679 A1 | 2/2012 | Patel et al. |
| 2012/0123352 A1 | 5/2012 | Fruland et al. |
| 2012/0238869 A1 | 9/2012 | Schmitt et al. |
| 2012/0259337 A1 | 10/2012 | del Rio et al. |
| 2012/0289971 A1 | 11/2012 | Segermark et al. |
| 2013/0035692 A1 | 2/2013 | Sorensen et al. |
| 2013/0096589 A1 | 4/2013 | Spencer et al. |
| 2013/0123615 A1 | 5/2013 | Spencer et al. |

(56) References Cited

U.S. PATENT DOCUMENTS

| | | |
|---|---|---|
| 2013/0138128 A1 | 5/2013 | Patel et al. |
| 2013/0211221 A1 | 8/2013 | Sunnarborg et al. |
| 2013/0223798 A1 | 8/2013 | Jenner et al. |
| 2013/0223801 A1 | 8/2013 | Bhagavatula et al. |
| 2013/0255069 A1 | 10/2013 | Higashi et al. |
| 2013/0266259 A1 | 10/2013 | Bhagavatula et al. |
| 2013/0289392 A1 | 10/2013 | Patel et al. |
| 2013/0296695 A1 | 11/2013 | Spencer et al. |
| 2013/0317519 A1 | 11/2013 | Romo et al. |
| 2014/0005534 A1 | 1/2014 | He et al. |
| 2014/0128893 A1 | 5/2014 | Guggenheimer et al. |
| 2014/0187949 A1 | 7/2014 | Zhao et al. |
| 2014/0213893 A1 | 7/2014 | Simpson et al. |
| 2014/0222047 A1 | 8/2014 | Vreeman |
| 2014/0371718 A1 | 12/2014 | Alvarez et al. |
| 2015/0025310 A1 | 1/2015 | Everingham et al. |
| 2015/0099984 A1 | 4/2015 | Kankaria |
| 2015/0126856 A1 | 5/2015 | Tachibana et al. |
| 2015/0164530 A1 | 6/2015 | Carver et al. |
| 2015/0208922 A1 | 7/2015 | Newhauser et al. |
| 2016/0192962 A1 | 7/2016 | Simpson et al. |
| 2016/0199092 A1 | 7/2016 | Patel et al. |
| 2018/0049700 A1 | 2/2018 | Black et al. |
| 2018/0192880 A1 | 7/2018 | Patel et al. |
| 2018/0207417 A1 | 7/2018 | Zung et al. |
| 2018/0256187 A1 | 9/2018 | Patel et al. |
| 2019/0021679 A1 | 1/2019 | Christensen |
| 2019/0021760 A1 | 1/2019 | Newhauser et al. |
| 2019/0029714 A1 | 1/2019 | Patel et al. |

FOREIGN PATENT DOCUMENTS

| | | |
|---|---|---|
| CN | 101601581 A | 12/2009 |
| CN | 103027727 A | 4/2013 |
| DE | 202006018883.5 U1 | 2/2007 |
| EP | 0347098 A2 | 12/1989 |
| EP | 0808638 A1 | 11/1997 |
| EP | 1859732 A1 | 11/2007 |
| EP | 2353526 B1 | 9/2013 |
| JP | S62-275425 A | 11/1987 |
| JP | 03502060 A | 2/1990 |
| JP | 05103763 A | 4/1993 |
| JP | H06-027343 A | 2/1994 |
| JP | H07-308393 A | 11/1995 |
| JP | 2002-214127 A | 7/2002 |
| JP | 2004-509695 A | 4/2004 |
| JP | 2004-516073 | 6/2004 |
| JP | 2005-114473 A | 4/2005 |
| JP | 2005-249704 A | 9/2005 |
| JP | 2005230550 A | 9/2005 |
| JP | 2005-533533 A | 11/2005 |
| JP | 2008-175698 A | 7/2006 |
| JP | 2006-288775 A | 10/2006 |
| JP | 2006-313158 A | 11/2006 |
| JP | 2006-526790 | 11/2006 |
| JP | 2006-326157 A | 12/2006 |
| JP | 2007-83053 A | 4/2007 |
| JP | 2007-83057 A | 4/2007 |
| JP | 2007-225349 A | 9/2007 |
| JP | 2007533361 A | 11/2007 |
| JP | 2008-023627 | 2/2008 |
| JP | 2008-128708 A | 6/2008 |
| JP | 2008-145376 A | 6/2008 |
| JP | 2008-183208 A | 8/2008 |
| JP | 2008-253492 A | 10/2008 |
| JP | 2009-14751 A | 1/2009 |
| JP | 2009-509690 A | 3/2009 |
| JP | 2009-66252 A | 4/2009 |
| JP | 2009-78150 A | 4/2009 |
| JP | 2010042182 A | 2/2010 |
| JP | 2010518900 A | 6/2010 |
| JP | 2011521747 A | 7/2011 |
| JP | 2012143558 A | 8/2012 |
| JP | 2012533353 A | 12/2012 |
| JP | 2016508758 A | 3/2016 |
| KR | 2007/0047221 | 5/2007 |
| RU | 2185859 C2 | 7/2002 |
| RU | 2218191 C2 | 12/2003 |
| WO | WO 91/17698 A1 | 11/1991 |
| WO | WO 99/23958 A1 | 5/1999 |
| WO | WO 00/54659 A1 | 9/2000 |
| WO | WO01/15609 A1 | 3/2001 |
| WO | WO 01/76680 A1 | 10/2001 |
| WO | WO 2006/133030 A2 | 12/2006 |
| WO | WO2008/005888 A2 | 1/2008 |
| WO | WO 2008/029506 A | 3/2008 |
| WO | WO 2008/042987 A2 | 4/2008 |
| WO | WO2008/051951 A1 | 5/2008 |
| WO | WO 2008/065600 A2 | 6/2008 |
| WO | WO 2008/086613 A1 | 7/2008 |
| WO | WO 2008/087613 A2 | 7/2008 |
| WO | WO2009/005779 A1 | 1/2009 |
| WO | WO2009/006335 A1 | 1/2009 |
| WO | WO 2009/009799 A1 | 1/2009 |
| WO | WO2009/009802 A1 | 1/2009 |
| WO | WO 2009/023635 A | 2/2009 |
| WO | WO2009/024344 A1 | 2/2009 |
| WO | WO 2009/094341 A2 | 7/2009 |
| WO | WO 2009/140617 A2 | 11/2009 |
| WO | WO2009/148317 A1 | 12/2009 |
| WO | WO2010/039464 A1 | 4/2010 |
| WO | WO2010/056771 A1 | 5/2010 |
| WO | WO2011/044387 A2 | 4/2011 |
| WO | WO2011/062087 A1 | 5/2011 |
| WO | WO 2012/061935 A1 | 5/2012 |
| WO | WO2012/166332 A1 | 12/2012 |
| WO | WO2013/033490 A1 | 3/2013 |
| WO | WO2013/056262 A1 | 4/2013 |
| WO | WO2014/093148 A2 | 6/2014 |

OTHER PUBLICATIONS

Simpson et al.; U.S. Appl. No. 14/899,893 entitled "Identification of elastic lamina to guide interventional therapy," filed Dec. 18, 2015.
Rosenthal et al.; U.S. Appl. No. 15/354,898 entitled "Atherectomy catheter with laterally-displaceable tip," filed Nov. 17, 2017.
Patel et al.; U.S. Appl. No. 15/354,842 entitled "Atherectomy catheters and occlusion crossing devices," filed Nov. 17, 2016.
Patel et al.; U.S. Appl. No. 15/162,330 entitled "Atherectomy catheters with longitudinally displaceable drive shafts," filed May 23, 2016.
Spencer et al.; U.S. Appl. No. 15/162,353 entitled "Occlusion-crossing devices, atherectomy devices, and imaging," filed May 23, 2016.
Tachibana et al.; U.S. Appl. No. 15/162,391 entitled "Atherectomy catheter drive assemblies," filed May 23, 2016.
Shinkle et al.; Evaluation of stent placement and outcomes with optical coherence tomography; Interv. Cardiol.; 2(4); pp. 535-543; (manuscript version, 12 pages); Aug. 2010.
Patel et al.; U.S. Appl. No. 15/324,325 entitled "High speed chronic total occulusion crossing devices," filed Jan. 6, 2017.
Kankaria; U.S. Appl. No. 15/419,815 entitled "Optical coherence tomography with graded index fiber for biological imaging," filed Jan. 30, 2017.
Simpson et al.; U.S. Appl. No. 15/434,758 entitled "Occlusion-crossing devices, imaging, and atherectomy devices," filed Feb. 16, 2017.
Simpson et al.; U.S. Appl. No. 15/457,960 entitled "Atherectomy catheters devices having multi-channel bushings," filed Mar. 13, 2017.
Patel et al.; U.S. Appl. No. 15/480,238 entitled "Guidewire positioning catheter," filed Apr. 5, 2017.
Gupta et al.; U.S. Appl. No. 14/776,749 entitled "Tissue collection device for catheter," filed Sep. 15, 2015.
Smith et al.; U.S. Appl. No. 14/776,750 entitled "Chronic total occlusion crossing devices with imaging," filed Sep. 15, 2015.
Smith et al.; U.S. Appl. No. 14/776,748 entitled "Optical pressure sensor assembly," filed Sep. 15, 2015.
Gupta et al.; U.S. Appl. No. 14/401,175 entitled "Atherectomy catheters with imaging," filed Nov. 14, 2014.

(56) References Cited

OTHER PUBLICATIONS

Simpson et al.; U.S. Appl. No. 14/424,266 entitled "Re-entry stylet for catheter," filed Feb. 26, 2015.

Aziz et al.; Chronic total occlusions—a stiff challege requiring a major breakthrough: is there light at the end of the tunnel?; Heart; vol. 91; suppl. III; pp. 42-48; Jun. 2005.

Emkey et al.; Analysis and evaluation of graded-index fiber-lenses; Journal of Lightwave Technology; vol. LT-5; No. 9; pp. 1156-1164; Sep. 1987.

Gonzalo et al.; Optical coherence tomography patterns of stent restenosis; Am. Heart J.; 158(2); pp. 284-293; Aug. 2009.

Linares et al.; Arbitrary single-mode coupling by tapered and nontapered grin fiber lenses; Applied Optics; vol. 29; No. 28; pp. 4003-4007; Oct. 1, 1990.

Sharma et al.; Optical coherence tomography based on an all-fiber autocorrelator using probe-end reflection as reference; CWJ13; San Francisco, California; CLEO May 16, 2004; 4 pages.

Suparno et al.; Light scattering with single-mode fiber collimators; Applied Optics; vol. 33; No. 30; pp. 7200-7205; Oct. 20, 1994.

Han et al.; In situ Frog Retina Imaging Using Common-Path OCT with a Gold-Coated Bare Fiber Probe; CFM6; San Jose, California; CLEO, May 4, 2008; 2 pages.

Muller et al.; Time-gated infrared fourier-domain optical coherence tomography; CFM5; San Jose, California; CLEO May 4, 2008; 2 pages.

Tanaka et al.; Challenges on the frontier of intracoronary imaging: atherosclerotic plaque macrophage measurement by optical coherence tomography; Journal of Biomedical Optics; 15(1); pp.(011104-1)-(011104-8); Jan.-Feb. 2010.

Wang et al.; Common-path endoscopic Fourier domain OCT with a reference Michelson interferometer; Proceedings of the SPIE; vol. 7566; pp. 75660L-75660L-7; Jan. 2010.

Smith et al.; U.S. Appl. No. 15/854,579 entitled "Chronic total occusion crossing devices with imaging," filed Dec. 26, 2017.

Rosenthal et al.; U.S. Appl. No. 16/105,743 entitled "Atherectomy catheter with laterally-displaceable tip," filed Aug. 20, 2018.

Simpson et al.; U.S. Appl. No. 16/194,183 entitled "Indetification of elastic lamina to guide interventional therapy," filed Nov. 16, 2018.

Fernandez et al., U.S. Appl. No. 16/305,136 entitled "Catheter device with detachable distal end," filed Nov. 28, 2018.

Patel et al., U.S. Appl. No. 16/310,470 entitled "Atherectomy catheter with shapeable distal tip," filed Dec. 17, 2019.

Choma et al.; Sensitivity advantage of swept source and fourier domain optical coherence tomography; Optics Express; 11(18); pp. 2183-2189; Sep. 8, 2003.

De Boer et al.; Improved signal-to-noise ratio in spectral-domain compared with time-domain optical coherence tomography; Optics Letters; 28(21); pp. 2067-2069; Nov. 2003.

Leitgeb et al.; Performance of fourier domain vs time domain optical coherence tomography; Optics Express; 11(8); pp. 889-894; Apr. 21, 2003.

Rollins et al.; Optimal interferometer designs for optical coherence tomography; Optics Letters; 24(21); pp. 1484-1486; Nov. 1999.

\* cited by examiner

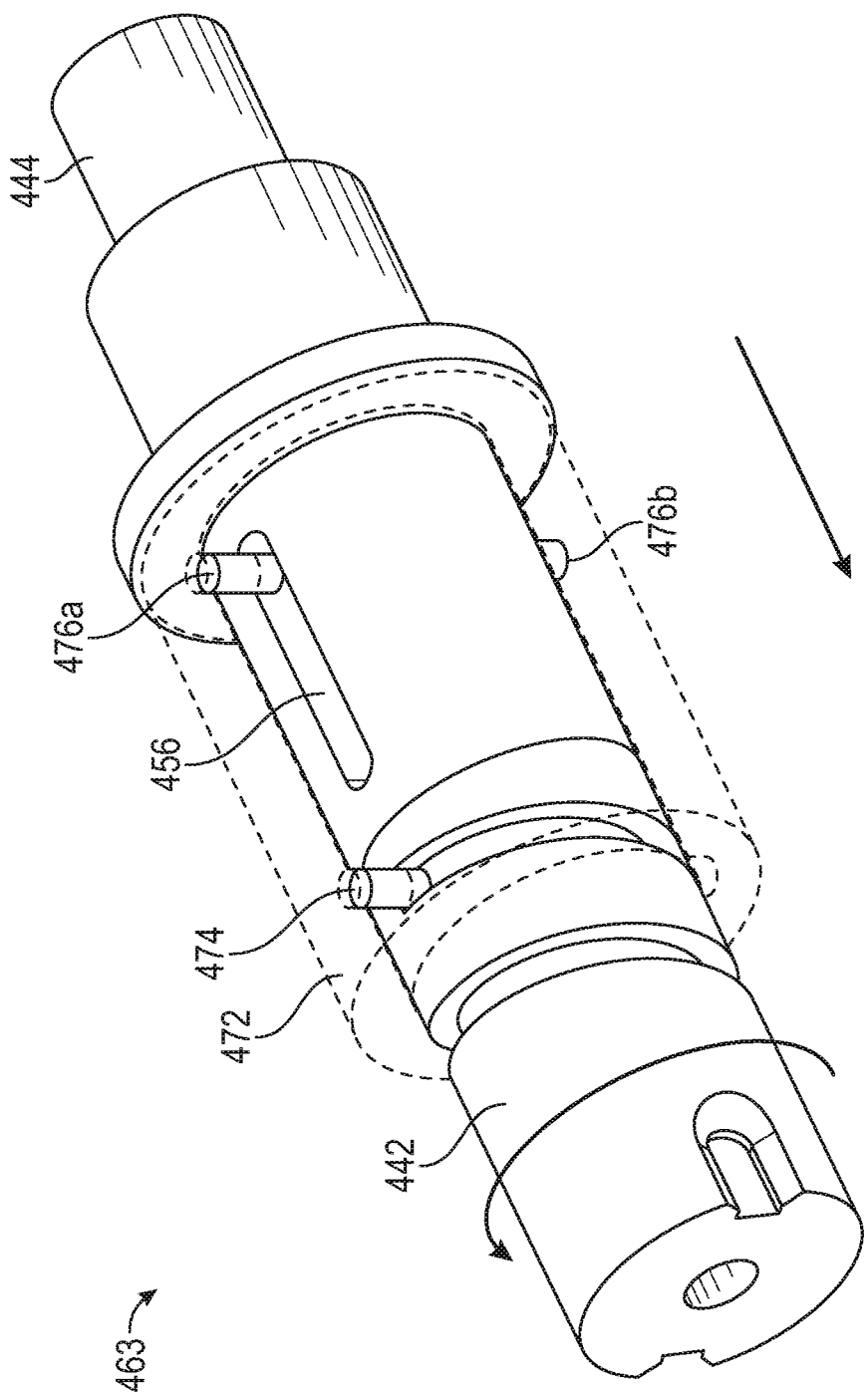

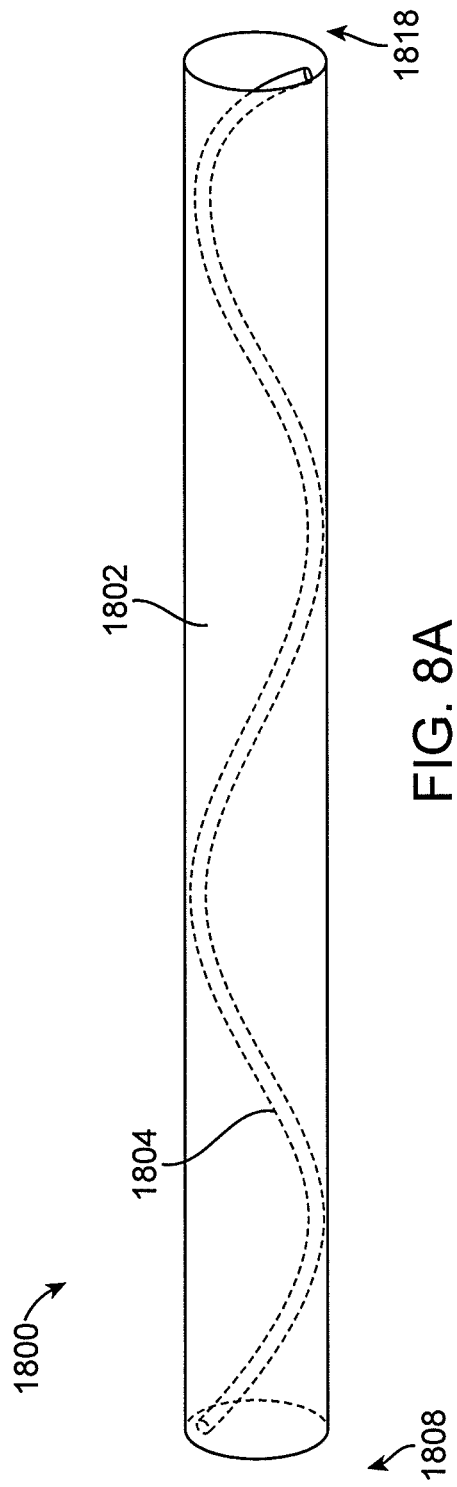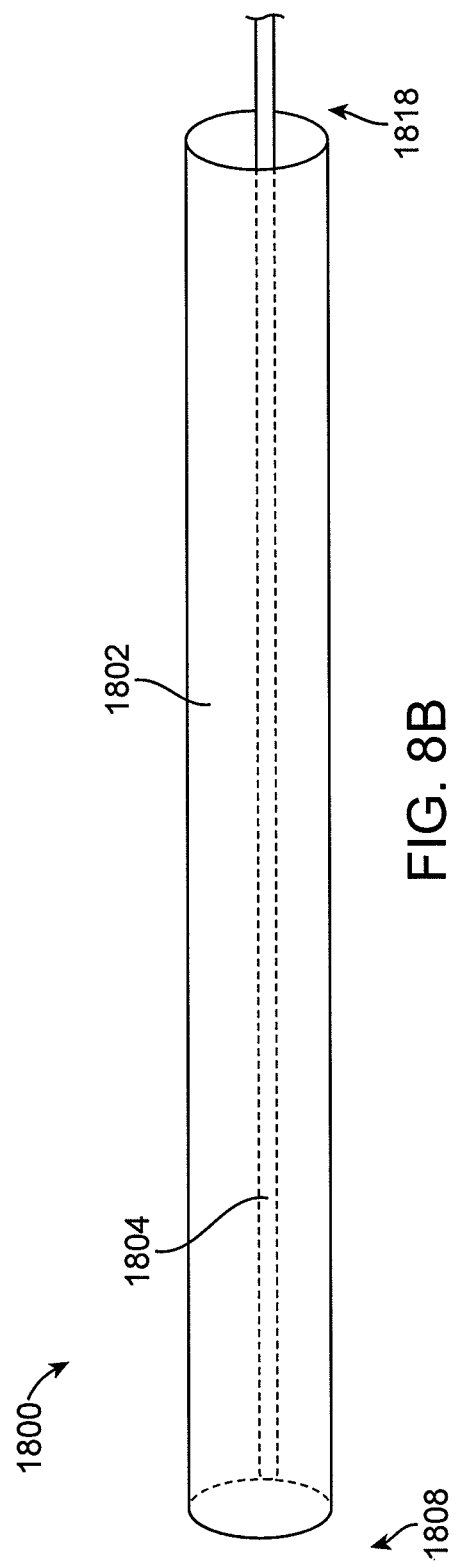
FIG. 8A
FIG. 8B

BALLOON ATHERECTOMY CATHETERS WITH IMAGING

CROSS REFERENCE TO RELATED APPLICATIONS

This patent application is a 371 of International Application No. PCT/US13/32494, filed Mar. 15, 2013, titled "BALLOON ATHERECTOMY CATHETERS WITH IMAGING", which claims priority to U.S. Patent Application No. 61/697,743, titled "BALLOON ATHERECTOMY CATHETERS WITH IMAGING," filed on Sep. 6, 2012, which is incorporated by reference herein. This application is also a continuation-in-part of U.S. patent application Ser. No. 13/175,232, filed Jul. 1, 2011, now U.S. Pat. No. 9,345,510, titled "ATHERECTOMY CATHETERS WITH LONGITUDINALLY DISPLACEABLE DRIVE SHAFTS", which claims priority to Provisional Application No. 61/492,693, filed Jun. 2, 2011, titled "ATHERECTOMY CATHETERS WITH LONGITUDINALLY DISPLACEABLE DRIVE SHAFTS", Provisional Application No. 61/468,396, filed Mar. 28, 2011, titled "OCCLUSION-CROSSING DEVICES, IMAGING, AND ATHERECTOMY DEVICES", and Provisional Application No. 61/360,886, filed Jul. 1, 2010, titled "ATHERECTOMY CATHETERS WITH LONGITUDINALLY DISPLACEABLE DRIVE SHAFTS".

INCORPORATION BY REFERENCE

All publications and patent applications mentioned in this specification are herein incorporated by reference to the same extent as if each individual publication or patent application was specifically and individually indicated to be incorporated by reference.

BACKGROUND

A significant body of scientific and clinical evidence supports atherectomy as a viable primary or adjunctive therapy prior to stenting for the treatment of occlusive arterial disease.

Atherectomy offers a simple mechanical advantage over alternative therapies. By removing the majority of plaque mass (debulking), it creates a larger initial lumen and dramatically increases the compliance of the arterial wall. As a result, stent deployment is greatly enhanced.

Additionally, atherectomy provides several advantages related to the arterial healing response. When circumferential radial forces are applied to the vasculature, as in the case of angioplasty or stenting, the plaque mass is displaced, forcing the vessel wall to stretch dramatically. This stretch injury is a known stimulus for the cellular in-growth that leads to restenosis. By using atherectomy to remove the disease with minimal force applied to the vessel, large gains in lumen size can be created with decreased vessel wall injury and limited elastic recoiling. These effects have been shown to generate better acute results and lower restenosis rates.

Despite its advantages, atherectomy is not commonly performed due to the cost, complexity and limited applicability of available atherectomy devices. Many designs are unable to treat the wide range of disease states present in long complex lesions; luminal gain is often limited by the requirement of the physician to introduce multiple devices with increased crossing profiles; tissue collection is either unpredictable or considered unnecessary based on assumptions regarding small particle size and volumes; and optimal debulking is either not possible due to a lack of intravascular visualization or requires very long procedure times. Based on these limitations, current devices are likely to perform poorly in the coronary vasculature where safety and efficacy in de novo lesions, ostials, and bifurcations continue to pose great challenges.

In the past, atherectomy devices have focused on macerating or emulsifying the atherosclerotic plaque such that either it might be considered clinically insignificant enough to remain in the blood stream or that it can be aspirated proximally through small spaces in the catheter main body. When the plaque is not aspirated through the catheter to an external reservoir, the reliability of these devices to produce clinically insignificant embolization has been challenged. Aspiration necessitates that a vacuum be applied to a lumen or annular space within the catheter to remove emulsified tissue. In early clinical evaluations of aspiration, the presence of negative pressure at the distal working assembly caused the artery to collapse around the cutting element. This effect results in more aggressive treatment, dissections and/or perforations. In addition, options for post-procedural analysis of any removed disease are extremely limited or impossible using this methodology.

Other atherectomy devices include directional atherectomy devices, which use cup-shaped cutters that cut and "turn" the tissue distally into a storage reservoir in the distal tip of the device. This approach preserves the "as cut" nature of the plaque, but requires large distal collection elements. These large distal tip assemblies can limit the capability of the system to access small lesions and may cause additional trauma to the vessel.

Currently available atherectomy devices also do not include, and are poorly adapted for use with, real time image guidance. Although intravascular diagnostic devices have consistently shown lesions that are significantly eccentric, the typical practice of physicians is to treat target lesions as if they contain concentric disease. This circumferential treatment approach virtually ensures that potentially native arterial wall and healthy vessel will be cut from the vasculature.

Further, several design challenges are presented by a single use, disposable, and single-direction imaging catheter, such as an atherectomy catheter. For example, obtaining a clear image can be difficult, as nonuniform rotational distortion ("NURD") can occur in the image as a result of the cutter vibrating or stalling as it encounters different types of tissue. Moreover, the imaging fiber, which runs from the static light source to the rotating distal tip, can become wound up as the catheter is in active (cutting) mode. Further, a motor can be required to drive the imaging assembly at the appropriate revolution rates for imaging, thereby significantly increasing the cost and complexity of the catheter.

Atherectomy catheter devices, systems and methods that may address some of these concerns are described and illustrated below.

SUMMARY OF THE DISCLOSURE

Described herein are atherectomy catheters with on-board imaging, systems including the atherectomy catheters, and methods of using the atherectomy catheters and systems.

In general, in one embodiment, an atherectomy catheter includes an elongate flexible catheter body, a cutter near the distal end of the catheter body, a drive shaft connected to the cutter and extending within the catheter body, an imaging element near the distal end of the catheter body and an imaging shaft connected to the imaging element and extending within the catheter body. The cutter and the imaging element are mechanically isolated, and the drive shaft is configured to be axially translated relative to the imaging shaft and the catheter body.

This and other embodiments can include one or more of the following features. The drive shaft and imaging shaft can be decoupled along the length of the catheter body. The drive shaft and imaging shaft can be coupled at a proximal end of the device. The atherectomy catheter can include a handle configured to transmit torque simultaneously to the proximal end of the drive shaft and the imaging shaft, and the drive shaft and imaging shaft can be coupled within the handle. The handle can include a translation mechanism configured to translate the drive shaft without translating the imaging shaft. The atherectomy catheter can include an inflatable element configured to urge the cutter against a vessel wall. The atherectomy catheter can include an elongate distal tip connected to the catheter body, and the elongate distal tip can include a cutting window therein, the cutting window sized and dimensioned so as to cause tissue to invaginate within the cutting window. The imaging element can include an optical fiber, and the optical fiber can be coupled to the imaging shaft only at a distal end of the imaging shaft. The imaging element can include an optical coherence tomography imaging element. The drive shaft and imaging shaft can be concentric, and the drive shaft can extend within the imaging shaft. The drive shaft and the imaging shaft both can extend substantially along a central axis of the catheter body. The imaging element can include an optical fiber, and the optical fiber can extend off-axis along the length of the catheter body. The optical fiber can be configured to rotate within the imaging shaft without wrapping around the drive shaft. The drive shaft and imaging shaft can be parallel. The imaging shaft can extend off-axis relative to the elongate body. The drive shaft can extend on-axis relative to the elongate body. The atherectomy catheter can include a handle configured to transmit torque simultaneously to the proximal end of the drive shaft and the imaging shaft. The handle further can include a rotation knob configured to allow rotation of the elongate body up to three rotations. The knob can include a rotation limiter, the rotation limiter can be configured to allow rotation of up to a set amount between one and three rotations while not lengthening the elongate body. The drive shaft and imaging shaft can be concentric, and the imaging shaft can extend within the drive shaft. A distal end of the drive shaft can include a clear annular portion connected to the cutter. The imaging element can be configured to be axially aligned with the clear annular portion for imaging. The clear annular portion can include sapphire, polycarbonate, glass, or acrylic.

In general, in one embodiment, an atherectomy catheter includes an elongate flexible catheter body. The atherectomy catheter includes a drive shaft extending within the catheter body, the drive shaft having a cutter attached thereto. The atherectomy catheter includes an elongate distal tip connected to the catheter body at a hinge point. The atherectomy catheter includes an inflatable body linked to the elongate flexible catheter body and to the elongate distal tip such that inflation of the inflatable body axially deflects the elongate distal tip away from the elongate flexible catheter body at the hinge point to expose the cutter. The inflatable body is linked to the elongated flexible catheter body and the elongated distal tip with a sling extending along an outer surface of the balloon and attached to the elongated flexible catheter body and the elongate distal tip.

This and other embodiments can include one or more of the following features. The atherectomy catheter can include a biasing mechanism configured to return the elongate distal tip to a position approximately axially aligned with the catheter body. The biasing mechanism can include a wedge activated by placing axial force on the drive shaft. The elongate distal tip can include a cutting window therein, and the cutting window can have an asymmetric shape configured to prevent the cutter from hitting a distal edge of the cutting window. The atherectomy catheter can include an imaging element attached to the cutter and configured to rotate therewith. The imaging element can be an optical coherence tomography imaging element. The imaging element can include an optical fiber, and the optical fiber can extend through the drive shaft substantially on-axis with the catheter body.

In general, in one embodiment, an atherectomy assembly includes an elongate flexible catheter body. The atherectomy assembly includes a drive shaft extending within the catheter body. The drive shaft has a rotatable cutter attached thereto and is axially movable with respect to the elongate flexible catheter body. The atherectomy assembly includes an optical fiber attached to the cutter and configured to rotate therewith. The atherectomy assembly includes a handle having a distal end attached to the elongate body and a proximal end configured to connect the optical fiber to a light source. The handle is configured such the optical fiber is axially movable with respect to the distal end and axially fixed with respect to the proximal end.

This and other embodiments can include one or more of the following features. The handle can include a tube within which the optical fiber can reside. The optical fiber can be configured to wind within the tube. The tube can be shaped as a ring, and the optical fiber can be configured to conform to an outer perimeter of the tube when in a compressed configuration and to conform to an inner perimeter of the tube when in an extended configuration. The optical fiber can be configured to transmit an optical coherence tomography signal.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 1A is an outer view of the device with the cutter in a proximal (cutting) position. FIB. 1B is a cross-section of the device of FIG. 1A. FIG. 1C shows the device with the inflatable element in an expanded configuration.

FIG. 2A is an external view of the handle. FIG. 2B shows a view of the handle of FIG. 2A with the outer shell removed. FIG. 2C shows a close-up of the handle with the drive bridge removed.

FIG. 3A is an outer view of the device with the cutter in a proximal (cutting) position. FIG. 3B is a cross-section of the device of FIG. 3A. FIG. 3C is a cross-section through the outer shaft of the device of FIG.

3A. FIG. 3D shows the inflatable element of the device. FIG. 3E shows a close-up view of the imaging portion of the device.

FIG. 4A shows the breakout port of the handle for management of the drive shaft, imaging shaft, and balloon inflation lumen. FIG. 4B shows is a diagram of the handle components.

FIGS. 5A-5F show a knob configured to rotate the outer shaft of the catheter of FIGS. 3A-3E up to a set number of rotations without lengthening the device. FIG. 5A shows the inner portions of the knob. FIG. 5B show the inner portions of the knob with the spiral track in transparent. FIG. 5C shows the inner portions with a sleeve in transparent. FIG. 5D shows the inner portions and sleeve with an outer portion in transparent. FIG. 5E shows the inner portions with a slide in transparent that is in the proximal-most position. FIG. 5F shows the inner portions with a slide in transparent that is in the distal-most position.

FIG. 6A shows a variation of a distal end of an atherectomy catheter with the nosecone in a closed position. FIG. 6B shows a variation of a distal end of the atherectomy catheter with the nosecone in an open position. This embodiment includes a balloon mechanism configured to open the nosecone when the balloon is inflated.

FIG. 6C shows the activation mechanism in an open position. FIG. 6D shows the activation mechanism in a closed position.

FIGS. 8A-8B show a first embodiment of a handle configured such that the inner drive shaft can be extended axially at the distal end without requiring axial movement of the drive shaft at the proximal end. FIG. 8A shows the drive shaft in the compressed configuration. FIG. 8B shows the drive shaft in the extended configuration.

FIG. 9A shows the drive shaft in the compressed configuration.

FIG. 9B shows the drive shaft in the extended configuration.

FIG. 13A is an outer view of the device. FIG. 13B includes a transparent outer shaft and nosecone so as to show the drive shaft and imaging element therein. FIG. 13C shows the drive shaft and cutter in an extended (distal) packing position. FIG. 13D is a cross-section of the device.

DETAILED DESCRIPTION

Described herein are atherectomy catheters. In general, the atherectomy catheters can include a rotatable cutter connected to a drive shaft. Further, the atherectomy catheters can include on-board imaging, such as optical coherence tomography (OCT) imaging. The atherectomy catheters can include a distal housing (nosecone) configured to hold excised tissue. The drive shaft can be moved distally to pack the excised tissue into the nosecone.

In some embodiments, the atherectomy devices described herein can include an inflatable element configured to urge the cutter against the vessel wall. In some embodiments, the inflatable element can activate a hinge mechanism to hinge the nosecone off-axis with the catheter body, thereby exposing the cutter. In such embodiments, a biasing mechanism, such as a wedge, can optionally be used to realign the nosecone and the catheter body. In other embodiments, the inflatable element can urge the cutter against the vessel wall without a separate hinge mechanism. In such embodiments, the cutting window in the catheter can be sized so as to allow the tissue to invaginate within the cutting window and be excised by the rotatable cutter.

In some embodiments, the atherectomy devices described herein can be configured such that the imaging element and the cutter are driven by the same shaft. In other embodiments, there can be a separate imaging shaft and a separate drive shaft to separately control the distal rotation of the imaging element and the cutter, thereby advantageously reducing or eliminating nonuniform rotational distortion (NURD) in the resulting image. In such embodiments, the imaging and drive shafts can be driven by the same rotational mechanism at the proximal end. In such embodiments, the drive shaft and cutter can further advantageously be translated axially without requiring translation of the imaging shaft and imaging element.

Handles are also described herein for use with atherectomy devices. In some embodiments, the handle is configured to rotate an imaging shaft and a drive shaft concurrently while providing axial translation of only the drive shaft. In other embodiments, the handle is configured to provide axial movement of an optical fiber (with a drive shaft) at a distal end of the handle but not the proximal end of the handle.

FIGS. 1A-5F and 13A-14 show examples of atherectomy devices and handles having drive and imaging shafts that are separated from one another at the distal end and translatable relative to one another. FIGS. 1A-5F and 13A-14 also have cutters that are configured to be urged against the vessel wall with an inflatable element without using a separate hinge mechanism.

Figure 1A:
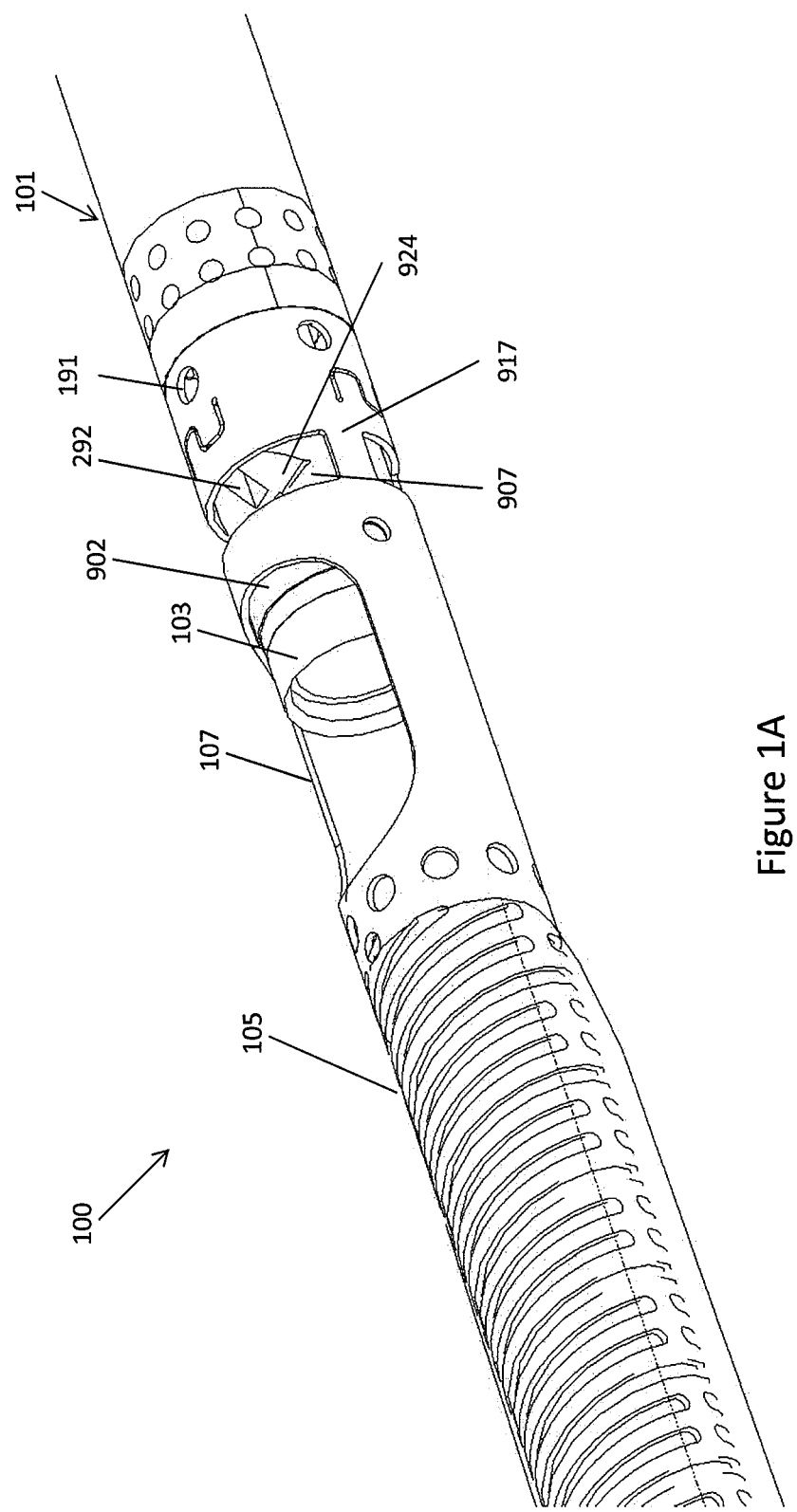
FIGS. 1A-1C show an atherectomy device having concentric drive and imaging shafts that are separated from one another at the distal end and axially translatable relative to one another.
Figure 1B:
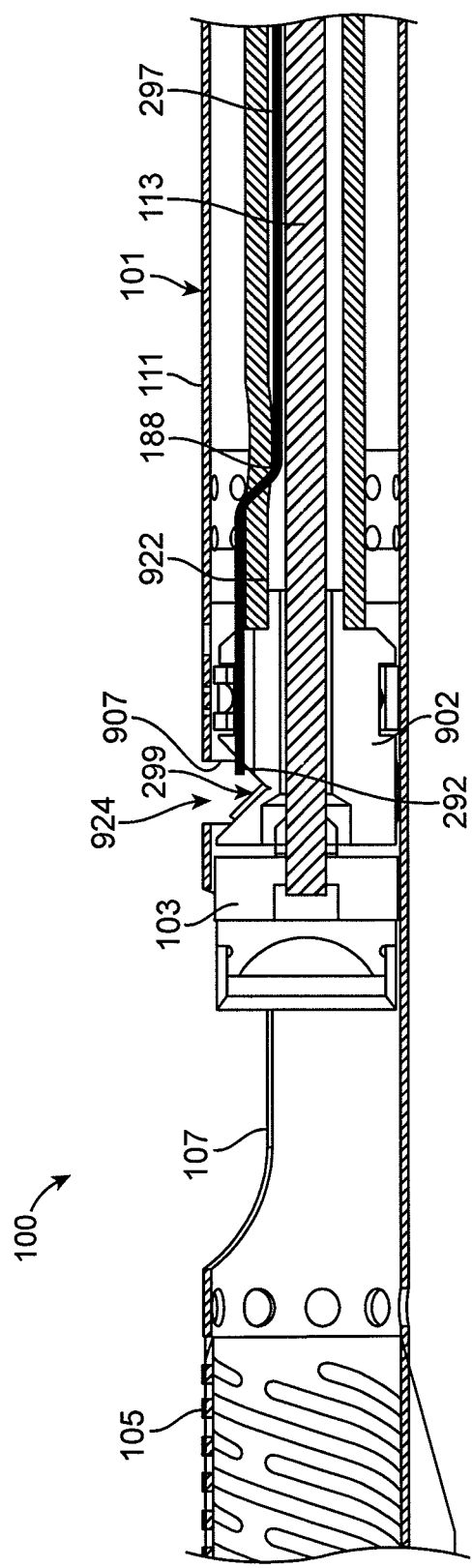
Figure 1C:
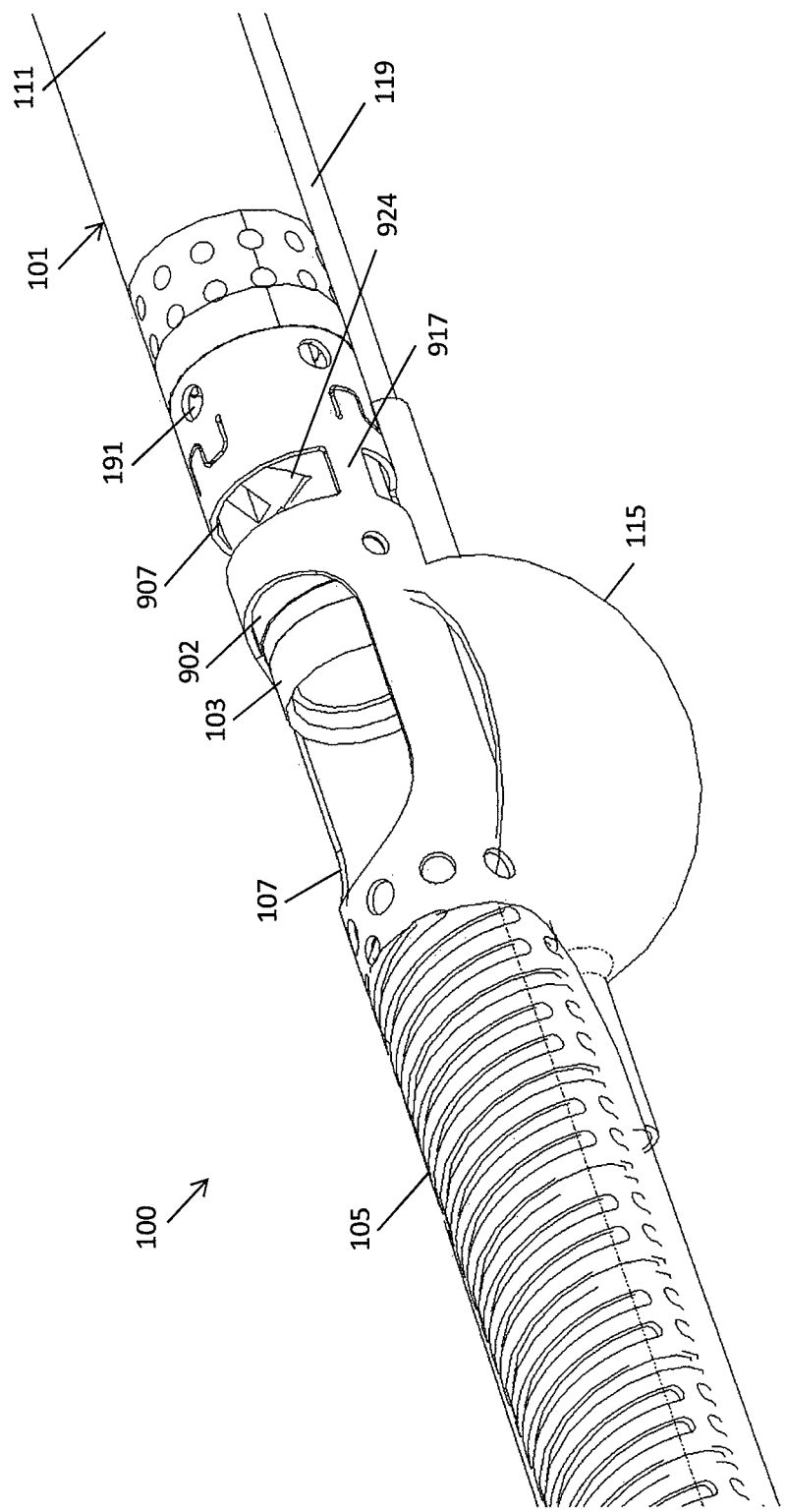

In one embodiment, referring to FIGS. 1A-1C, a catheter 100 can include a catheter body 101, a cutter 103 extending from the distal end of the catheter body 101, and an imaging collar 902 near the distal end of the catheter body 101 but proximal to the cutter 103. A nosecone 105 can extend from the distal end of the catheter body and around the cutter 103 to store tissue removed by the cutter 103. The nosecone 105 can include a cutting window 107 therein configured to expose a portion of the cutter 103. The catheter 100 can further include an inflatable element, such as a balloon 115 (see FIG. 1C), configured to urge the cutter 103 against the side of a vessel.

Referring to FIG. 1B, the catheter body 101 can include an outer shaft 111 and a drive shaft 113 extending inside the outer shaft 111. The outer shaft 111 can be configured to be turned, such as turned manually, to position the cutter 103 and/or the imaging collar 902 toward the desired location. The drive shaft 113 can extend through, and rotate relative to, the imaging collar 902. Further, the drive shaft 113 can be attached to the cutter 103 to rotate the cutter 103. Rotation of the cutter 103 can provide cutting due to the rotational motion of the sharp distal cutting edge. The drive shaft 113 can be rotated at up to 10,000 rpm, such as approximately 1,000 rpm to 5,000 rpm, e.g., 1,000 rpm, in a single direction, though rotation in both directions or at different speeds is possible.

Referring still to FIG. 1B, the catheter 100 can further include an optical fiber 297, the distal end of which can act as an imaging element 292 for OCT imaging. The imaging collar 902 can be attached to an imaging shaft 922 that extends within the catheter body 101 concentric with the drive shaft 113. As shown in FIG. 1B, the concentric imaging shaft 922 can extend between the drive shaft 113 and the outer shaft 111 (i.e. such that the drive shaft 113 is in the center). In other embodiments (such as described below with respect to FIGS. 13A-D), the drive shaft 113 can extend between the concentric imaging shaft 922 and the outer shaft 111 (i.e. such that the imaging shaft 922 is in the center). The rotation of the imaging shaft 922 and the drive shaft 113 can be decoupled from one another at the distal end of the device, thereby providing for separate rotation of the cutter 103 and the imaging element 292 (which can be the distal end of an optical fiber 297). As described below, in some embodiments, the rotation of the imaging shaft 922 and the drive shaft 113 can be coupled at the proximal end (such as in the handle so as to be driven by the same motor) while remaining decoupled along the length of the catheter.

The outer shaft 111 (or a housing connecting the outer shaft 111 to the nosecone 105) can include an imaging window 907 through which the imaging element 292 can be exposed. The imaging window 907 can extend 360 degrees around the circumference of the outer shaft 111, but can include structural struts 917 extending thereacross to both provide structural support and act as imaging markers. The imaging window 907 can further be used as a flush port to allow flush fluid to be delivered through the outer shaft 111 and to the area of imaging, thereby improving image quality. In some embodiments, flush fluid can extend through fluid ports 191 in the outer shaft 111.

The optical fiber 297 can run within the imaging shaft 922 to provide the imaging (e.g., OCT) signal. As shown in FIG. 1B, the optical fiber 297 can run between the inner diameter of the imaging shaft 922 and the outer diameter of the drive shaft 113 and can be free to flow therein. At distal point 188, the fiber 297 can cross to the outside of the imaging shaft 922 to attach to the imaging collar 902, such as in an opening 924 in the imaging collar 902. Leaving the optical fiber 297 free to float within the imaging shaft 922 for the majority of the length of the catheter body 101 ensures that the fiber is not compressed or stretched as the catheter 100 bends as it is advanced through tortuous anatomy. As described further below, the fiber 297 can be rotated with the imaging shaft at both the proximal and distal ends of the fiber 297. Accordingly, the fiber 297 does not have to wrap around the drive shaft 113 as it rotates, advantageously both reducing the likelihood of fiber breakage and allowing the imaging element and cutter to rotate in a single direction.

As shown in FIG. 1B, a reflective element 299, such as a mirror, a polished pin, a film deposited on the surface of the imaging collar 902, or a polished surface of the imaging collar 902 itself, can further be located within the opening 924 in the imaging collar 902 to radially direct light from the optical fiber 297 into the tissue. The reflective element 299 can sit, for example, at a 35 degree to 55 degree angle, such as a 45 degree angle, relative to the central axis of the optical fiber 297 so as to direct the light sideways into the tissue. The distal end of the optical fiber 297 can be located less than 3 mm from the distal edge of the cutter 103, such as less than 1.5 mm from the cutting edge, such as less than or equal to 1.2 mm, such as less than or equal to 1 mm. By having the imaging element 292 close to the cutting edge, the resulting image can advantageously correlate with and depict the portions of the vessel being cut.

As shown in FIG. 1C, an inflatable element, such as a balloon 115, can be located opposite to the cutting window 107. Referring to FIG. 1C, the balloon 115 can be attached to an inflation tube 119, which can alongside or be embedded in the outer shaft 111. The balloon 115 can be attached at the distal end to the outer shaft 111 (at a location just proximal to the imaging window 907) and at the proximal end to the inflation tube 119 inside the outer shaft 111, such as through a hole in the outer shaft 111. In some embodiments, the inflation tube 119 can radially align with one or more of the struts 917 so as to not hinder the resulting image. Inflation of the balloon can position or urge the cutting window 107 and thus the cutter against the tissue. Further, the cutting window can be sized and dimensioned such that inflation of the balloon 115 causes the tissue to invaginate within the cutting window, thereby improving the cutting quality of the device. Further, the cutting window can be sized such that it is smaller than the diameter of the cutter, thereby preventing the cutter from popping out as the cutting window and cutter are urged against the vessel wall. In one embodiment, the window 107 can extend between 90 and 270 degrees around the circumference of the nosecone or catheter, such as 150 to 210 degrees, such as between 175 and 180 degrees. Having a window 107 of these dimensions, such as that extends 175 and 180 degrees around the circumference of the nosecone or catheter, can advantageously provide significant tissue capture upon inflation of the balloon 115 while still providing adequate stiffness to the nosecone or catheter.

The catheter 100 can further include a mechanism for packing tissue into the nosecone 105, such as by moving the drive shaft 113 and cutter 103 axially such that tissue can be urged by the distal surface of the cutter 103. Advantageously, the drive shaft 113 can be moved axially without movement of the imaging shaft 922, thereby allowing for packing of the tissue without disrupting the imaging.

Advantageously, by having an imaging shaft that is separate or decoupled from the drive shaft at their respective distal ends, the rotation of the cutter and the optical fiber can be mechanically isolated from one another (i.e., such that a mechanical action or reaction of one does not affect the other). For example, if the cutter stalls during rotation, such as when it hits a hard piece of tissue, the mechanically isolated imaging element can remain unaffected and continue rotating at the same constant speed. Such continuous rotation of the imaging element reduces or eliminates rotational distortion, such as nonuniform rotational distortion (NURD), thereby improving imaging quality.

Further, by having separate imaging and drive shafts, the drive shaft can advantageously be used to pack tissue while maintaining the imaging element in the same location, thereby ensuring that the imaging location is constant and well known. Moreover, by having separate imaging and drive shafts, the fluid flush can be delivered close to the imaging element even when the drive shaft is moved distally to pack tissue.

Further, by using the balloon 115 of catheter 100 to urge the cutter against the vessel wall and by having an optimally designed cutting window, tissue can be pressed into the cutting window and cut, thereby improving cutting quality without requiring an articulation mechanism in the catheter. Further, the balloon 115 can advantageously act as an occlusion element to restrict blood flow to the imaging element 292, thereby reducing the amount of saline flush required to obtain a clear image and improving image quality.

As noted above, in some embodiments, the drive shaft 113 and imaging shaft 922 can be unconnected at the distal end of the catheter to allow for separate imaging and cutting but connected at the proximal end of the catheter so that they can be rotated from the same source, such as the same drive system. Although the shafts can be connected at the proximal end of the cutter, rotational distortion can still be avoided because the rotating motor can be strong enough to spin at the same speed regardless of the resistance to rotation placed on the cutter at the distal end. Accordingly, even if the drive shaft slows down due to stalling, the imaging shaft can continue to rotate at the same constant input speed.

Referring to FIGS. 2A-2D, the catheter 100 can be used with a handle 200 configured such that the drive shaft 113 and the imaging shaft 922 can be rotated separately at the distal end of the catheter while being rotated with the same source at the proximal end of the catheter. Rotation with the same source can advantageously requires only one motor (reducing the size and complexity of the device), allows for the fiber to stay on the centerline of the catheter and handle, and can provide the same relative speed for zero relative speed between the imaging and drive shafts in aid in preserving imaging fiber integrity. As described further below, the handle 200 can further include a mechanism that allows for axial translation of the drive shaft 113 (e.g., to pack tissue with the cutter), but maintains the fixed position of the imaging shaft 922. Further, the handle 200 can be configured to as to allow free rotation of the fiber 297 therein such that minimal or no fiber management and/or wrapping of the fiber is necessary.

Figure 2A:
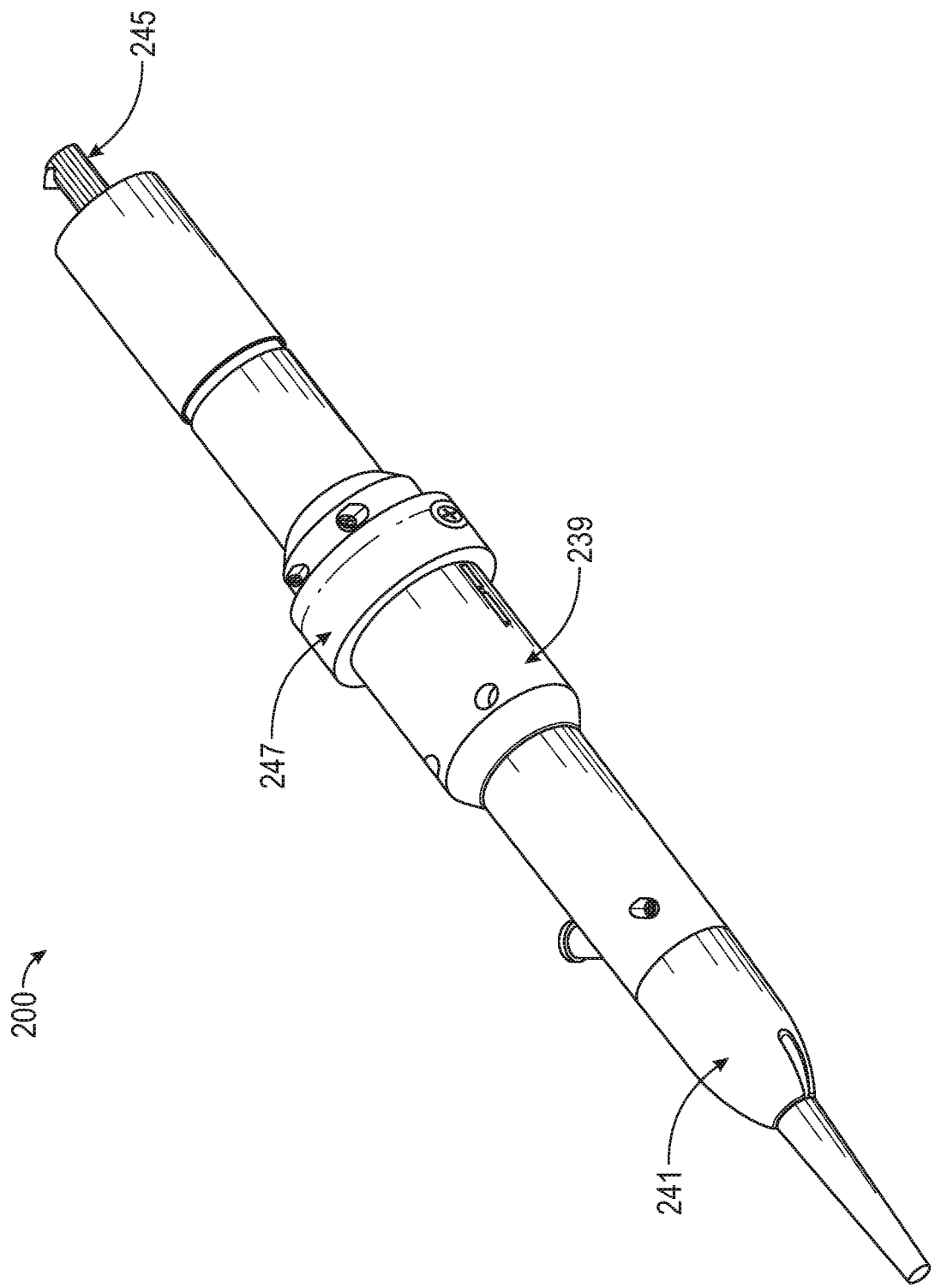
FIGS. 2A-2D show a handle for use with the atherectomy device of FIGS. 1A-1C.

Referring to FIG. 2A, the handle 200 can include an outer shell 239, a handle tip 241 configured to connect to the outer shaft 111 of the catheter 100, and an optical connector 245 configured to engage with a drive system and light source. The handle 200 can further include a handle ring 247 configured to slide along the handle 200 to translate the drive shaft 113 axially. The handle tip 241 can be configured to rotate relative to the rest of the handle 200 to allow the user to torque the outer shaft 111 to orient the distal tip of the catheter 100 in the desired position.

Figure 2B:
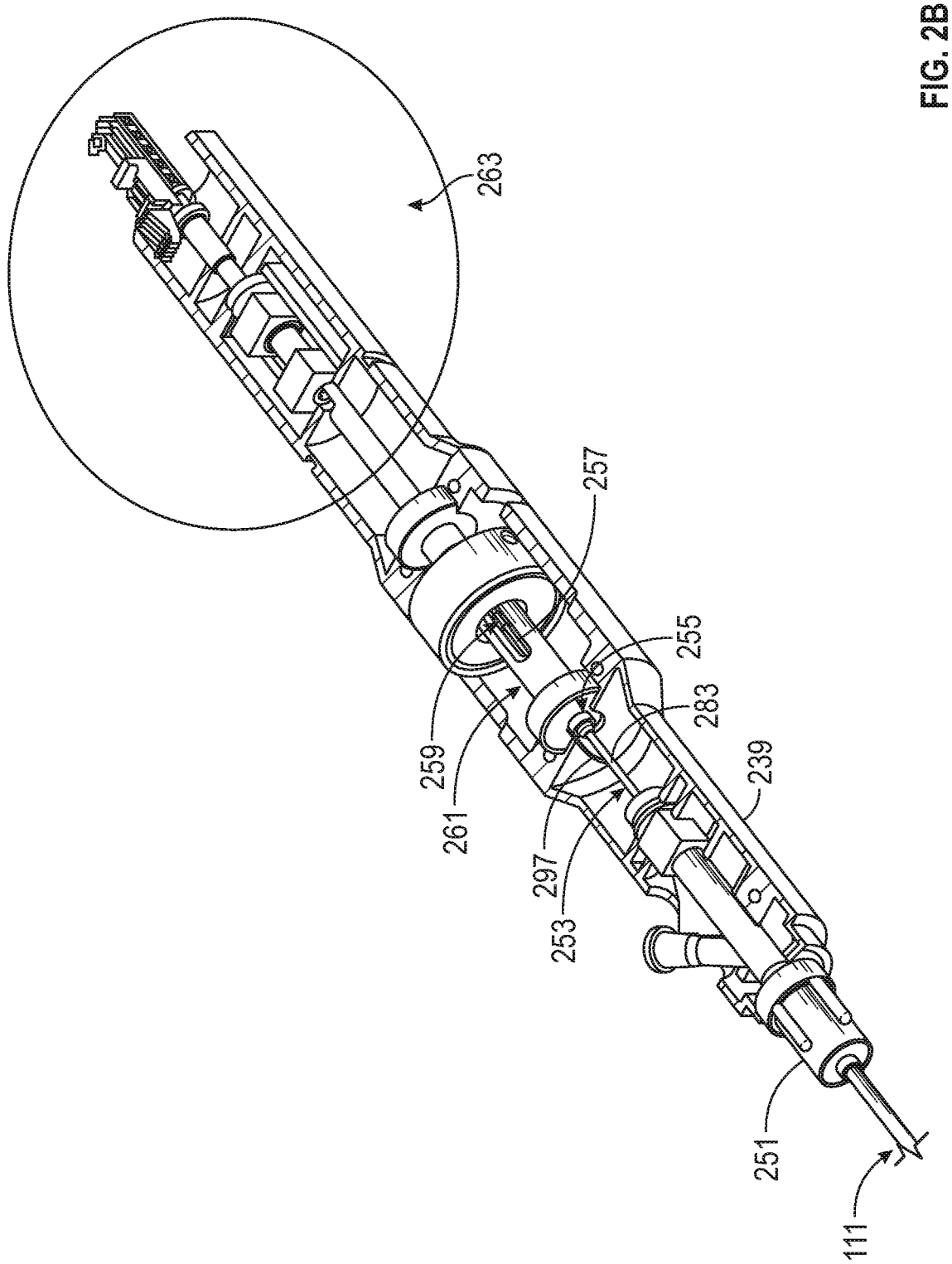

Referring to FIG. 2B, the proximal end of the catheter outer shaft 111 can be connected to a rotation mechanism 251 at the distal end of the catheter. The proximal end of the imaging shaft 922 can be connected to an imaging shaft hypotube 253 attached to an imaging shaft coupler 255. The proximal end of the drive shaft 113 can be attached to a drive shaft hypotube 257 that is attached to a drive shaft coupler 259. The hypotubes can telescope with respect to one another, thereby allowing for translation of the drive shaft within the imaging shaft, and can be configured to transmit torque and provide a fluid seal.

Figure 2C:
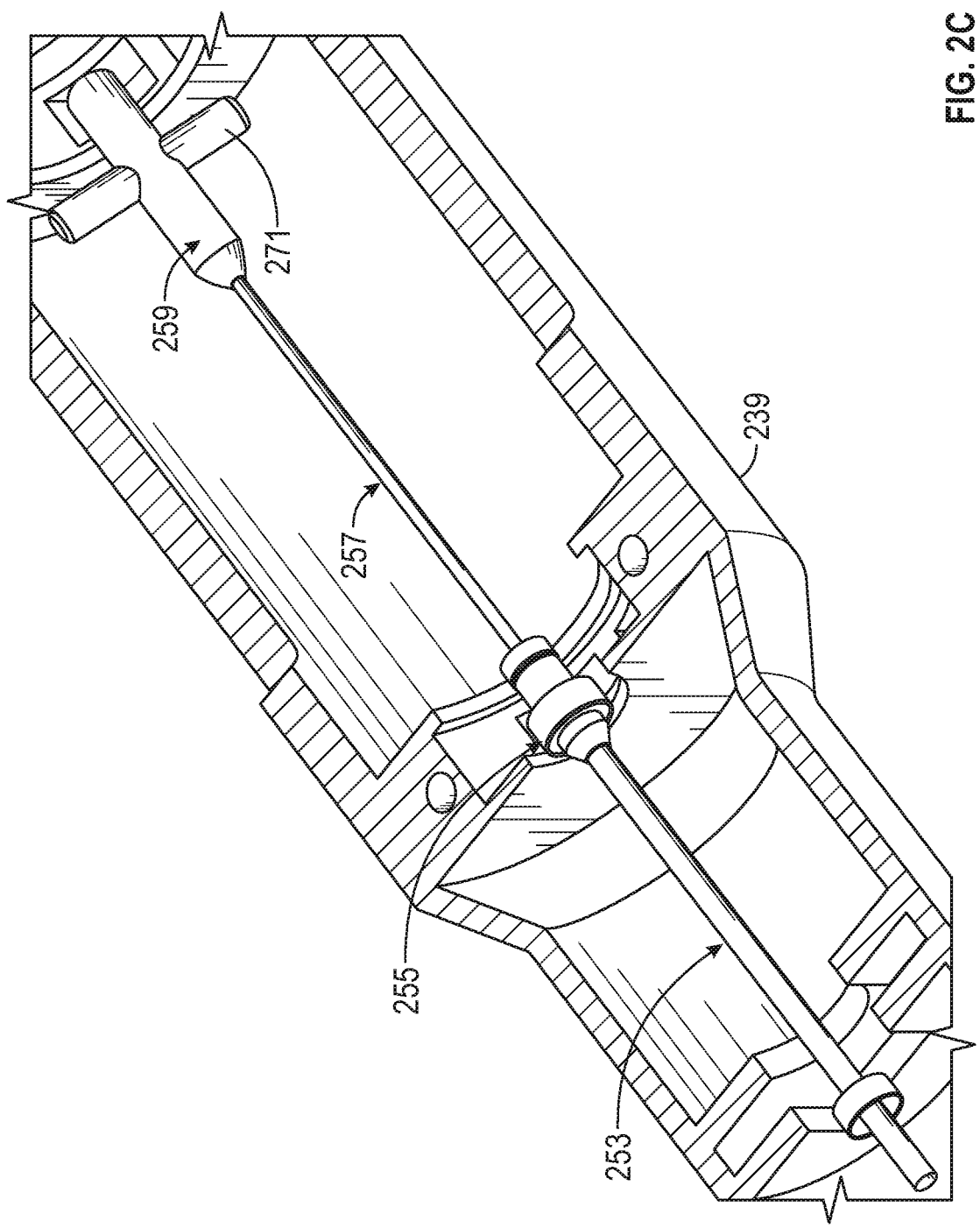
Figure 2D:
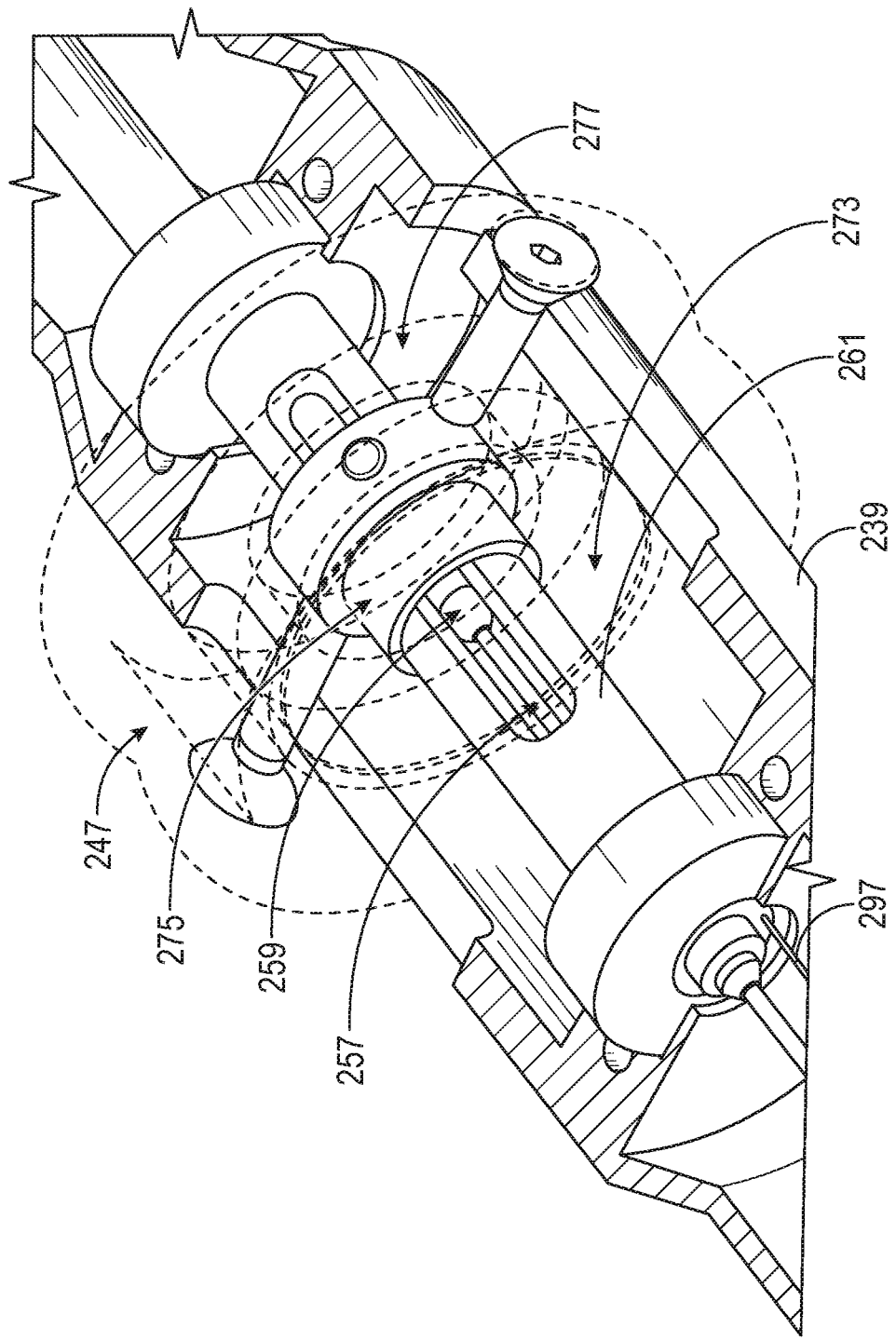

Referring to FIGS. 2B-2D, the imaging shaft coupler 255 can be attached to a drive bridge 261, which is in turn rotationally attached to the drive shaft coupler 259 (which extends within and concentric with the drive shaft bridge 261) through a pin 271. The drive bridge 261 is then attached to the proximal optical subassembly, which is configured to impart rotation thereto (thereby causing rotating of both the drive shaft 113 and the imaging shaft 922), such as via a drive system.

Referring to FIG. 2D, a bearing 273 extends within the handle 200. The bearing 273 engages, with its inner race, a drivebridge coupler 275 that is connected to the drive bridge 261. This connection allows the drivebridge coupler 275 (and drivebridge 261) to rotate within the bearing 273. The bearing 273 further engages, with its outer race, a handle ring coupler 277 connected to the handle ring 247 where the outer race of the bearing 273, the handle ring coupler 277, and the handle ring 247 do not rotate relative to the handle 200. This engagement allows the bearing, and thus the drive bridge coupler, the drive shaft coupler, and the drive shaft hypotube to rotate relative to the handle 200. Moreover, the engagement still allows the drive bridge coupler, the drive shaft coupler, and the drive shaft hypotube to translate proximally or distally when the handle ring is 247 is translated proximally or distally as desired by the user.

As shown in FIGS. 2B and 2D, the optical fiber 297 can be configured to extend out of the imaging shaft hypotube 253 at a point 283 just distal to the drive bridge 261. The optical fiber 297 can then traverse along the outer surface of the drive bridge 261, such as within a groove in the drive bridge 261, until it reaches the proximal optical assembly 263, where it can connect to light source. Accordingly, while the drive shaft coupler 259 and drive bridge 261, and thus the drive shaft 113, can move proximally and distally, the optical fiber 297 can remain at a fixed axial position. Having the axial fiber in a fixed axial position advantageously avoids requiring additional length of fiber 297 and/or placing unnecessary tension on the fiber 297. Further, by having the optical fiber 297 traverse along a groove in the outer surface of the drive bridge, the fiber 297 can rotate with the drive bridge 261. Rotating of the fiber with the drive bridge 261 ensures that the fiber maintains a clear path as it is rotated, i.e., such that it is not required to wrap around anything within the handle. Thus, as the imaging connection subassembly 263 is rotated by the drive system, the torque can be transmitted simultaneously through the imaging shaft 922, optical fiber 297, and drive shaft 113.

Handle 200 advantageously provides for rotation of the concentric imaging and drive shafts while allowing for axial movement of the drive shaft and not the imaging shaft or imaging fiber. The handle 200 can further advantageously be configured such that the optical fiber does not have to undergo any steep bends therein, thereby making the fiber more robust.

In some embodiments, rotation of the drive shaft and imaging shaft can be decoupled by, for example, using magnets in the handle to couple the input rotation with the drive shaft rotation. In such a configuration, the internal drive shaft can be rotated at a speed different than the imaging shaft without interrupting the rotation of the optical fiber. Rotating the imaging shaft at a different speed, or without, the drive shaft can advantageously allow for imaging with cutting and/or rotating at different speeds that are individually optimized for imaging and cutting.

Although described as being used with catheter 100, it is to be understood that the handle 200 and/or elements of the handle could be used with a variety of different catheters while still providing separate rotation of concentric imaging and drive shafts and/or axial movement of one or more shafts without axial movement of another.

FIGS. 13A-D show another example of an atherectomy catheter 1300 having drive and imaging shafts that are separated at the distal end and axially translatable relative to one another. The catheter 1300 is also configured to be urged against the vessel wall without a separate hinge mechanism. The catheter 1300 can include a catheter body 1301, a drive shaft 1313 extending inside an outer shaft 1311, and an imaging shaft 1322 extending through the drive shaft 1313 (e.g., such that the imaging shaft 1322 extends through the center of the device). The drive shaft can include a clear annular portion 1395 on the distal end thereof.

Figure 13A:
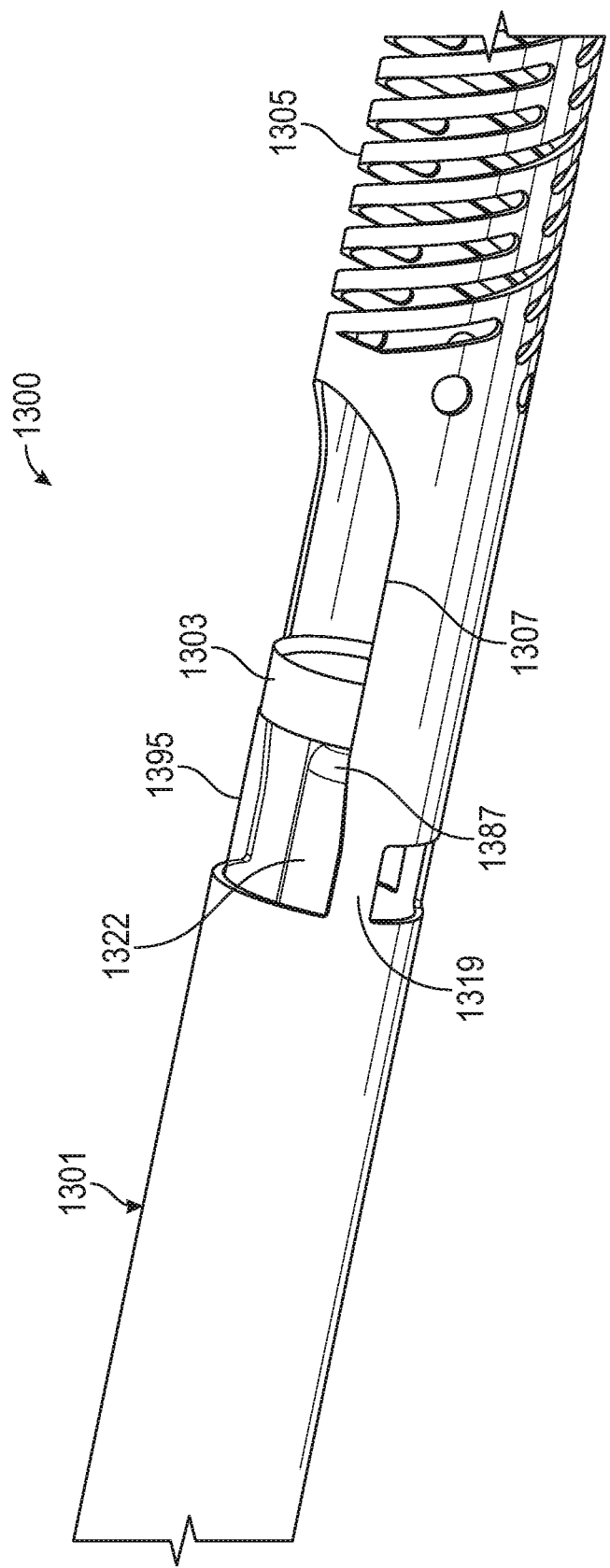
FIGS. 13A-D shows an atherectomy device having a drive shaft and a coaxial imaging shaft extending within the drive shaft. The drive shaft and imaging shafts are separated from one another at the distal end and axially translatable relative to one another.
Figure 13B:
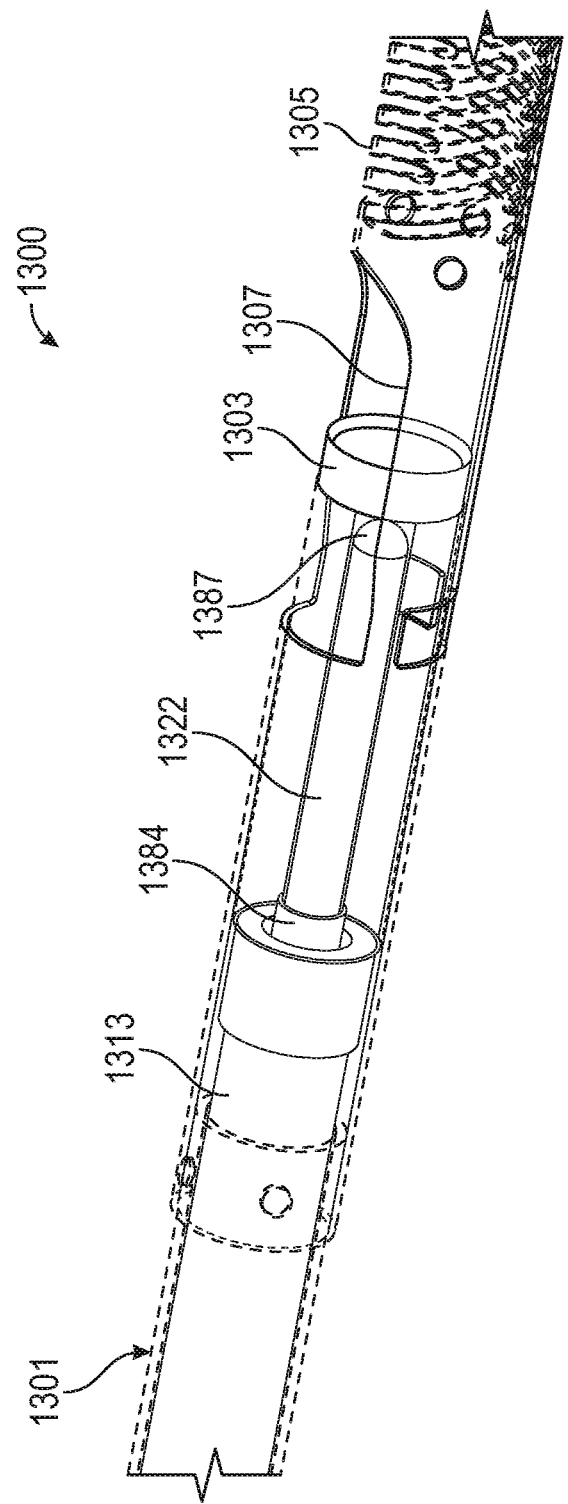
Figure 13C:
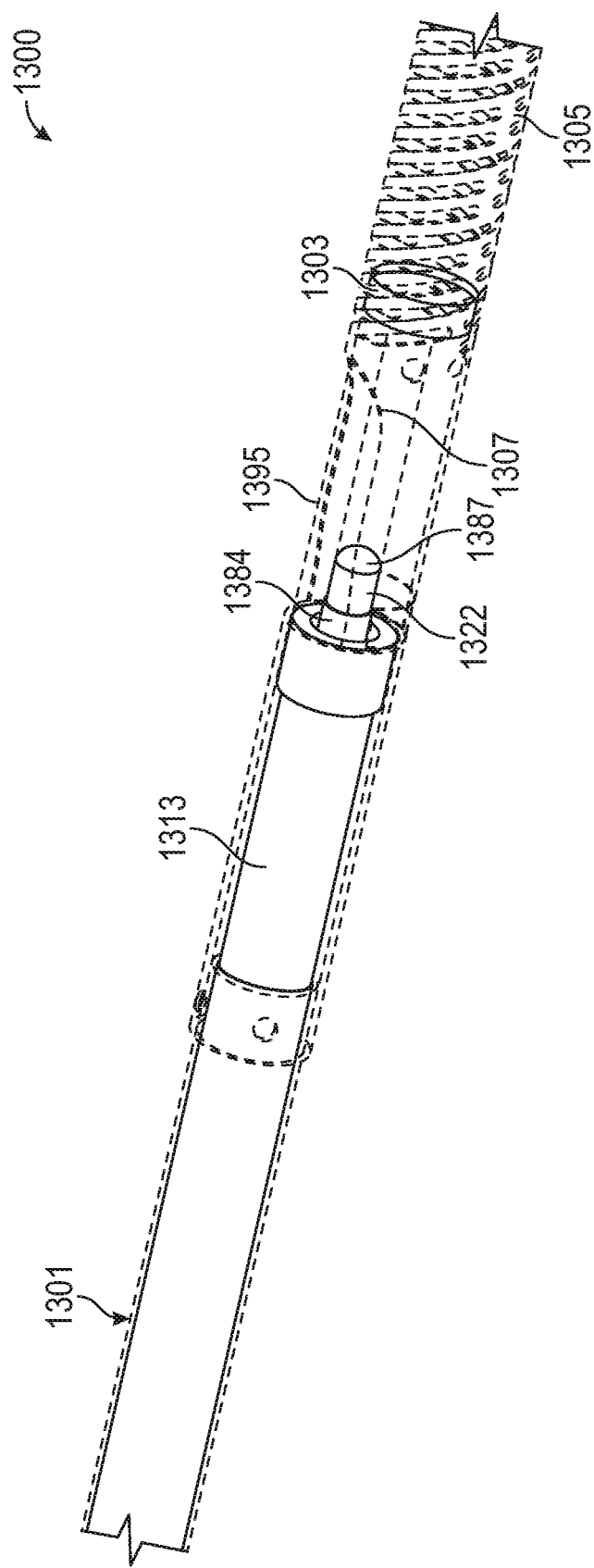
Figure 13D:
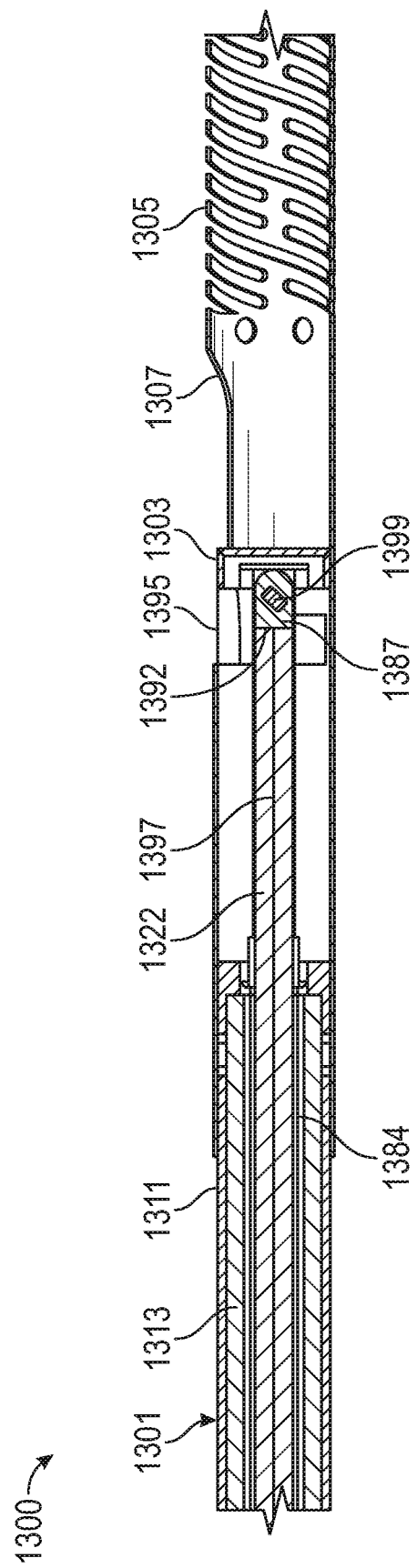

Referring to FIG. 13D, an optical fiber 1397 can extend through the center of the imaging shaft 1322 (and thus through the center of the catheter 1300) to provide the imaging (e.g., OCT) signal. The optical fiber 1397 can be attached at the distal end of the imaging shaft 1322 (such as in the bulb 1387, described below) but can be otherwise free to float within the imaging shaft 1322. The cutting window 1307 can also act as an imaging window through which the imaging element 1392 can be exposed. Similar to catheter 100, the window 1307 can include a structural struts 1319 therethrough to provide structure support and to act as imaging markers.

Referring still to FIG. 13D, the imaging shaft 1322 can end in a bulb 1387, which can be made, for example, of stainless steel. The bulb 1387 can have a window therein through which light from the optical fiber can be transmitted. The bulb 1387 can further include a glue in which the distal end of the optical fiber 297 us embedded. Further, in some embodiments, the bulb 1387 can house a reflective element 1399, which can be situated at an angle (such as 40-60 degrees, e.g., 45 degrees) relative to the fiber so as to direct light from the optical fiber out through the clear annular portion 1395. Light can thus travel through the optical fiber 1397, bounce off of the reflective element 1399, extend through the clear annular portion 1395, through the imaging window 1377, and into the tissue.

As noted above, the drive shaft 1313 can include a clear annular portion 1395 at the distal end thereof. The clear annular portion 1395 can advantageously keep blood away from the exit path of the OCT light beam while providing a window for the light beam to travel through. The clear annular portion 1395 can include an optically transparent material, such as sapphire, polycarbonate, glass, or acrylic. In some embodiments, material used for the clear annular portion 1395 can be substantially free of micro-defects that can cause light therein to scatter, as such scattering of light can reduce the amount of light transmitted to and from the tissue and reduce image quality. In some embodiments, the materials used for the clear annular portion 1395 can have a flat response between 1260 nm and 1380 nm, i.e., the optical transmission can be relative constant between the used wavelength. Having a flat response advantageously ensures that there is no interference with OCT signals, improving image quality.

In some embodiments, the refractive index of the clear annular portion 1395 can be similar to the refractive index of the glue in which the distal end of the optical fiber is embedded. For example, the refractive index of polycarbonate is low, such as between 1.584 and 1.586, which in some embodiments can be comparable to the refractive index of the glue attached to the fiber, such as Masterbond EP42HT-2, EpoTek OG127-4 or OG116, produced by Epoxy Technology and UV curable photonics adhesive OP-4-20658. Using a clear annular portion 1395 having a refractive index that is similar to the glue in which the distal end of the optical fiber is embedded advantageously reduces the back-reflection at the glue/annular portion interface, thereby increasing image quality. As another example, the refractive index of sapphire is high, such as about 1.78, which can result in a higher back-reflection of a glue with a low refractive index (such as those described above) is used (a higher mismatch between the refractive indices results in higher back-reflection). Accordingly, a glue with a higher mismatch can be used, such as NOA 1625 from Norland Optical adhesives.

In other embodiments, rather than matching the refractive indices of the glue and the clear annular portion 1395, the housing geometry could be modified such that the light beam hits the clear annular portion 1395 at an angle so that very little or none of the reflective light can be coupled back into the fiber. In other words, the mirror, glue, fiber, the clear optical portion can be configured such that the angle of incidence of light to the interface medium between the glue and the clear annular portion is close to the polarization angle (also called the Brewster's angle) wherein all of the light is transmitted with minimal reflection.

When the clear annular portion 1395 is used, the focal length of the OCT light beam can be extended to compensate for the additional material through which the light has to travel. To do so, the beam diameter at the waste can be increased or a fiber or GRIN fiber with a larger diameter can be used.

A cutter 1303, such as an annular cutter, can be attached to the clear annular portion 1395 of the drive shaft 1313. In some embodiments, the cutter can be carved out of the clear annular portion 1395. For example, if the material for the clear annular portion 1395 is strong, such as sapphire, then the cutter 1303 and clear annular portion 1395 can be made of the same piece. Having the cutter 1303 and clear annular portion 1395 be made of the same piece can advantageously allow the images to be generated from a location very close to the cutter 1303, helping to achieve more precise cutting.

Further, similar to the catheter 100, the catheter 1300 can include a nosecone 1305 extending from the distal end of the catheter body around the cutter 1303 to store tissue removed by the cutter 1303. The nosecone 1305 includes a cutting window 1307 therein configured to expose a portion of the cutter 1303. Similar to catheter 100, the catheter 1300 can further includes an inflatable element, such as a balloon, configured to urge the cutter 1303 against the side of a vessel (and can include a corresponding optimized cutting window 1307 for cutting tissue as described with respect to catheter 100).

The rotation of the imaging shaft 1322 and the drive shaft 1313 can be decoupled from one another at the distal end of the device, thereby providing for separate rotation of the cutter 1303 and the imaging element 1392. As described below, in some embodiments, the rotation of the imaging shaft 1322 and the drive shaft 1313 can be coupled at the proximal end (such as in the handle so as to be driven by the same motor) while remaining decoupled along the length of the catheter. In some embodiments, a separating layer 1384, such as a polyimide layer, can be placed between the drive shaft 1313 and the imaging shaft 1322. The separating layer 1374 can advantageously be used to prevent the transfer of energy between the drive shaft 1313 and the imaging shaft 1322 (for example, such that if the drive shaft 1313 gets bogged down while cutting, the chances of it affecting the imaging shaft 1322 will be reduced).

The catheter 1300 can include a mechanism for packing tissue into the nosecone 1305, such as by moving the drive shaft 1313 and cutter 1303 distally as shown in FIG. 13C. Advantageously, the drive shaft 113 can be moved axially without movement of the imaging shaft 122, thereby allowing for packing of the tissue without disrupting the imaging.

Similar to catheter 100, by having an imaging shaft that is separate or decoupled from the drive shaft at their respective distal ends, the rotation of the cutter and the optical fiber can be mechanically isolated from one another, imaging quality can be improved due to reduced NURD.

Further, by having separate imaging and drive shafts, the drive shaft can advantageously be used to pack tissue while maintaining the imaging element in the same location, thereby ensuring that the imaging location is constant and well known.

By placing the imaging element within the center of the catheter, the catheter can advantageously be reduced in size (for example, relative to a device where there is an annular space between an inner drive shaft and an outer imaging shaft). The catheter 1300 can thus be, for example, less than 8 French, such as 6-8 French, which can advantageously make the catheter 1300 useable in small diameter vessels, such as coronary vessels. Further, by placing the drive shaft around the imaging shaft, as in catheter 1300, the drive shaft can advantageously be larger and more robust, such as 0.05" to 0.06." In some embodiments, the drive shaft can include a multi-layer coil, which can also advantageously increase the robustness of the drive shaft, thereby providing a cutting system that is more resistant to stalling.

In some embodiments, the drive shaft 1313 and imaging shaft 1322 can be unconnected at the distal end of the catheter to allow for separate imaging and cutting but connected at the proximal end of the catheter so that they can be rotated from the same source, such as the same drive system. Although the shafts can be connected at the proximal end of the cutter, rotational distortion can still be avoided because the rotating motor can be strong enough to spin at the same speed regardless of the torque placed on the cutter at the distal end. Accordingly, even if the drive shaft slows down due to stalling, the imaging shaft can continue to rotate at the same constant speed.

Figure 14:
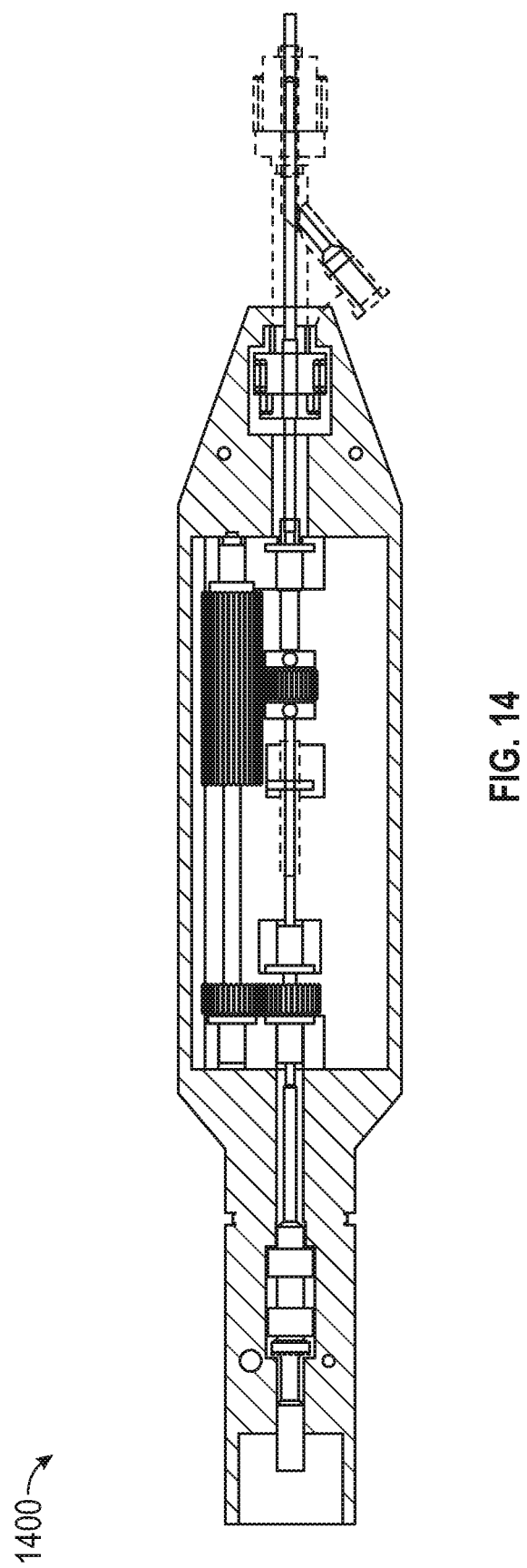
FIG. 14 is an exemplary handle for use with the atherectomy device of FIGS. 13A-D.

Referring to FIG. 14, the catheter 1300 can be used with a handle 1400 configured such that the drive shaft 1313 and the imaging shaft 1322 can be rotated separately at the distal end of the catheter while being rotated with the same source at the proximal end of the catheter. The handle 1400 can be configured similar to the handle 400 of FIGS. 4A-4B, described further below.

FIGS. 3A-E show another example of an atherectomy catheter 300 having drive and imaging shafts that are separated at the distal end and axially translatable relative to one another. The catheter 300 is also configured to be urged against the vessel wall without a separate hinge mechanism. The catheter 300 can include a catheter body 301, a cutter 303 extending from the distal end of the catheter body 301, and an imaging tip 308 near the distal end of the catheter body 301 but proximal to the cutter 303. A nosecone 305 can extend from the distal end of the catheter body and around the cutter 303 to store tissue removed by the cutter 303. The nosecone 305 can include a cutting window 307 therein configured to expose a portion of the cutter 303. The catheter 300 can further include an inflatable element, such as a balloon 315 (see FIG. 3D), configured to urge the cutter 303 against the side of a vessel.

Figure 3A:
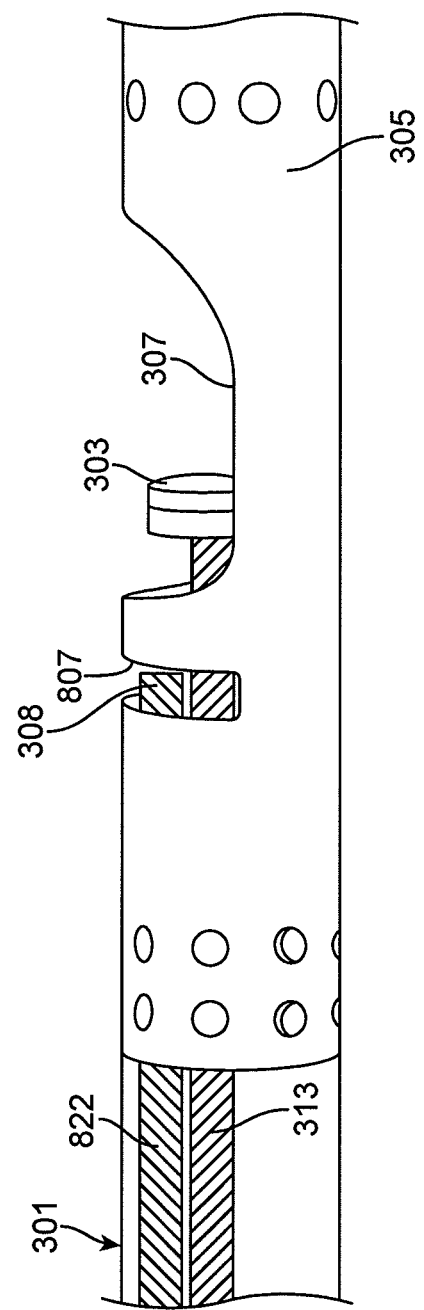
FIGS. 3A-3E show an atherectomy device having a drive shaft and a parallel imaging shaft extending alongside the drive shaft. The drive shaft and imaging shafts are separated from one another at the distal end and axially translatable relative to one another.
Figure 3B:
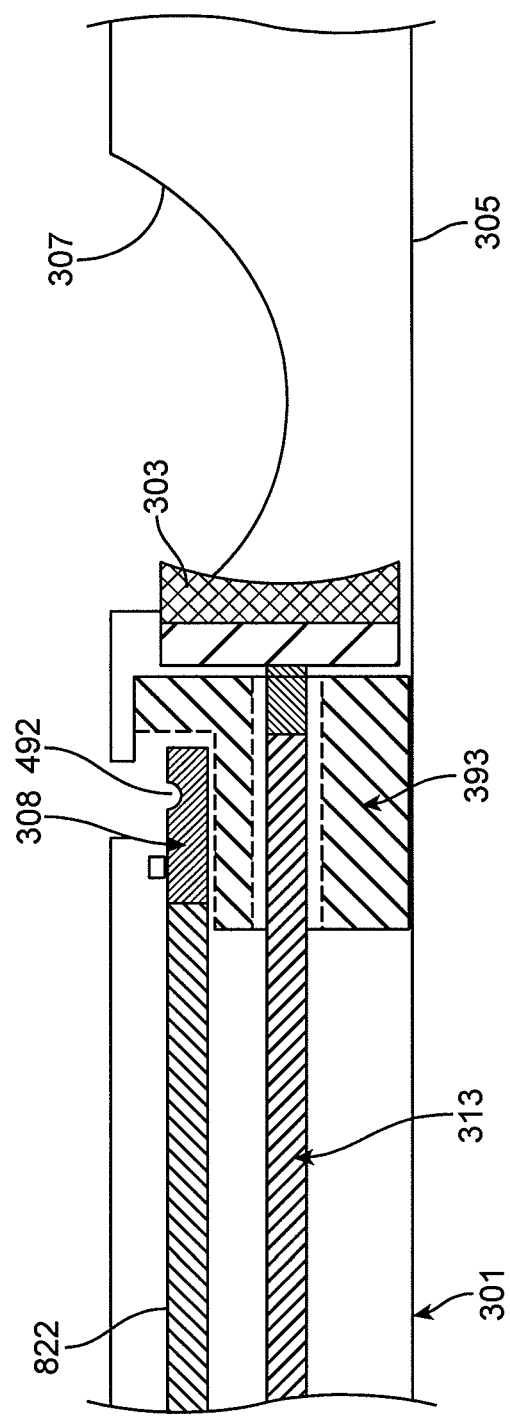
Figure 3C:
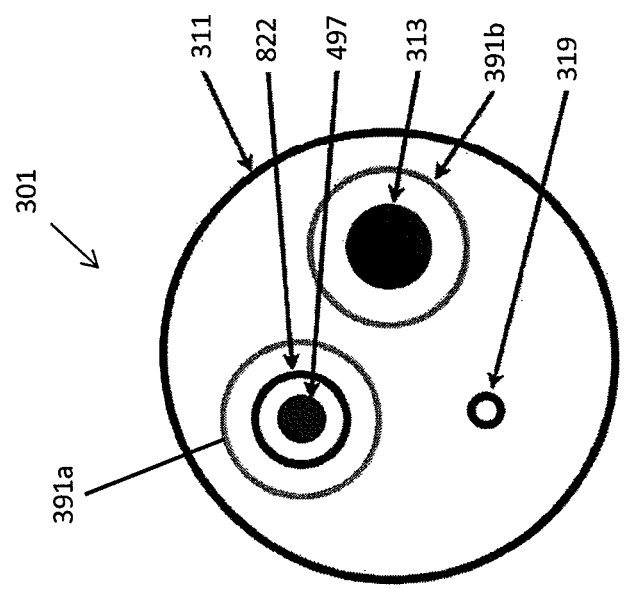

Referring to FIGS. 3A-3C, the catheter body 301 can include an outer shaft 311 and a drive shaft 313 extending inside the outer shaft 311. The outer shaft 311 can be configured to be turned, such as turned manually, to position the cutter 303 and/or the imaging tip 308 toward the desired location. The drive shaft 313 can be attached to the cutter 303 to rotate the cutter 303. Rotation of the cutter 303 can provide cutting due to the rotational motion of the sharp distal cutting edge. The drive shaft 313 can be rotated at up to 10,000 rpm, such as 1,000 to 5,000 rpm, e.g., 1,000 rpm, though rotation in both directions or at different speeds is possible. The drive shaft 313 can be held on-center at the distal tip of the device using a bushing 393 (within which the drive shaft 313 can rotate).

Referring still to FIGS. 3A-3C, the catheter 300 can further include an imaging element 492, such as an OCT imaging element. The imaging element 492 can include an optical fiber 497. The imaging tip 308 can be attached to an imaging shaft 822 that extends within the catheter body 301 next to or parallel with the drive shaft 313. The imaging shaft 322 can be off-center at the distal tip of the device and be parallel to the drive shaft 313, as shown in FIG. 3B. The imaging shaft 322 can be held in place by the bushing 393.

The rotation of the imaging shaft 822 and the drive shaft 313 can be decoupled at the distal end of the device, thereby providing for mechanically isolated rotation of the cutter 303 and the imaging element 492. As described below, in some embodiments, the rotation of the imaging shaft 822 and the drive shaft 313 can be coupled at the proximal end (such as in the handle so as to be driven by the same motor) while remaining decoupled along the length of the catheter. Optionally, as shown in FIG. 3C, the imaging shaft 822 and/or the drive shaft 313 can include a stationary sheath 391*a,b* therearound to provide protection and support.

The outer shaft 311 can include an imaging window 807 through which the imaging element 492 can be exposed. The imaging window 807 can have a width of less than 1 mm while still enabling OCT imaging therethrough. The imaging window 807 can extend 360 degrees around the circumference of the outer shaft 311, but can include structural struts 317 extending thereacross to both provide structural support and act as imaging markers. In some embodiments, the struts 317 can be offset to account for the off-center imaging tip 308, enabling accurate OCT image orientation.

The imaging window 807 can further be used as a flush port to allow flush fluid to be delivered through the imaging shaft 822 and to the area of imaging, thereby improving image quality. Advantageously, by having the fluid pumped directly through the imaging shaft, the dimensions of the imaging window 807 do not need to be extended to enable this type of flushing.

The optical fiber 497 can run through the imaging shaft 822 to provide the imaging (e.g., OCT) signal. The optical fiber 497 can be attached at its distal end to the imaging tip 308. The optical fiber 497 can otherwise be free to float within the imaging shaft 822. As shown in FIG. 3E, a reflective element 499, such as a mirror, polished pin, a film deposited on the surface of the tip 308, or polished surface of the tip 308 itself, can further be located on the imaging tip 308 to radially direct light from the optical fiber 497 into the tissue. The reflective element 499 can be at an angle, such as 35 to 55 degrees, such as 45 degrees, relative to the central axis of the fiber 497 to reflect light into the tissue. The distal end of the optical fiber 497 can be located less than 3 mm from the distal edge of the cutter 303, such as less than 2.0 mm from the cutting edge, such as less than or equal to 1.5 mm, such as less than or equal to 1 mm. By having the imaging element 492 close to the cutting edge, the resulting image can advantageously align with the portions of the vessel being cut.

Figure 3D:
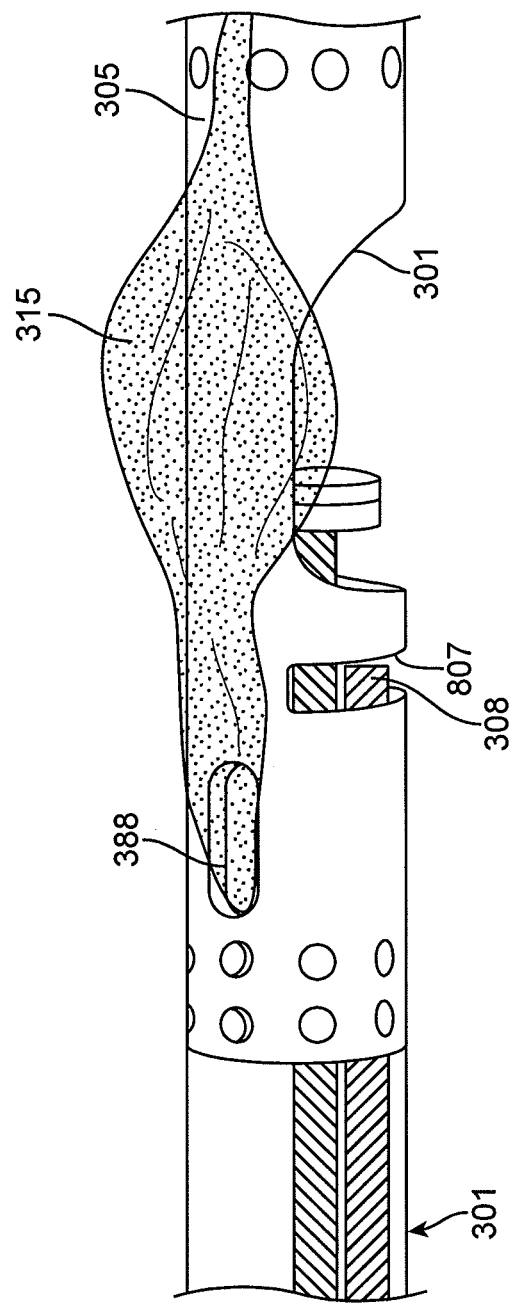
Figure 3E:
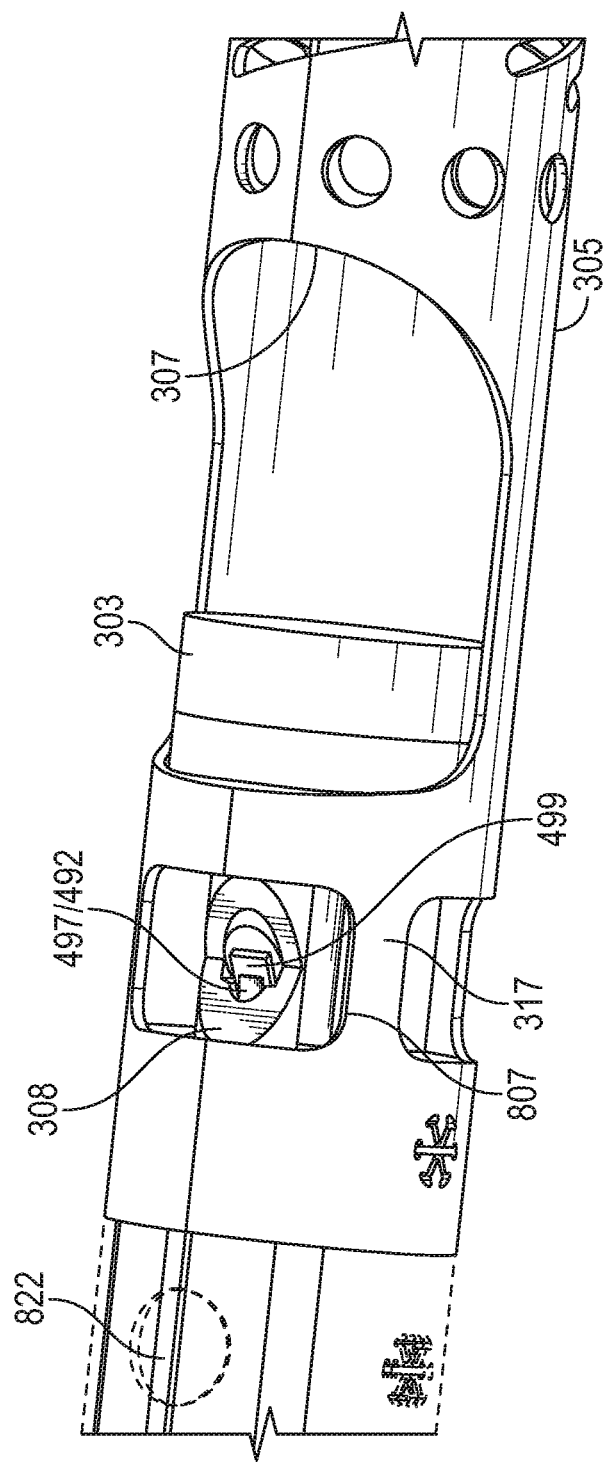

As shown in FIG. 3D, an inflatable element, such as a balloon 315, can be located opposite to the cutting window 307. The balloon 315 can be attached to an inflation tube 319 (see FIG. 3C), which can run inside the outer shaft 311. Thus, the balloon 315 can be attached at the distal end to the outer shaft 311 (just proximal to the imaging window 807) and at the proximal end to the inflation tube 319 inside the outer shaft 311, such as through a hole 388 in the outer shaft 311. Inflation of the balloon 315 can urge the cutting window 307 and thus the cutter 303 against the tissue. Further, the cutting window 307 and the balloon can be sized and dimensioned such that inflation of the balloon 315 causes the tissue to be forced into the cutting window, thereby improving the cutting quality of the device. For example, the cutting window 307 can have the same or similar dimensions to that described above for the cutting window 107 of catheter 100. In some embodiments, the balloon is approximately spherical and inflates to a diameter of 3-6 mm for a device sized to treat vessel that are greater than or equal to 2.5 mm.

The catheter 300 can further include a mechanism for packing tissue into the nosecone 305. Thus, for example, the cutter 303 can be moved distally by extending the drive shaft 313 distally. Advantageously, the drive shaft 313 can be translated proximally and distally while keeping the imaging shaft 822 (and thus the imaging sensor 492) in place.

Similar to catheters 100 and 1300, by having an imaging shaft that is separate from the drive shaft at least at the proximal ends in catheter 300, rotational distortion, such as NURD, can reduced or eliminated, thereby improving imaging quality. Further, by having separate imaging and drive shafts, the drive shaft can advantageously be used to pack tissue while maintaining the imaging element in the same location, thereby ensuring that the imaging location is constant and well known. Moreover, by having separate imaging and drive shafts, the fluid flush can be delivered close to the imaging element even when the drive shaft is moved distally to pack tissue.

Further, by using the balloon of catheter 300 to urge the cutter against the vessel wall and by having an optimally designed cutting window, tissue can be pulled into the cutting window and cut, thereby improving cutting quality without requiring a hinge mechanism in the catheter. Further, the balloon can advantageously act as an occlusion element to at least partially block blood flow to the imaging element, thereby reducing the amount of saline flush required to obtain a clear image and improving image quality.

In some embodiments, the drive shaft 313 and imaging shaft 822 can be unconnected at the distal end of the catheter to allow for separate imaging and cutting but connected at the proximal end of the catheter so that they can be rotated from the same source, such as the same drive system. Although the shafts can be connected at the proximal end of the cutter, rotational distortion can still be avoided because the rotating motor can be strong enough to spin at the same speed regardless of the torque placed on the catheter at the distal end. Accordingly, even if the drive shaft slows down due to stalling, the imaging shaft will continue to rotate at the same speed.

Figure 4A:
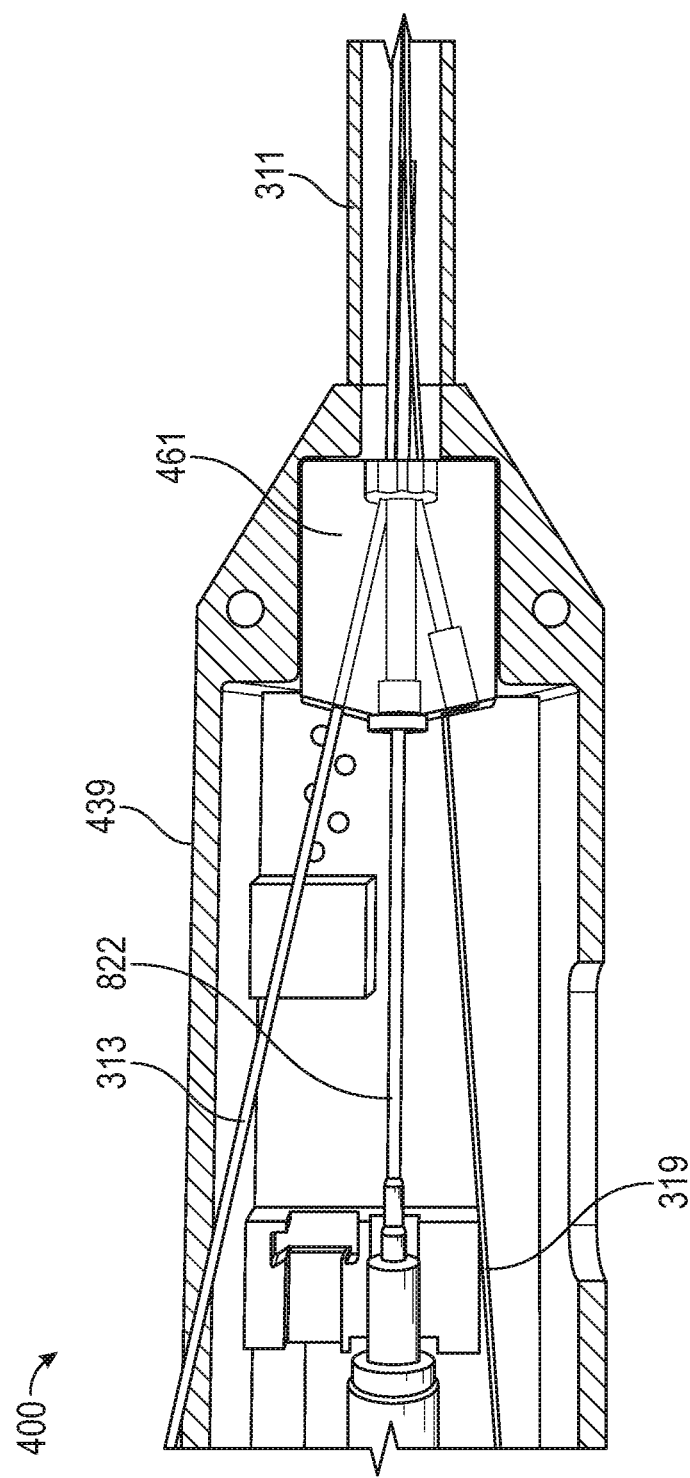
FIGS. 4A-4B show a handle for use with the atherectomy device of FIGS. 3A-3E.
Figure 4B:
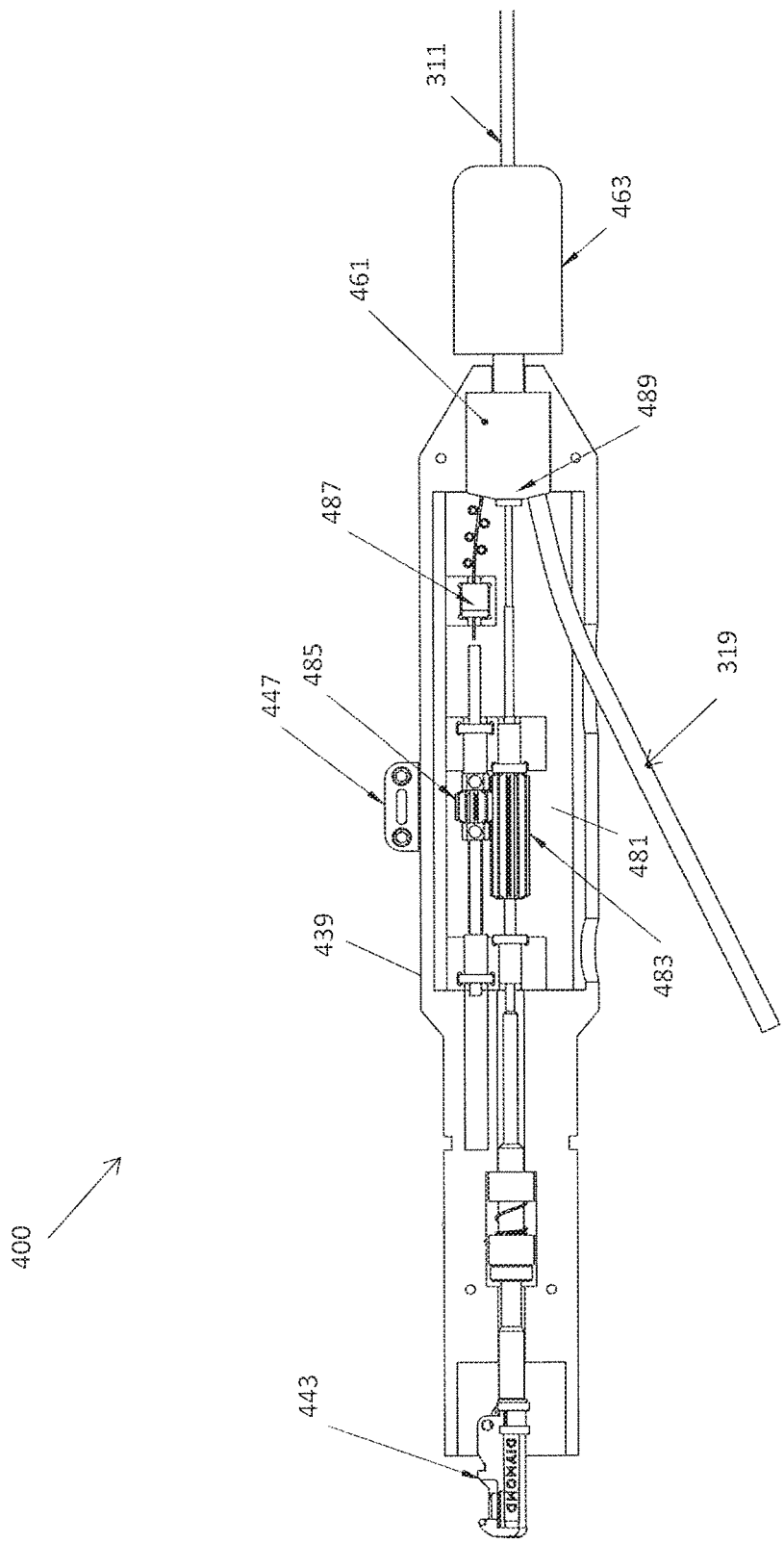

An exemplary handle 400 for use with catheter 300 is shown in FIGS. 4A-4B Referring to FIG. 4A, the handle 400 is configured to ensure that the drive shaft 313, the imaging shaft 822, and the balloon inflation lumen 319 inside the outer shaft 311 of the catheter 300 are all properly managed and controlled. A breakout port 461 in the handle 400 can separate the drive shaft 313, the imaging shaft 822, and the balloon inflation lumen 319 within the handle 400. In doing so, the imaging shaft 822 can be run through the center of the handle 400 so as to connect on-axis to the drive system through an optical connector (described below). The drive shaft 313 extends towards the top of the handle 400, where it is connected to the geared system (described below). Further, the balloon inflation lumen 319 extends towards the bottom of the handle, where it can be bonded into a tube with a female luer lock attachment for balloon inflation. In some embodiments, the breakout port 461 can be directly bonded to the outer shaft 311 (as shown in FIG. 3A) or it can be attached to a rotation knob 463 (as shown in FIG. 3B).

The handle 400 can be configured such that the drive shaft 313 and the imaging shaft 822 can be rotated separately at the distal end of the catheter but rotated with the same source at the proximal end of the catheter. The handle 400 can further include a mechanism that allows for axial translation of the drive shaft 313 (e.g., to pack tissue with the cutter), but not the imaging shaft 822.

Referring to FIG. 4B, the handle 400 can include an outer shell 439, a rotation knob 463 configured to connect to the outer shaft 311 of the catheter 300, and an optical connector 443 configured to engage with a drive system and light source. The optical connector 443 can provide both rotation from the drive system to directly drive the imaging shaft 822 and an OCT signal from the light source that can be translated through the optical fiber 497 embedded in the central lumen of the imaging shaft 822.

As shown in FIG. 4B, the handle can include a geared mechanism 481 configured to transfer rotation from the imaging shaft 822 to the drive shaft 313. The geared mechanism 481 can include an imaging drive gear 483 connected to a drive shaft gear 485. Thus, as the imaging shaft 822 is rotated by the drive system through the optical connector 443, the imaging drive gear 483 will rotate, causing the drive shaft gear 485, and thus the drive shaft 313, to rotate. In some embodiments, the geared mechanism 481 of the handle 400 can include a clutch that allows the drive shaft 313 rotation to be turned on and off while still allowing the imaging shaft 822 to rotate (advantageously allowing for imaging without requiring simultaneous cutting). The imaging drive gear 483 can be longer than the drive shaft gear 485. Accordingly, during translation of the handle ring or slide 447, the drive shaft gear 485 can be translated back and forth across the imaging drive gear 483, thereby maintaining full rotation of the drive shaft 313 during the packing and opening actions.

The handle 400 can further include a handle ring or slide 447 configured to slide along the handle 400 to translate the drive shaft 313 axially, such as to pack tissue by the cutter 303. As shown in FIG. 4B, a fluid seal 487 ensures that the handle 400 is fluid-tight during translation of the drive shaft 313. The fluid seal 487 can be in-line with the drive shaft gear 485 to prevent the drive shaft 313 from buckling. A sheath can be used bridge the gap between the fluid seal 487 and the breakout port 461. Moreover, an additional fluid seal 489 can be provided on the breakout port 461 to provide a seal for the imaging shaft 822.

The outer rotation knob 463 can be configured to rotate relative to the rest of the handle 400 to allow the user to torque the outer shaft 311 to orient the distal tip of the catheter 300 in the desired position. The knob 463 can rotate the outer shaft 311 independently of the imaging shaft 822, drive shaft 313, and inflation tube 319. Accordingly, the rotation of the knob can be limited to reduce wrapping or unwanted extension of the shafts/tube. For example, the rotation can be limited to less than 3 full rotations, such as less than 2 full rotations, such as less than 1.5 full rotations in either direction.

Referring to FIGS. 5A-5F, in one embodiment, the outer rotation knob 463 can include a mechanism for stopping the rotation if rotated more than 1 full rotation (360°) and less than 3 full rotations, such as approximately 1.5 rotations. The outer rotation knob 463 can also be configured so as to not require lengthening or shortening of the outer shaft 311 during rotation. That is, some rotation knobs (with pins attached to the outer shaft and a spiral track in the handle) can cause the outer shaft to be lengthened relative to the handle. Because the drive shaft would not concurrently lengthen and shorten, the fiber could snap and/or the cutter could be forced to move proximally or distally relative to the outer shaft. Accordingly, the outer rotation knob 463 described herein can be configured so as to not require lengthening or shortening of the outer shaft 311.

Figure 5A:
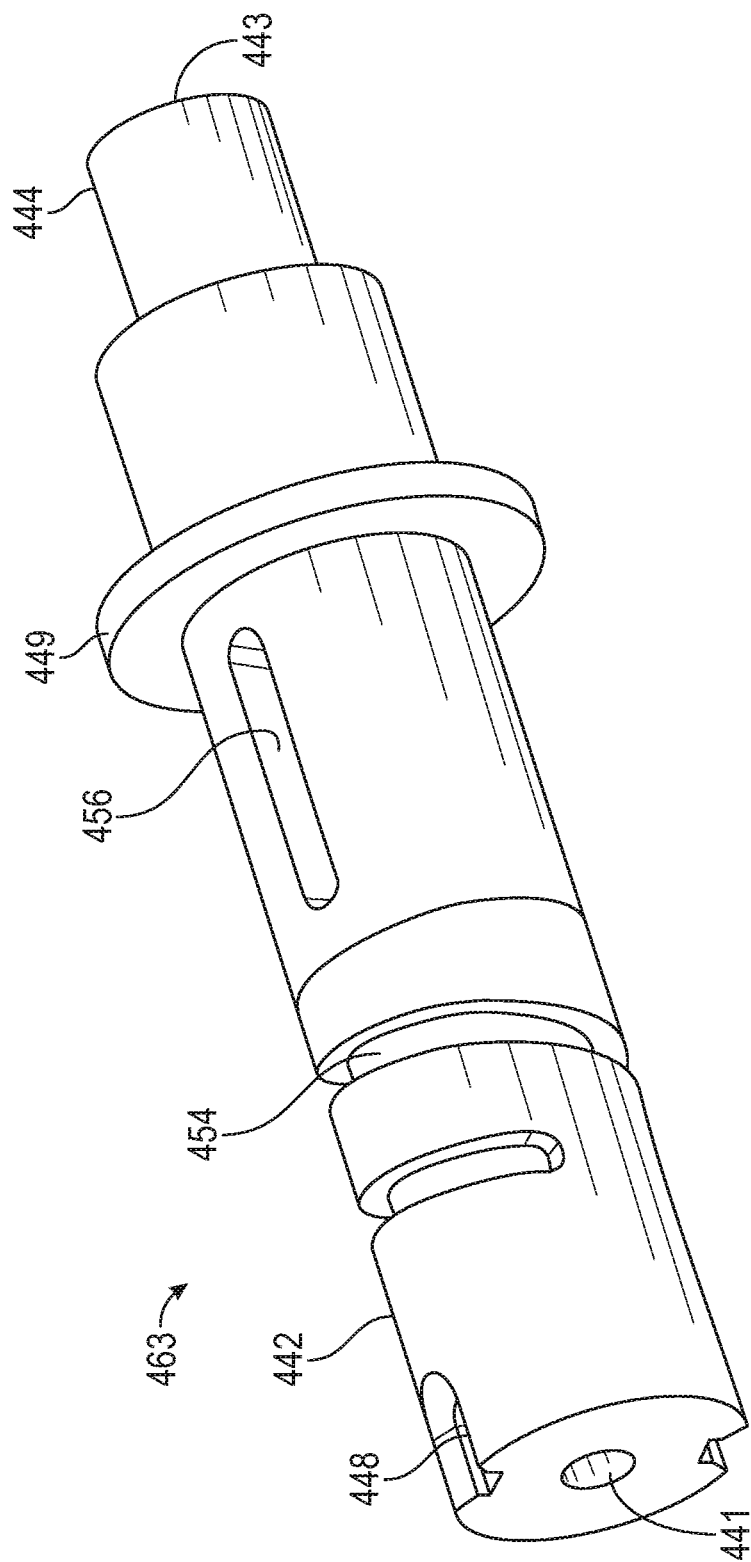
Figure 5B:
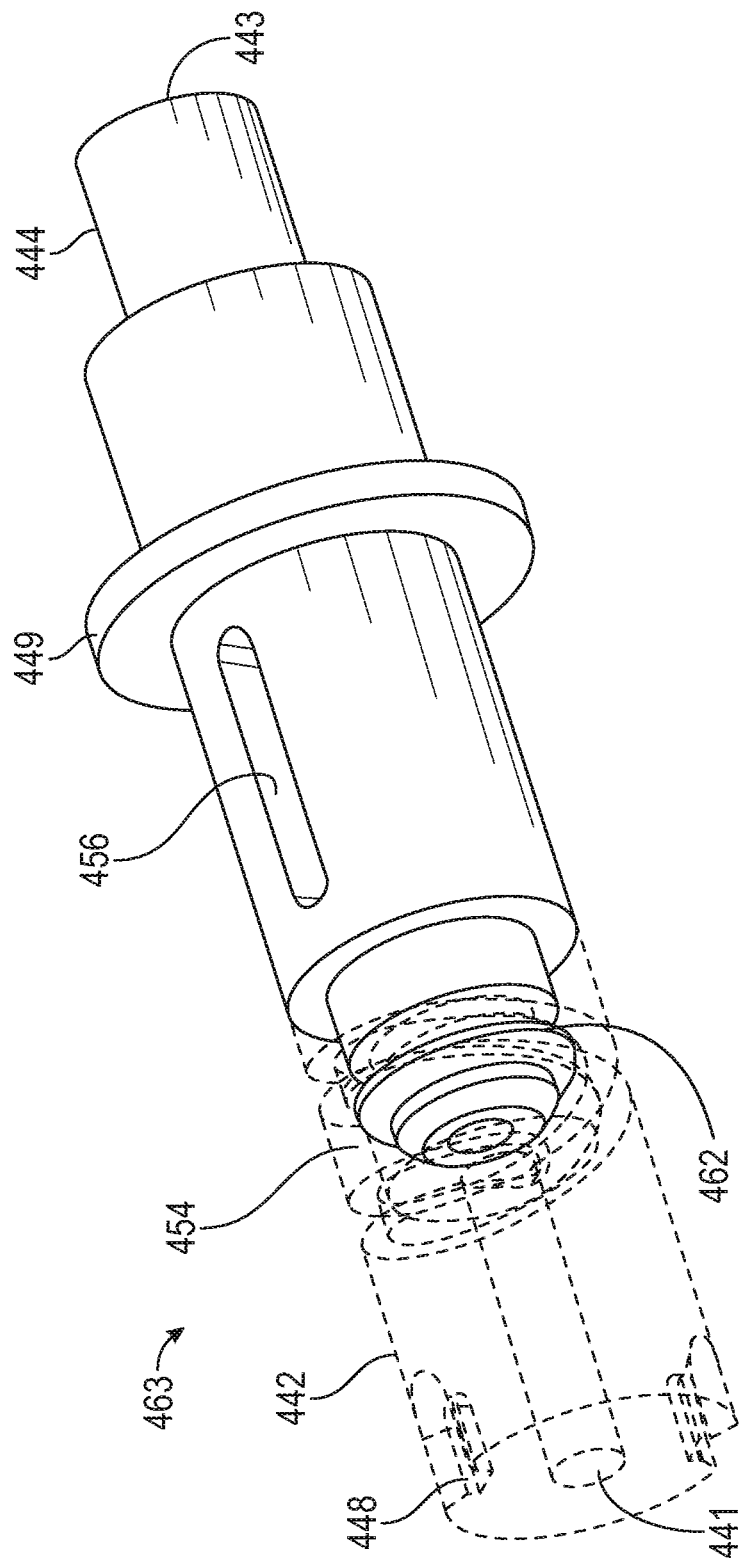

Referring to FIGS. 5A and 5B, the knob 463 can include a shaft inner portion 442 connectable to the outer shaft 311 at connection point 441 and a handle inner portion 444 connectable to the rest of the handle 400 at connection point 443. The shaft inner portion 442 can include a spiral track 454 that spirals around the inner portion 442 for more than 360 degrees and less than 1080 degrees, such as approximately 540 degrees. The shaft inner portion 442 can further include one or more linear tracks 456 extending axially along the inner portion 442. For example, there can be two linear tracks 456 that are located 180 degrees away from one another. Having more than one linear track 456 can advantageously help stabilize the relative axial movement of parts within the knob 463. An o-ring 462 (see FIG. 4D) can create a seal between the two inner portions 442, 444. The inner portion 442 can further include one or more indents 448 therein as well as an annular ridge 449 extending therearound.

Figure 5C:
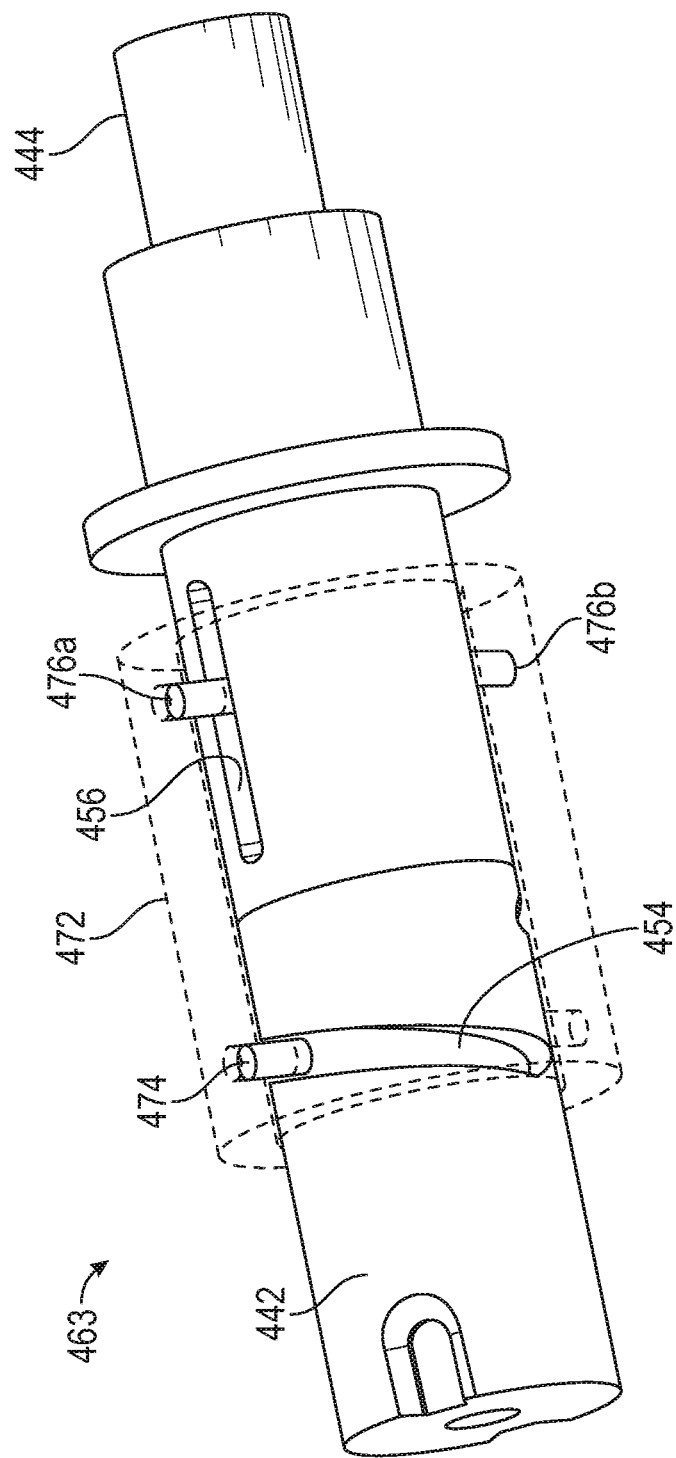

Referring to FIG. 5C, the knob 463 can further include a sleeve 472 that extends around the shaft inner portion 442. The sleeve 472 can have a pin 474 that fits into the spiral track 454, as well as pins 476a,b that fit into the linear track 456.

Figure 5D:
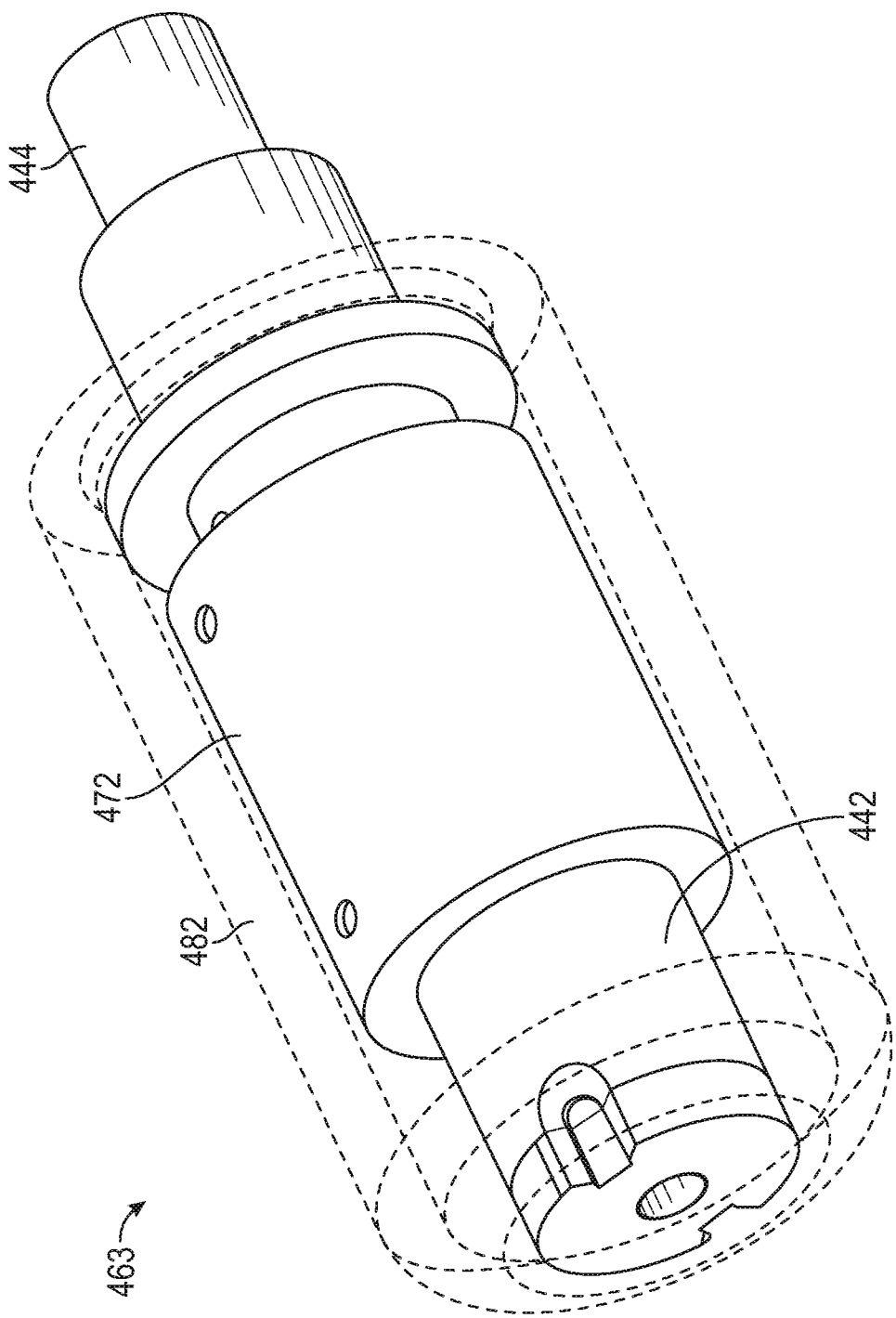

Referring to FIG. 5D, the knob 463 can further include an outer portion 482 that extends around the sleeve 472 (but not attached to the sleeve 472). The outer portion 482 can snap fit with the ridge 449 and the indents 448 of the shaft inner portion 442.

Figure 5F:
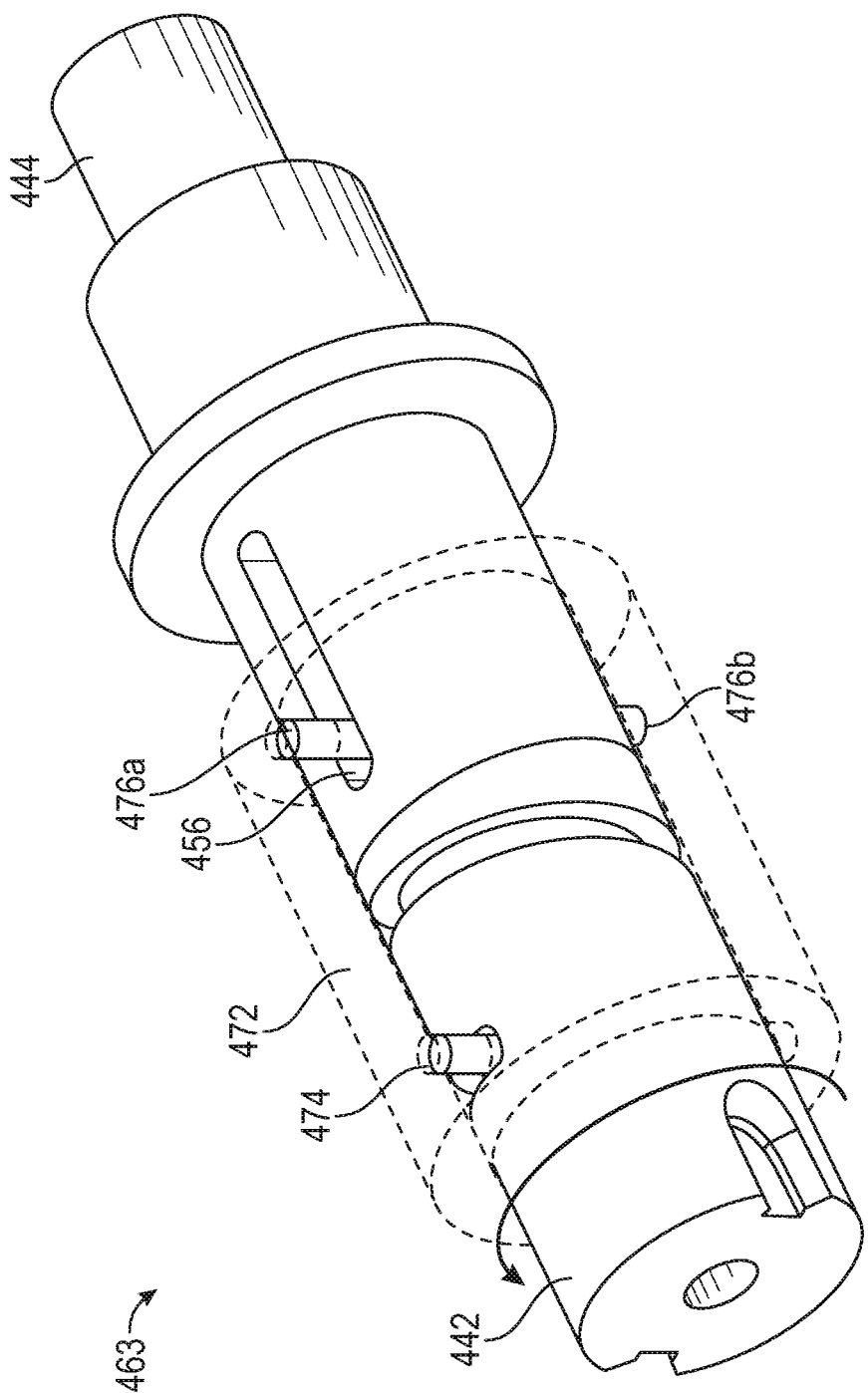

Thus, referring to FIGS. 5E and 5F, as the outer portion 482 is rotated by a user, it will rotate the drive shaft inner portion 442. As the drive shaft inner portion 442 rotates, the pin 474 will slide along the spiral track 454 and cause the sleeve 472 to translate linearly due to the placement of the pins 476a,b in the linear track 456 (as shown in the movement of the sleeve 472 distally from FIG. 5E to FIG. 5F). When the pins 474 in the spiral track 454 reaches the end (and/or when the pins 476a,b in the linear track 454 reach the end), rotation in that direction is prevented. Thus, the rotation knob (and thus the drive shaft) is only able to rotate a fixed number of rotations. Further, because the sleeve 472 translates linearly rather than the outer shaft 311, relative movement of the cutter and/or distortion in imaging can be avoided.

In some embodiments, the handle 400 can include one or more luer ports such that the user can deliver imaging flush and balloon inflation to the distal tip.

Handle 400 advantageously provides for rotation of the parallel imaging and drive shafts while allowing for axial movement of the drive shaft and not the imaging shaft or imaging fiber. Moreover, the handle provides for connection to a drive system at high rotation speeds (such as up to 10,000 rpm), it provides a fluidic seal to enable flushing from the handle to the distal tip, it provides for balloon inflation via air or solution, it allows for independent rotation of the outer shaft, and it allows the balloon lumen to be moved from the outer diameter of the torque shaft to the interior annular space of the torque shaft to increase usability of the device.

Although described as being used with catheter 300, it is to be understood that the handle 400 and/or elements of the handle could be used with a variety of different catheters while still providing separate rotating of concentric imaging and drive shafts and/or axial movement of one or more shafts without axial movement of another.

FIGS. 6A-9B show an exemplary atherectomy device (and corresponding exemplary handles) having a balloon hinge mechanism configured to drop the nosecone and expose a cutter as well as a return biasing mechanism to realign the nosecone with the catheter body.

Figure 6A:
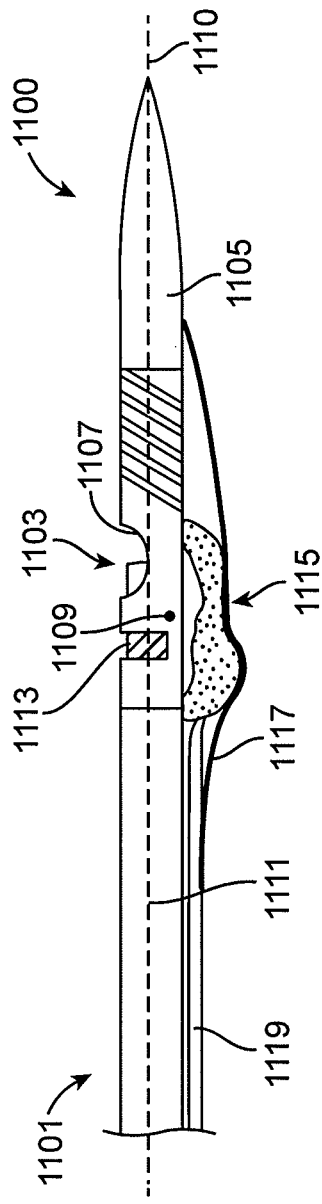
FIGS. 6A-6B show a variation of an atherectomy catheter having an inflatable element configured to deflect the nosecone away from the catheter body at a hinge point to expose a cutter.
Figure 6B:
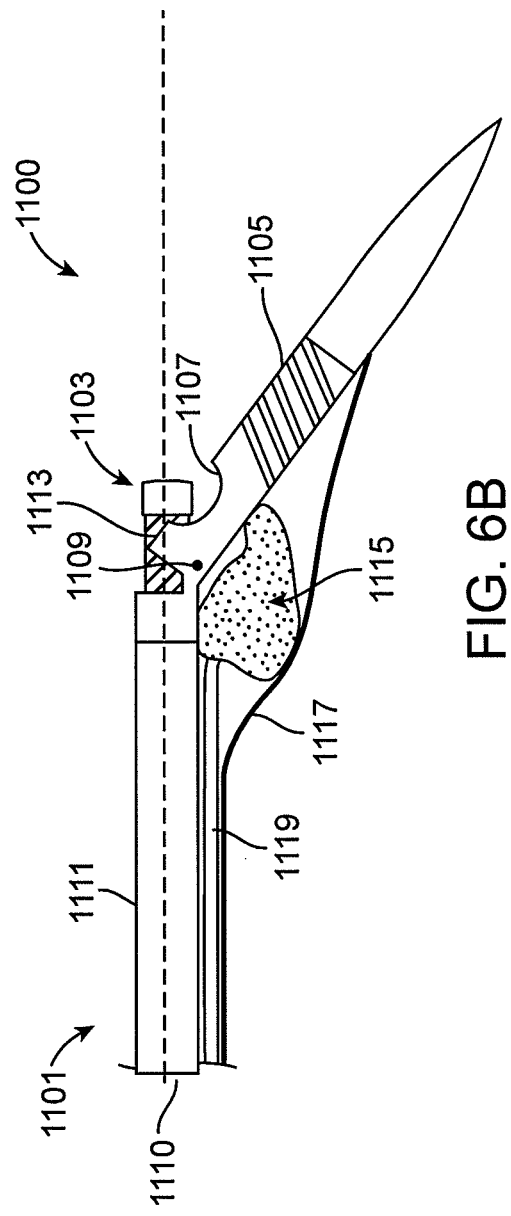

Referring to FIGS. 6A and 6B, a catheter 1100 can include a catheter body 1101, a cutter 1103 extending from the distal end of the catheter body 1101, and a nosecone 1105 attached to the distal end of the catheter body 1101. The nosecone 1105 can include a cutting window 1107 through which the edge of the cutter 1103 can be exposed. The nosecone 1105 can be configured to deflect away from the longitudinal axis 1110 of the catheter body 1101 at an angle, such as at a hinge point 1109. In use, this deflection can expose the cutter 103 through the cutting window 1107 and/or radially push the cutter 1103 into a wall of the vessel in which the atherectomy catheter is inserted.

Figure 6C:
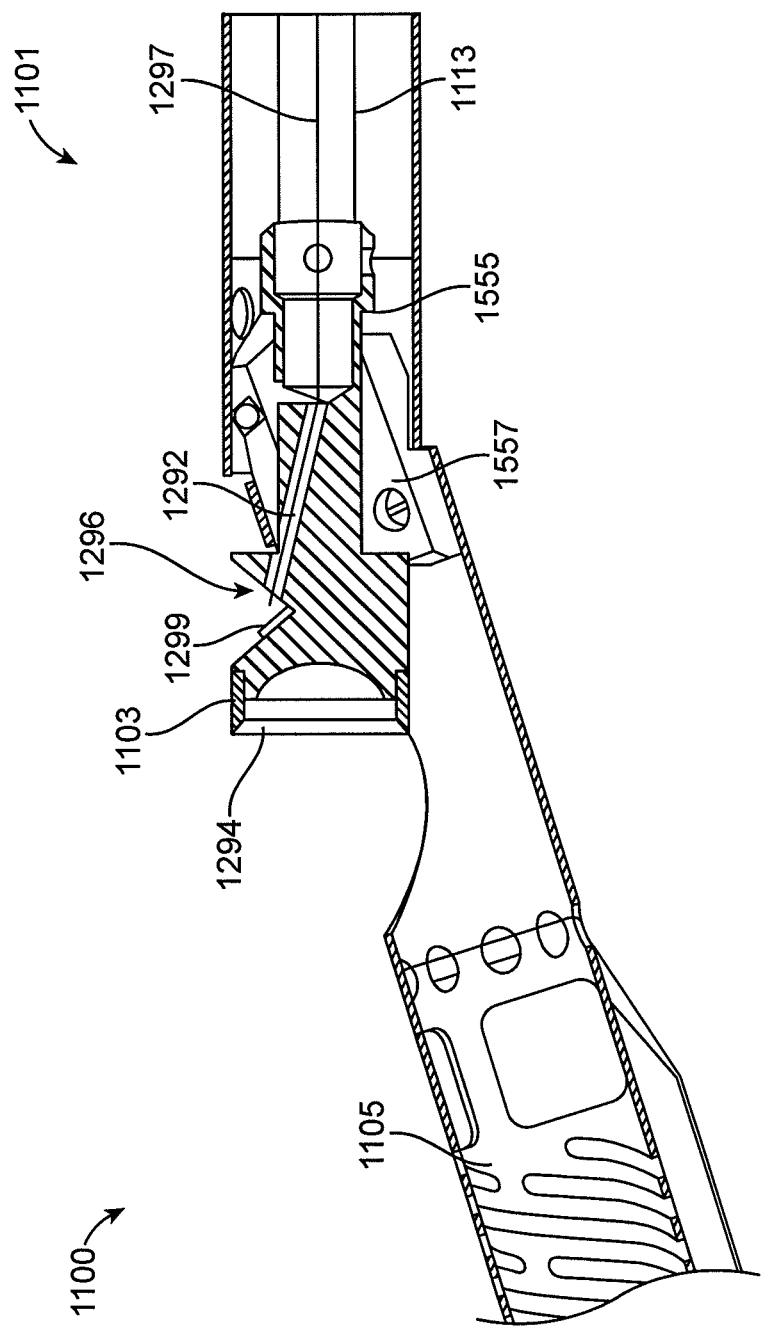
FIGS. 6C-6D show an exemplary detailed view of the imaging element and the hinged activation closing mechanism of the catheter of FIGS. 6A-6B.
Figure 6D:
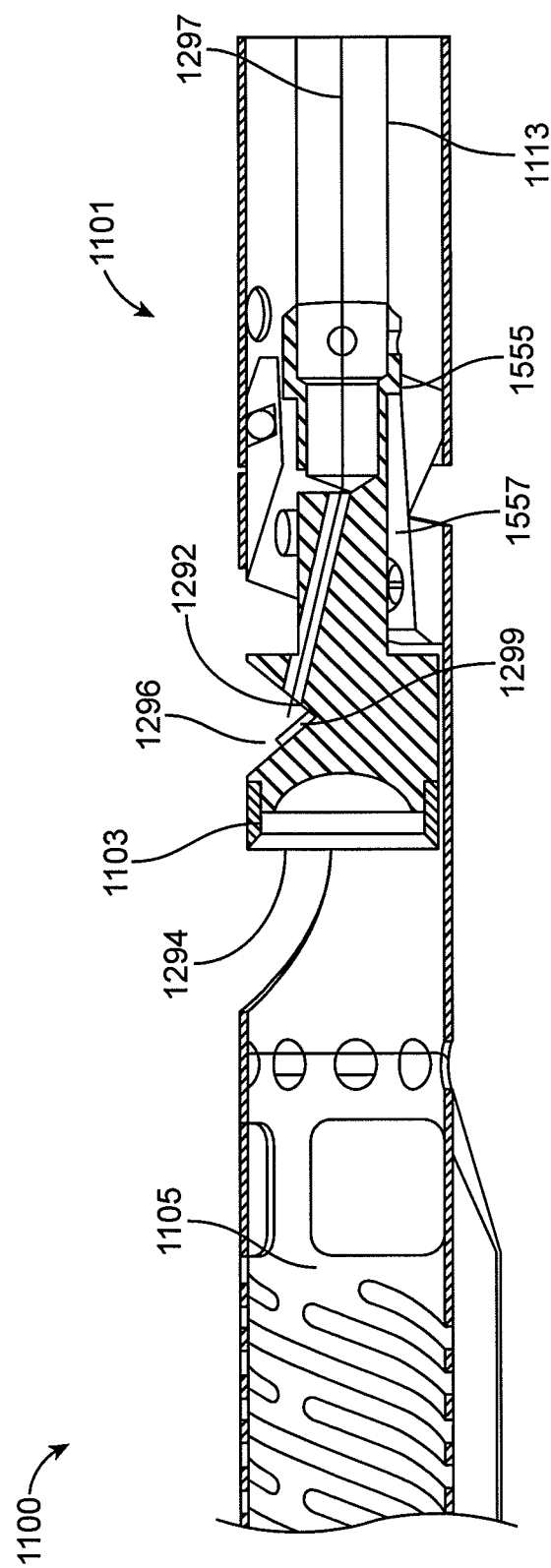

Referring to FIGS. 6C-6D, the atherectomy catheter 1100 can include an imaging element 1292, such as an OCT imaging element, proximal to the cutting edge 1294 of the cutter 1103. An optical fiber 1297 can run through the elongate body, such as on-axis with the catheter body 1101 through a drive shaft 1113, to provide the OCT signal. The optical fiber 1297 can be attached at the distal end to the cutter 1103, such as in an opening 1296 in the cutter 1103. The optical fiber 1297 can otherwise be free to float within the catheter body 1101 and/or drive shaft 1113. A reflective element 1299, such as a mirror, can further be located within the opening 1296 in the cutter 1103 to radially direct light from the optical fiber 1297 into the tissue. The reflective element 1299 can be at an angle, such as 35 to 55 degrees, such as 45 degrees, relative to the central axis of the fiber 1297 to reflect light into the tissue. The distal end of the optical fiber 1297 can be located less than 3 mm from the cutting edge 1294, such as less than 1.5 mm from the cutting edge, such as less than or equal to 1.2 mm, such as less than or equal to 1 mm. By having the imaging element 1292 close to the cutting edge 294, the resulting image can advantageously align with the portions of the vessel being cut.

Referring back to FIGS. 6A-6B, the catheter body 1101 can include an outer shaft 1111 and a drive shaft 1113 extending inside and concentric with the outer shaft. The outer shaft 1111 can be configured to be turned, such as turned manually, to position the cutter 1103 and/or the imaging element toward the desired location. The drive shaft 1113 can be attached to the cutter 1103 to rotate the cutter 1103. Rotation of the cutter 1103 can provide cutting due to the rotational motion of the cutting edge while providing the rotation necessary to image the circumference of the inner wall of a vessel via the imaging element. The drive shaft 1113 can be rotated at up to 2,000 rpm, such as approximately 1,000 rpm in a single direction, though rotation in both directions or at different speeds is possible.

As described above, the atherectomy catheter 1100 can include a hinge point 1109 to provide a rotational axis during opening of the nosecone 1105. For example, the hinge point 1109 can be a living hinge or a pin that attaches to either the proximal or distal housings. As shown in FIGS. 6A-6B, an inflatable element, such as a balloon 1115 can be located proximate to the hinge point 1109 and opposite to the cutting window 1107. The balloon 1115 can be linked to both the distal end of the catheter body 1101 and the proximal end of the nosecone 1105. For example, a sling element 1117, such as a polyester sling or a metal or polymer wire sling, can cross over the outer surface of the balloon 1115 and be attached to both a distal end of the catheter body 1101 and a proximal end of the nosecone 1105.

Figure 6E:
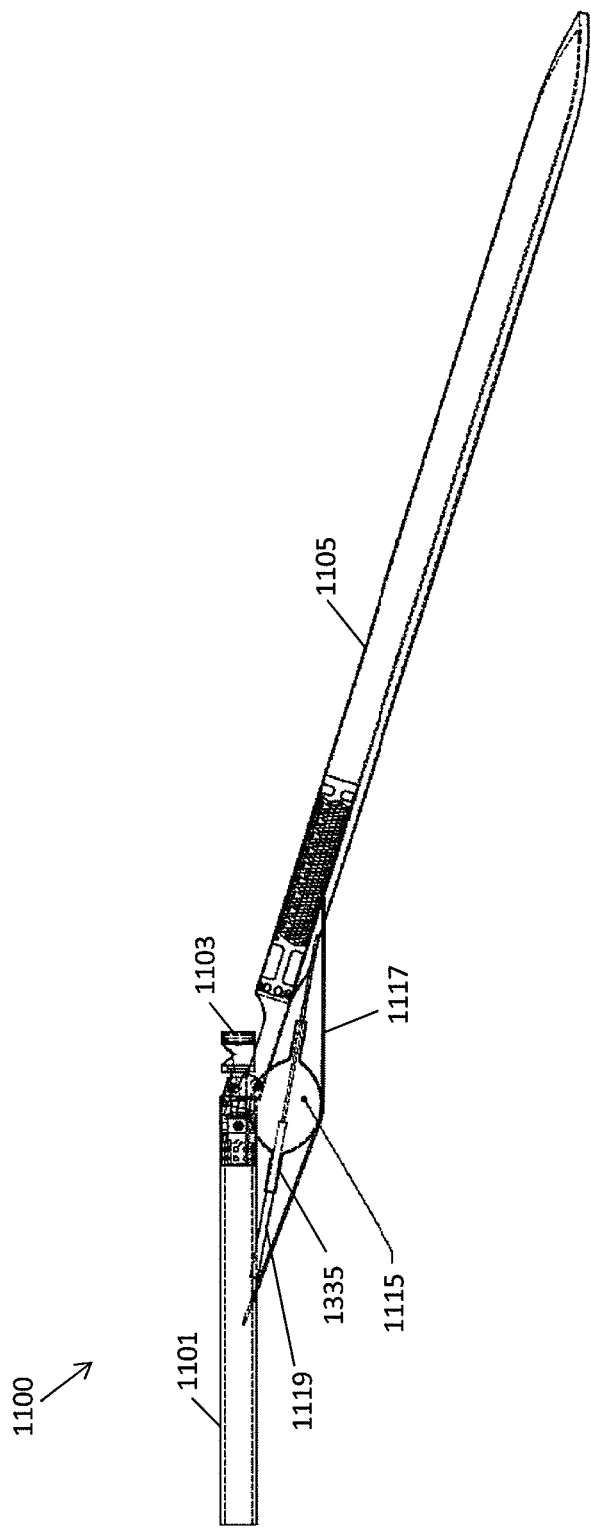
FIG. 6E shows an exemplary detailed version of the atherectomy catheter of FIGS. 6A-6B including a balloon and sling element for deflecting the nosecone and exposing the cutter.

The balloon 1115 can be attached to an inflation tube 1119. As shown in FIGS. 6A-6B, the inflation tube 1119 can be a hypotube running along the outside of the catheter body 1101. In other embodiments, the inflation tube can extend inside the outer shaft 1111 or the drive shaft 1113. Referring to FIG. 6E, the inflation tube 1119 can extend through the proximal and distal end of the balloon 1115. The portion 1335 of the inflation tube 1119 that extends out the distal end of the balloon 1115 can be flexible and extend into a lumen in the wall of the nosecone 1105. The distal end can then translate proximally and distally within the nosecone lumen as the nosecone 1105 is opened and closed, respectively. The extension of the portion 1335 of the inflation tube out of the distal end of the balloon 1115 and into the nosecone 1105 advantageously provides support for the balloon 1115 to ensure both axial alignment and stability of the balloon 1115. In other embodiments, rather than translating the inflation tube 1119 within the nosecone, the inflation tube 1119 can be configured to translate within the catheter body 1101.

In use, the balloon 1115 can be inflated, through the inflation tube 1119, with a gas or liquid. As the balloon 1115 inflates, it can apply force to the center of the sling element 1117. The force on the center of the sling element 1117 can push the center away from the central axis 1110 of the catheter body 1101 and cause the attached edges of the sling element 1117 to pull on the distal end of the catheter body 101 and the proximal end of the nosecone 105. The simultaneous pulling on both the catheter body 1101 and the nosecone 1105 can force the catheter 1100 to bend at the hinge point 1109, thereby exposing the cutter 1103 out of the window 1107. In some embodiments, the cutter 1103 can have a diameter that is smaller than the window 107 to allow it to extend out of the window 1107.

Advantageously, by using the balloon 1115 to open the nosecone 1105, less force is placed on the drive shaft 1113 (relative to designs where tension or compression must be placed on the drive shaft to open the nosecone), thereby improving image quality. Further, the balloon 1115 can advantageously act as an occlusion element to at least partially block blood flow to the imaging element 1292, thereby reducing the amount of saline flush required to obtain a clear image and improving image quality. Further, use of the balloon 1115 to activate deflection can advantageously provide user-adjustable force for engaging the cutter 1103 with a vessel wall, as the balloon 1115 can be adjusted to provide variable urge force. Moreover, in some embodiments, the sling mechanism 1117 can act as a smooth sliding surface against the inside of a vessel, allowing it to maintain contact with the tissue without having an abrupt change in diameter. The sling mechanism 117 can also advantageously protect the balloon 1115 to avoid popping of the balloon 1115 or peeling of the balloon 1115 away from the catheter body 1101 due to friction.

In order to close the nosecone 1105 and store the cutter 1103, the balloon 1115 is deflated. As the balloon 1115 is deflated, the sling element 1117 becomes less taut, releasing the nosecone 1105 deflection force. In order to fully close the nosecone 1105, a biasing mechanism can be used. Referring to FIGS. 6C-6D, in one embodiment, to close the nosecone 1105, the drive shaft can be pushed distally, causing a distally-facing flange 1555 on the cutter 1103 to engage a nosecone wedge 1557, driving the nosecone 1105 upwards and back into alignment with the outer shaft 1101. The return of the nosecone 1105 to the closed position can also be aided by having a tight concentric fit between a distal end of the nosecone 1105 and the outer shaft 1111 such that, once the distal end of the nosecone 1105 begins to align with outer shaft 1111, it is forced upwards and into alignment. Using a closing mechanism that is distinct from the balloon 1115 advantageously ensures that the nosecone 1105 fully closes, thereby allowing full tissue part-off and packing into the nosecone 1105.

In some embodiments, rather than (or in addition to) closing the nosecone through movement of the drive shaft (as described with respect to FIGS. 6C-6D), the hinge mechanism 1109 can be a living hinge.

The nosecone 1105 can open using the balloon 1115 and sling 1117 while it can close by either moving the drive shaft 1113 and forcing the nosecone 105 closed over the nosecone wedge 1557 or by use of a living hinge. By allowing the balloon 1115 to open the nosecone 1105, forces are advantageously minimized at the imaging element 1292 during atherectomy. This is less of an issue when closing the nosecone 1105 after cutting, as the closing and packing of the cutter 1103 is carried out after therapy is complete. Further, using either movement of the shaft and the nosecone wedge 1557 or a living hinge to close the nosecone advantageously brings the nosecone 1105 fully on-axis with the catheter body 1101 before the cutter 1103 moves into the nosecone 1105 (as described further below), preventing the cutter 1103 from hitting the nosecone 1105 housing and thus preventing the cutter 1103 from dulling over time.

Further, the catheter 1100 can include a mechanism for packing tissue into the nosecone 1105, such as by moving the drive shaft 1113 axially. In one embodiment, as described above, movement of the drive shaft distally closes the nosecone 1105. Moving the drive shaft 1113 further distally will move the cutter 1103 into the nosecone 1105, thus packing tissue with a distal face of the cutter.

Figure 7:
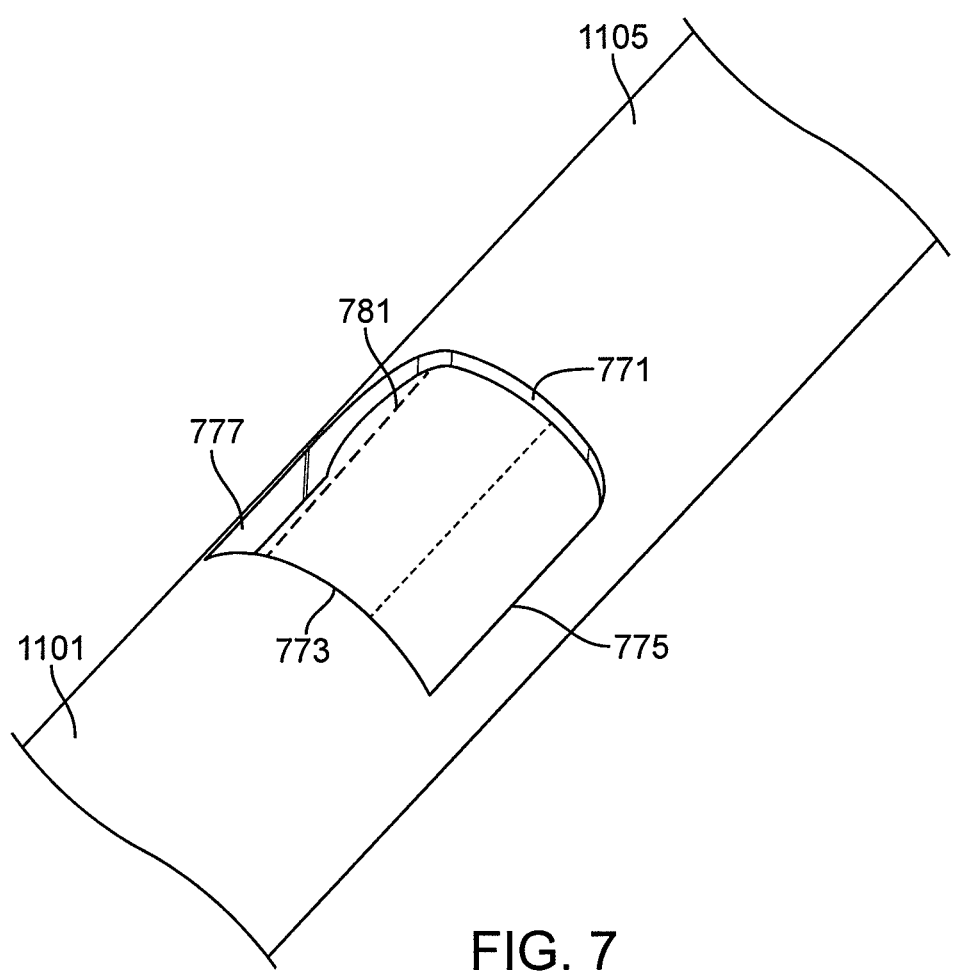
FIG. 7 shows an asymmetric cutting window.

In some embodiments, the cutting window 1107 can be designed so as to further prevent the cutting window 1107 from interfering with the movement of the drive shaft 1113 and cutter 1103 distally. For example, as shown in FIG. 7, the window 1107 can have a distal edge 771, a proximal edge 773, a linear edge 775, and a curvilinear edge 777. The proximal edge 773 can have a length that is longer than the distal edge 771. The curvilinear edge 777 can curve towards the distal edge 771. Further, the curvilinear edge 777 can be configured to be the side towards which the cutter 1103 rotates (as shown by the arrow 781). Because the cutter 1103, when it is extended into the nosecone to pack tissue, moves distally, it will extend along the curvilinear edge 777, which will deflect the cutter 1103 into the nosecone 1105, thereby avoiding contact of the cutter 1103 with the distal edge 771 (which might otherwise occur if the cutter 1103 is slightly off-axis, such as if the nosecone 1105 has not return fully in-line with the catheter body 1101). Avoiding contact of the cutter 1103 with the distal edge 771 advantageously prevents interference of the cutting window 1107 with movement of the drive shaft and protects the cutter 1303 from dulling over time. In some embodiments, the curvilinear edge 777 can have a height (along the radial axis of the device) that is greater than the height of the oppose linear edge 775. Have a greater height can advantageously help prevent tissue from escaping the tissue window, as the tissue tends to spiral and move in the direction that the cutter is moving. The curvilinear edge can be used for the cutting window 1107 in place of or in addition to the closing mechanisms for the hinge (such as the wedge and the living hinge).

Although the balloon/hinge embodiments have been described herein with respect to a catheter having a single drive and imaging shaft, it is to be understood that the same mechanisms could be used with any of the catheters described herein, including the catheters with separate imaging and drive shafts.

Referring to FIGS. 8A-9B, the atherectomy catheters described herein can be used with a handle configured such that the optical fiber can be extended axially a distal location, e.g., with the drive shaft to pack tissue or manipulate the nosecone, without requiring axial movement of the optical fiber at a proximal location, e.g., without requiring movement of the optical fiber assembly with the drive system. Thus, the handle can be designed to completely account for movement of the drive shaft.

In one embodiment, shown in FIGS. 8A-8B, a handle 1800 can include a rigid tube 1802. The proximal portion 1804 of a compliant flexible drive shaft (e.g. a drive shaft used for any of the above described catheters) can be axially constrained relative to the rigid tube 1802 at the proximal end 1808 of the handle 1800. For example, the proximal portion 1804 of the flexible drive shaft can be attached so that it is free to rotate relative to the tube 1802 yet constrained so that it is unable to translate relative to the tube 1802, such as via a rotatable bushing that is translationally locked at the proximal end 1808 of the handle 1800. The rest of the flexible drive shaft can be otherwise unattached to the rigid tube 1802 where it is free to rotate and translate.

When the flexible drive shaft is in the normal or compressed configuration, as shown in FIG. 8A, the proximal portion 1804 of the flexible drive shaft can be coiled or otherwise collapsed within the inner perimeter of the rigid tube 1802. As tension is applied on the flexible drive shaft in the distal direction, the coils can unwind or the distal portion otherwise extend, allowing for relative translation between the distal end of the flexible drive shaft and the rigid tube 1802. Thus, when the flexible drive shaft is in the extended configuration, the proximal portion 1804 of the flexible drive shaft that was coiled or compressed within the rigid tube 1802 can extend out of the distal end 1818 of the rigid tube 1802, as shown in FIG. 8B, allowing the distal end of the flexible drive shaft to be translated distally.

The handle 1800 can allow for a set range of translation that is established by several factors, including the overall length of the distal portion 1804 of the flexible drive shaft, the length of the rigid tube 1802, the radius of curvature of the proximal portion 1804 of the flexible drive shaft which correlates to its ability to collapse, and the inner diameter of the rigid tube 1802 which correlates to its capacity to manage and contain the collapsed distal portion 1804. For example, the amount of translation of the flexible drive shaft can be approximately 1 inch.

Figure 9A:
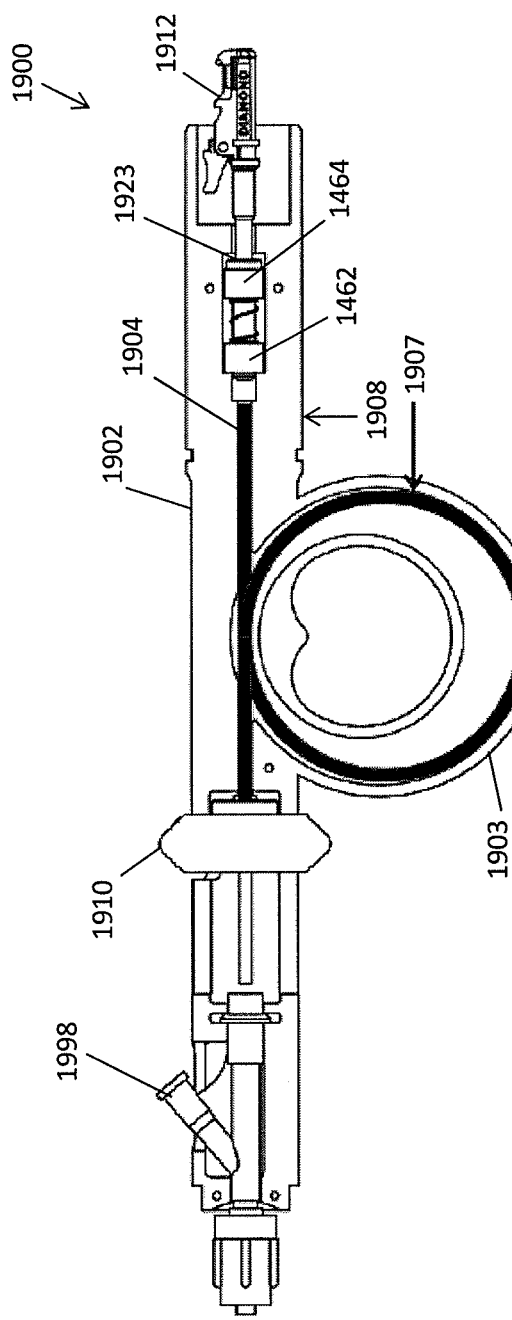
FIGS. 9A-9B shows a second embodiment of a handle configured such that the inner drive shaft can be extended axially at the distal end without requiring axial movement of the drive shaft at the proximal end.
Figure 9B:
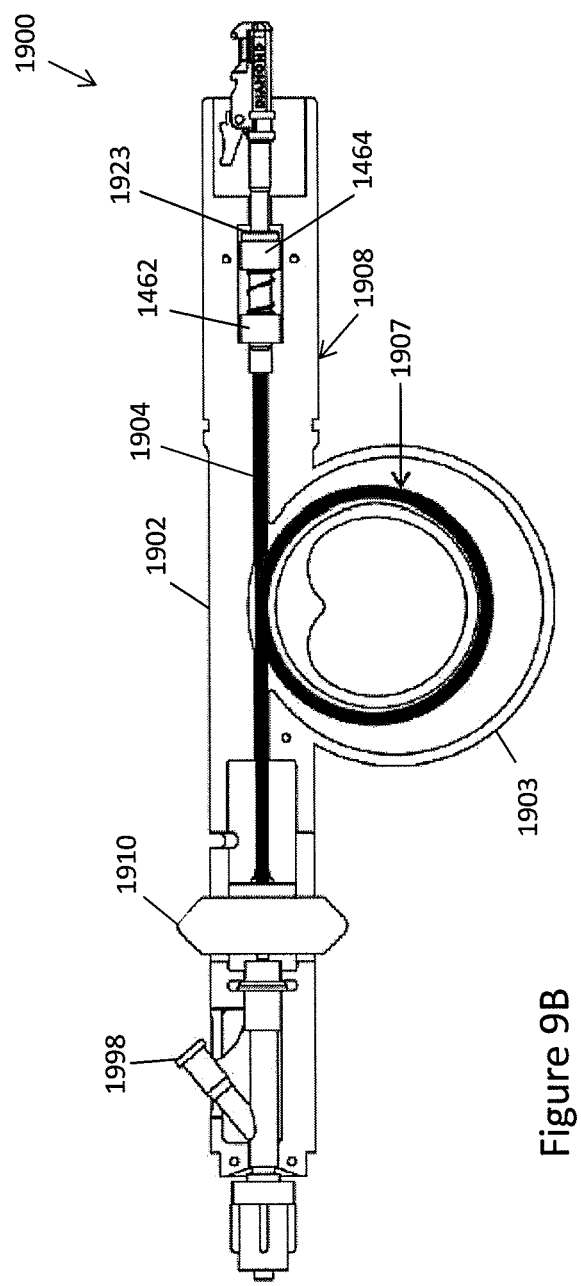

In another embodiment of a handle configured to provide all of the axial movement of a drive shaft, referring to FIGS. 9A-9B, a handle 1900 can include a rigid tube 1902 formed into a loop 1903. The proximal portion 1904 of a flexible drive shaft (e.g. a drive shaft used for any of the above described catheters) can be axially constrained relative to the rigid tube 1902 at the proximal end 1908 of the handle 1900. For example, the flexible drive shaft can be locked in place translationally on the proximal handle 1908 via a rotatable bushing 1464. The drive shaft can spin inside of this bushing 1464, but a rib 1923 on the distal end (and a distal bushing 1462) prevent the drive shaft from translating axially.

The rest of the flexible drive shaft can be otherwise unattached to the rigid tube 1902. The distal portion 1904 of the flexible drive shaft can form a loop 1907 within the loop 1903 of the rigid tube 1902. The rigid tube 1902 can be configured such that, as shown in FIG. 9A, when the distal portion 1904 of the flexible drive shaft is in the normal or compressed configuration, the loop 1907 of the flexible drive shaft conforms to the outer perimeter of the loop 1903 of the rigid tube 1902. As tension is applied on the flexible drive shaft in the distal direction, the loop 1907 of the flexible drive shaft will tighten. Accordingly, as shown in FIG. 9B, when the flexible drive shaft is in the extended configuration, the loop 1907 of the flexible drive shaft conforms to the inner perimeter of the loop 1903 of the rigid tube 1902, allowing the distal end of the flexible drive shaft to be translated distally.

The handle 1900 can allow for a set range of translation that is established by the relative difference in length between the outer and inner perimeters of the loop 1903 of the rigid tube 1902. For example, the loop 1907 of the flexible drive shaft can expand from 2 inches to 2.6 inches, allowing for up to 1.8 inches of translation by the flexible drive shaft at the distal end.

In some embodiments, the flexible drive shafts described herein can include a flexible outer tube surrounding an inner coil. The inner coil can spin within the outer tube while the outer tube provides support for the coil to maintain its shape while manipulated.

Both of the handles 1800 and 1900 can include a mechanism on the handle to control the extension of the distal wire. For example, as shown in FIGS. 9A and 9B, the handle 1900 can include a user slide 1910 attached through the rigid tube 1902 to the distal portion 1904 of the flexible drive shaft. The user slide 1910 can slide proximally and distally to control the tensioning or compression of the distal portion of the flexible drive shaft.

The handles 1800 and 1900 can further include a coupling, such as the coupling 1912 configured to couple the respective handle with a drive mechanism. The distal portion of the drive shaft can be placed in-line with the drive system, enabling translation of the flexible drive shaft without requiring complex exterior slide mechanisms to accommodate the fixed length optical fiber.

Using a handle, such as the handles 1800 and 1900 shown in FIGS. 8A-9B, configured so that the inner drive shaft can be extended axially at the distal end without requiring axial movement of the drive shaft at the proximal end, advantageously allows the handle to be locked in position relative to the drive mechanism, thereby eliminating the need for a linear slide in the drive mechanism to manage the fixed length of the optical fiber, simplifying the mechanical design and the user requirements.

In one embodiment, the atherectomy catheters described herein include a flush port close to the cutter. The flush port can be used to deliver flushing fluid to the area of imaging, thereby improving image quality. Referring to FIGS. 9A-9B, in some embodiments, the flushing can be activated through a luer 1998 on the handle 1900. The luer 1998 can be located just distal of the user ring 1910 on the handle 1900 and can be part of a rotating hemostasis valve component in the handle body.

Figure 10:
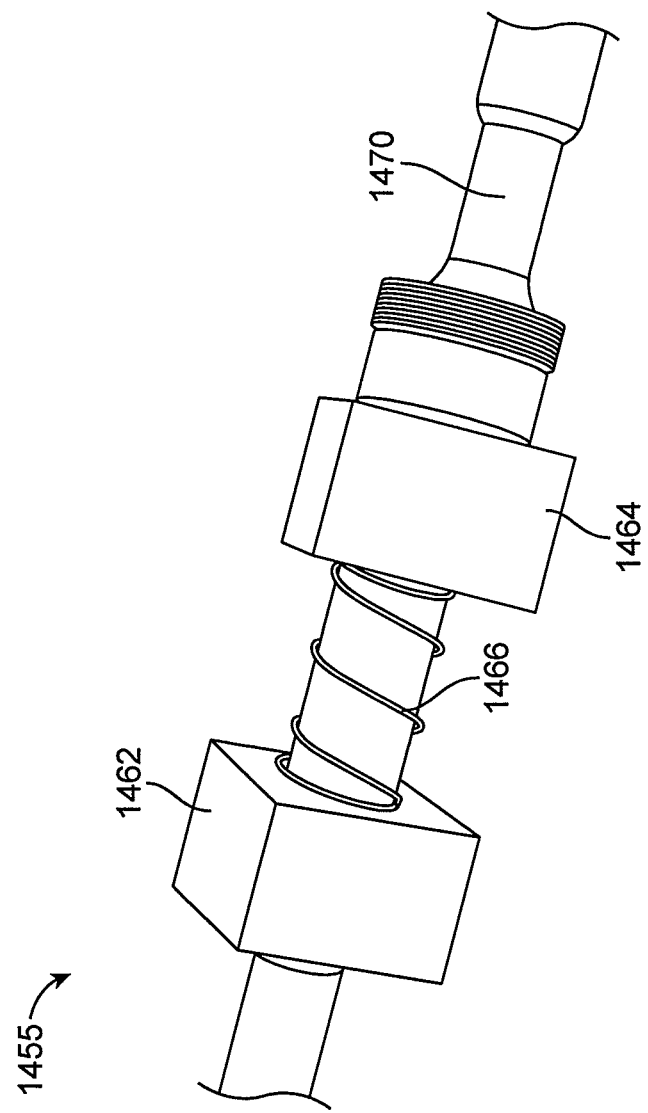
FIG. 10 shows an exemplary optical alignment feature of a catheter handle for connection to a drive system.
Figure 11:
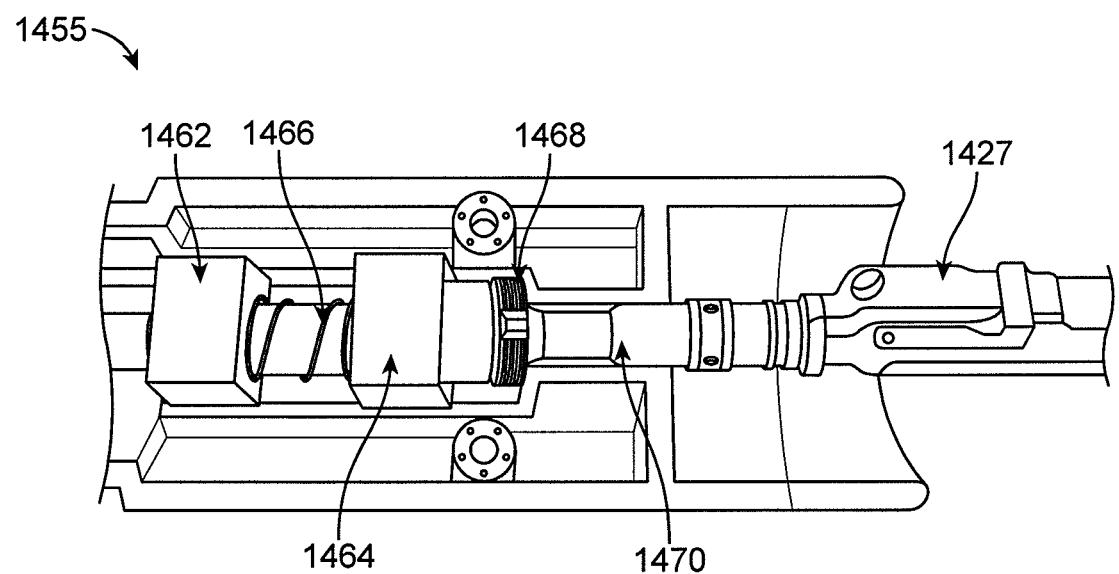
FIG. 11 shows an exemplary optical connection feature of a handle that includes the optical alignment feature of FIG. 10.
Figure 12:
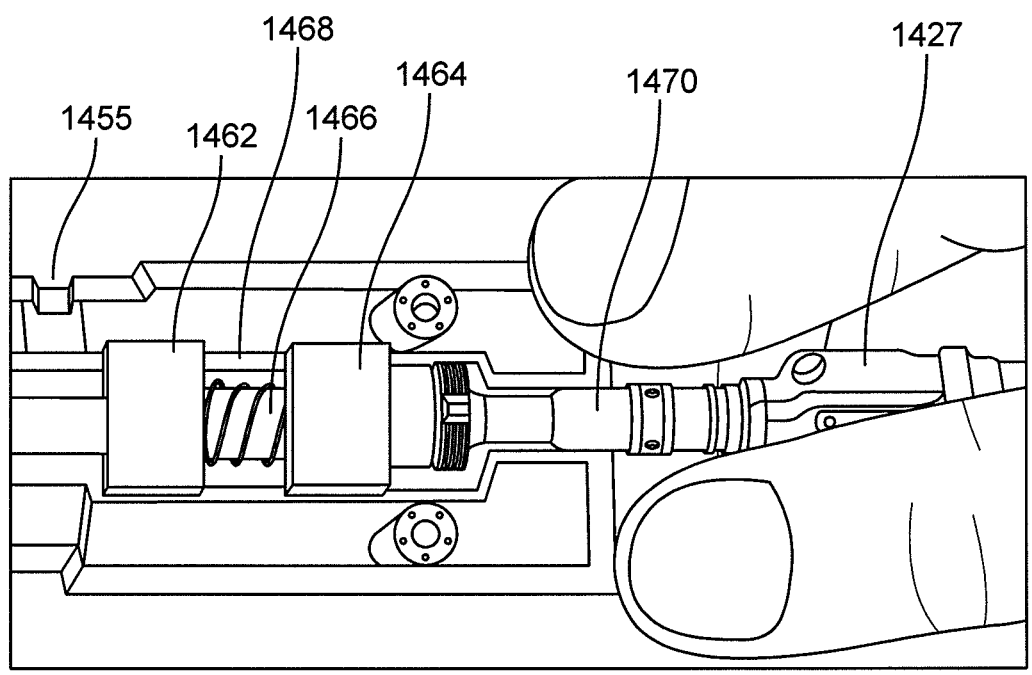
FIG. 12 shows the optical connection of FIG. 11 in a compressed configuration.

Referring to FIGS. 10-12, any of the handles described herein can include an optical connector mechanism 1455 mechanism to establish and maintain the connection between the catheter and the drive system 1400. The connector mechanism 1455 can be a spring-loaded piston mechanism includes a distal bushing 1462, a proximal bushing 1464, and a compression spring 1466. The connector mechanism 1455 can produce a spring force along the optical fiber axis to maintain the connection between the optical connector 1427 and the optical connector of the drive system to which the handle is connected.

As shown in FIGS. 11 and 12, the connector mechanism 1455 can be configured to sit in a restraining track 1468 in the handle. The two bushings 1462 and 1464 can provide multiple functions including: (1) provide bearing surfaces for catheter rotation; (2) serve as end stops between which the compression spring 1466 is captured; and (3) the proximal bushing can slide within the handle enclosure, allowing the connector and catheter assembly to slide axially during connector engagement/disengagement. The bushings 1462, 1464 and the spring 1466 can lie concentric to a fiber coupler 1470, which can link the optical connector 1427 of the drive system (see FIG. 11) to the bushing-spring assembly. In some embodiments, the fiber coupler 1470 can also include a flange feature which serves to push on the proximal bushing 1464 to compress the bushing-spring assembly, thereby maintaining connection to the drive system. In some embodiments, a compression spring force below 1 lb, such as below 0.75 lbs produces the proper connection of the optical connector interface while avoiding image distortion. Further, in some embodiments, the spring force of the compression spring 1466 is greater than 0.05 lbs., such as greater than 0.1 lbs. to overcome material friction. In some embodiments, the spring-loaded mechanism can also provide compliance for the handle, allowing for slight movement of the proximal end of the fiber relative to the handle.

Any of the catheters described herein can further include a guidewire lumen, such as a monorail guidewire lumen. In some embodiments, the monorail guidewire lumen can run parallel to one or more of the struts or markers in the imaging window, thereby not hindering the imaging of the vessel. In other embodiments, the guidewire lumen can be used an imaging marker to identify the orientation of the device.

Any of the shafts described herein (such as the imaging shaft, drive shaft, or outer shafts) can be made of a multi-layer coil. The shafts can include, for example, stainless steel. In one exemplary embodiments, the shaft can be made of 8 adjacent filars wound in one direction with another layer of 8 filars wound in the opposite direction on top of the first layer. The number of filars on each layer may vary as might the diameter of the filars. The drive cable may also comprise 3 layers of filars, adjacent layers being wound in opposite directions.

The catheters described herein can be driven with a reusable drive system, which can provide the torque for the drive shaft and/or optical fiber as well as the optical connection from a light source. Exemplary drive shafts are described in U.S. patent application Ser. No. 13/654,357, titled "ATHERECTOMY CATHETERS AND NON-CONTACT ACTUATION MECHANISM FOR CATHETERS," filed Oct. 17, 2012 and International Patent Application titled "ATHERECTOMY CATHETER DRIVE ASSEMBLIES," filed herewith, all of which are incorporated by reference in their entireties.

Further, as described above, the catheters described herein can be used with optical coherence tomography imaging. Exemplary optical coherence tomography systems are described in copending patent applications: U.S. patent application Ser. No. 12/790,703, titled "OPTICAL COHERENCE TOMOGRAPHY FOR BIOLOGICAL IMAGING," filed May 28, 2010, Publication No. US-2010-0305452-A1; U.S. patent application Ser. No. 12/829,267, titled "CATHETER- BASED OFF-AXIS OPTICAL COHERENCE TOMOGRAPHY IMAGING SYSTEM," filed Jul. 1, 2010, Publication No. US-2011-0021926-A1; and International Patent Application titled "OPTICAL COHERENCE TOMOGRAPHY WITH GRADED INDEX FIBER FOR BIOLOGICAL IMAGING," filed herewith, all of which are incorporated by reference in their entireties. In some embodiments, side-firing optical fibers can be used in place of the reflective elements to direct the OCT signal into the tissue.

Additional details pertinent to the present invention, including materials and manufacturing techniques, may be employed as within the level of those with skill in the relevant art. The same may hold true with respect to method-based aspects of the invention in terms of additional acts commonly or logically employed. Further, it is to be understood that although specific embodiments are described above, elements of one or more of each of the embodiments can be combined or added while still falling within the scope of this disclosure. Thus, it is contemplated that any optional feature of the inventive variations described may be set forth and claimed independently, or in combination with any one or more of the features described herein. Likewise, reference to a singular item, includes the possibility that there is a plurality of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

What is claimed is:

1. An atherectomy catheter comprising:
an elongate flexible catheter body;
a cutter near the distal end of the catheter body;
an elongate distal tip connected to the catheter body at an off-axis hinge point, the elongate distal tip including a cutting window therein;
a drive shaft connected to the cutter and extending within the catheter body;
an imaging element near the distal end of the catheter body; and
an inflatable element attached to the elongate flexible catheter body proximate to the hinge point and opposite to the cutting window, the inflatable element configured to inflate to urge the cutter against a vessel wall; and
wherein the drive shaft is configured to be axially translated relative to the catheter body.

2. The atherectomy catheter of claim 1, further comprising an imaging shaft connected to the imaging element and extending within the catheter body, wherein the cutter and the imaging element are mechanically isolated from one another, and wherein the drive shaft and imaging shaft are decoupled along the length of the catheter body.

3. The atherectomy catheter of claim 1, further comprising an imaging shaft connected to the imaging element and extending within the catheter body, wherein the cutter and the imaging element are mechanically isolated from one another, and wherein the drive shaft and imaging shaft are coupled at a proximal end of the device.

4. The atherectomy catheter of claim 3, the device further comprising a handle configured to transmit torque simultaneously to the proximal end of the drive shaft and the imaging shaft, wherein the drive shaft and imaging shaft are coupled within the handle.

5. The atherectomy catheter of claim 4, wherein the handle includes a translation mechanism configured to translate the drive shaft without translating the imaging shaft.

6. The atherectomy catheter of claim 1, the cutting window sized and dimensioned so as to cause tissue to invaginate within the cutting window.

7. The atherectomy catheter of claim 1, wherein the imaging element includes an optical fiber.

8. The atherectomy catheter of claim 1, wherein the imaging element includes an optical coherence tomography imaging element.

9. An atherectomy catheter comprising:
an elongate flexible catheter body;
a cutter near the distal end of the catheter body;
a drive shaft connected to the cutter and extending within the catheter body;
an imaging element near the distal end of the catheter body; and
an imaging shaft connected to the imaging element and extending within the catheter body, wherein the drive shaft and imaging shaft are concentric, and wherein the drive shaft extends within the imaging shaft;
wherein the cutter and the imaging element are mechanically isolated; and
wherein the drive shaft is configured to be axially translated relative to the imaging shaft and the catheter body.

10. The atherectomy catheter of claim 9, wherein the drive shaft and the imaging shaft both extend substantially along a central axis of the catheter body.

11. The atherectomy catheter of claim 9, wherein the imaging element includes an optical fiber, the optical fiber extending off-axis along the length of the catheter body.

12. An atherectomy catheter comprising:
an elongate flexible catheter body;
a cutter near the distal end of the catheter body;
a drive shaft connected to the cutter and extending within the catheter body;

an imaging element near the distal end of the catheter body; and an imaging shaft connected to the imaging element and extending within the catheter body, wherein the drive shaft and imaging shaft are concentric, and wherein the imaging shaft extends within the drive shaft;

wherein the cutter and the imaging element are mechanically isolated; and wherein the drive shaft is configured to be axially translated relative to the imaging shaft and the catheter body.

13. The atherectomy catheter of claim 12, wherein a distal end of the drive shaft includes a clear annular portion connected to the cutter.

14. An atherectomy catheter comprising:
an elongate flexible catheter body;
a drive shaft extending within the catheter body, the drive shaft having a cutter attached thereto;
an elongate distal tip connected to the catheter body at a hinge point, the elongate distal tip including a cutting window therein; and
an inflatable body linked to both the elongate flexible catheter body and to the elongate distal tip proximate to the hinge point and opposite to the cutting window, wherein inflation of the inflatable body urges the cutter through the cutting window and against a wall of the vessel.

15. The atherectomy catheter of claim 14, further comprising a biasing mechanism configured to return the elongate distal tip to a position approximately axially aligned with the catheter body.

16. The atherectomy catheter of claim 14, wherein the biasing mechanism includes a wedge activated by placing axial force on the drive shaft.

17. The atherectomy catheter of claim 14, the cutting window having an asymmetric shape configured to prevent the cutter from hitting a distal edge of the cutting window.

18. The atherectomy catheter of claim 14, further comprising an imaging element attached to the cutter and configured to rotate therewith.

19. The atherectomy catheter of claim 18, wherein the imaging element is an optical coherence tomography imaging element.

20. The atherectomy catheter of claim 18, wherein the imaging element includes an optical fiber, the optical fiber extending through the drive shaft substantially on-axis with the catheter body.

21. An atherectomy assembly comprising:
an elongate flexible catheter body;
a drive shaft extending within the catheter body, the drive shaft having a rotatable cutter attached thereto, wherein the drive shaft is axially movable with respect to the elongate flexible catheter body;
an optical fiber attached to the cutter and configured to rotate therewith; and
a handle having a distal end attached to the elongate body and a proximal end configured to connect the optical fiber to a light source, wherein the handle is configured such the optical fiber is axially movable with respect to the distal end and axially fixed with respect to the proximal end.

22. The atherectomy assembly of claim 21, wherein the handle includes a tube within which the optical fiber resides.

23. The atherectomy assembly of claim 22, wherein the optical fiber is configured to wind within the tube.

24. The atherectomy assembly of claim 22, wherein the tube is shaped as a ring, wherein the optical fiber is configured to conform to an outer perimeter of the tube when in a compressed configuration and to conform to an inner perimeter of the tube when in an extended configuration.

25. The atherectomy assembly of claim 21, wherein the optical fiber is configured to transmit an optical coherence tomography signal.

26. The atherectomy catheter of claim 14, further comprising a sling extending along an outer surface of the inflatable body configured to link the inflatable body to both the elongated flexible catheter body and the elongated distal tip.

27. The atherectomy catheter of claim 14, wherein the hinge is positioned off of a central axis of the elongate flexible catheter body.

28. The atherectomy assembly of claim 21, further comprising an inflatable element attached to the elongate flexible catheter body.

29. The atherectomy assembly of claim 28, wherein the inflatable element is configured to urge the rotatable cutter against a vessel wall.

30. The atherectomy assembly of claim 28, wherein the inflatable element is approximately spherical.

31. The atherectomy assembly of claim 28, wherein the inflatable element is configured to block blood flow to a distal end of the optical fiber during use.

32. The atherectomy assembly of claim 21, further comprising an elongate distal tip connected to the elongate flexible catheter body at an off-axis hinge point.

33. The atherectomy assembly of claim 28, further comprising a cutting window, wherein the inflatable element is positioned opposite to the cutting window.

* * * * *